(12) United States Patent
Suri

(10) Patent No.: US 8,532,360 B2
(45) Date of Patent: Sep. 10, 2013

(54) IMAGING BASED SYMPTOMATIC CLASSIFICATION USING A COMBINATION OF TRACE TRANSFORM, FUZZY TECHNIQUE AND MULTITUDE OF FEATURES

(75) Inventor: Jasjit S. Suri, Roseville, CA (US)

(73) Assignee: Atheropoint LLC, Roseville, CA (US)

( * ) Notice: Subject to any disclaimer, the term of this patent is extended or adjusted under 35 U.S.C. 154(b) by 159 days.

(21) Appl. No.: 13/253,952

(22) Filed: Oct. 5, 2011

(65) Prior Publication Data

US 2012/0078099 A1     Mar. 29, 2012

Related U.S. Application Data

(63) Continuation-in-part of application No. 13/219,695, filed on Aug. 28, 2011, which is a continuation-in-part of application No. 13/107,935, filed on May 15, 2011, which is a continuation-in-part of application No. 13/077,631, filed on Mar. 31, 2011, which is a continuation-in-part of application No. 13/053,971, filed on Mar. 22, 2011, which is a continuation-in-part of application No. 12/960,491, filed on Dec. 4, 2010, which is a continuation-in-part of application No. 12/896,875, filed on Oct. 2, 2010, which is a continuation-in-part of application No. 12/802,431, filed on Jun. 7, 2010, now Pat. No. 8,313,437, which is a continuation-in-part of application No. 12/799,177, filed on Apr. 20, 2010.

(51) Int. Cl.
*G06K 9/00*     (2006.01)
*A61B 5/05*     (2006.01)

(52) U.S. Cl.
USPC ......................... 382/131; 382/224; 600/410

(58) Field of Classification Search
USPC ................. 382/100, 128, 129, 130, 131, 132, 382/133, 134, 162, 173, 181, 224, 232, 254, 382/274, 276, 305, 312; 600/441, 410, 458; 378/21, 4
See application file for complete search history.

(56) References Cited

U.S. PATENT DOCUMENTS

| | | | |
|---|---|---|---|
| 5,343,867 | A | 9/1994 | Shankar |
| 5,734,739 | A | 3/1998 | Sheehan et al. |
| 6,132,373 | A | 10/2000 | Ito et al. |
| 6,251,072 | B1 | 6/2001 | Ladak et al. |

(Continued)

FOREIGN PATENT DOCUMENTS
WO     WO03042921 A     5/2003

*Primary Examiner* — Seyed Azarian
(74) *Attorney, Agent, or Firm* — Inventive Patent Law P.C.; Jim H. Salter

(57) ABSTRACT

Characterization of carotid atherosclerosis and classification of plaque into symptomatic or asymptomatic and risk score estimation are of clinical value. A statistical system is described for symptomatic versus asymptomatic plaque automated classification of carotid ultrasound images and cardiovascular risk score computation. The technique is applicable for the following types of modalities for carotids: 2D Ultrasound, 3D Ultrasound, CT, MR. Wall region is segmented and features are extracted consisting of type 1 combination consisting of: (a) Higher Order Spectra; (b) Discrete Wavelet Transform (DWT); (c) Texture and (d) Wall Variability; type 2 combination consisting of: (a) Local Binary Pattern; (b) Law's Mask Energy and (c) Wall Variability and type 3 combination: (a) Trace Transform; (b) Fuzzy Grayscale Level Co-occurrence Matrix and (c) Wall Variability. These features are trained using a training classifier on training images and the coefficients are applied to on-line test patient images. The system yields the cardiovascular risk score value using the feature combinations.

19 Claims, 42 Drawing Sheets

(56) References Cited

U.S. PATENT DOCUMENTS

| | | |
|---|---|---|
| 6,267,728 B1 | 7/2001 | Hayden |
| 6,347,152 B1 | 2/2002 | Shinagawa et al. |
| 6,597,937 B2 | 7/2003 | Liu et al. |
| 6,614,453 B1 | 9/2003 | Suri et al. |
| 6,718,055 B1 | 4/2004 | Suri |
| 6,785,409 B1 | 8/2004 | Suri |
| 6,813,373 B1 | 11/2004 | Suri et al. |
| 6,817,982 B2 | 11/2004 | Fritz et al. |
| 6,835,177 B2 | 12/2004 | Fritz et al. |
| 6,842,638 B1 | 1/2005 | Suri et al. |
| 6,845,260 B2 | 1/2005 | Liu et al. |
| 6,987,568 B2 | 1/2006 | Dana |
| 7,020,314 B1 | 3/2006 | Suri et al. |
| 7,024,027 B1 | 4/2006 | Suri et al. |
| 7,074,187 B2 | 7/2006 | Selzer et al. |
| 7,110,000 B2 | 9/2006 | Zhang et al. |
| 7,149,368 B2 | 12/2006 | Tong et al. |
| 7,161,601 B2 | 1/2007 | Zhang et al. |
| 7,272,241 B2 | 9/2007 | Demi et al. |
| 7,340,083 B2 | 3/2008 | Yuan et al. |
| 7,353,117 B2 | 4/2008 | Yuan et al. |
| 7,376,253 B2 | 5/2008 | Spreeuwers et al. |
| 7,639,261 B2 | 12/2009 | Sekine et al. |
| 7,657,299 B2 * | 2/2010 | Huizenga et al. ............ 600/410 |
| 7,680,330 B2 | 3/2010 | Leung |
| 7,686,764 B2 | 3/2010 | Watanabe et al. |
| 2003/0053669 A1 * | 3/2003 | Suri et al. ...................... 382/130 |
| 2003/0236460 A1 | 12/2003 | Ma et al. |
| 2004/0243365 A1 | 12/2004 | Yuan et al. |
| 2005/0042222 A1 | 2/2005 | Yamamoto et al. |
| 2005/0043614 A1 | 2/2005 | Huizenga et al. |
| 2005/0119555 A1 | 6/2005 | Fritz et al. |
| 2006/0064016 A1 | 3/2006 | Demi et al. |
| 2006/0241465 A1 * | 10/2006 | Huennekens et al. ........ 600/458 |
| 2007/0003116 A1 | 1/2007 | Yuan et al. |
| 2007/0038061 A1 | 2/2007 | Huennekens et al. |
| 2007/0269086 A1 * | 11/2007 | Kerwin et al. ................ 382/128 |
| 2007/0287897 A1 | 12/2007 | Faris |
| 2008/0009702 A1 | 1/2008 | Liu et al. |
| 2008/0051658 A1 * | 2/2008 | Demi et al. ................... 600/441 |
| 2008/0080755 A1 | 4/2008 | Payonk et al. |
| 2008/0095422 A1 * | 4/2008 | Suri et al. ..................... 382/131 |
| 2008/0145841 A1 | 6/2008 | Libutti et al. |
| 2008/0171939 A1 | 7/2008 | Ishihara |
| 2008/0221446 A1 | 9/2008 | Washburn et al. |
| 2008/0269595 A1 | 10/2008 | Wong |
| 2008/0274457 A1 | 11/2008 | Eng et al. |
| 2008/0316374 A1 | 12/2008 | Koike et al. |
| 2009/0028793 A1 | 1/2009 | Neri et al. |
| 2009/0252395 A1 | 10/2009 | Chan et al. |
| 2010/0060644 A1 | 3/2010 | Elie et al. |
| 2010/0081931 A1 | 4/2010 | Destrempes et al. |

\* cited by examiner

| Feature | Asymptomatic | Symptomatic | p-value |
|---|---|---|---|
| e1Res (38 degree) | 0.477 ± 6.196E-02 | 0.418 ± 5.834E-02 | 0.0089 |
| e1Res (39 degree) | 0.470 ± 6.751E-02 | 0.407± 6.627E-02 | 0.010 |
| e2Res (39 degree) | 9.833E-02±4.172E-02 | 6.132E-02±2.396E-02 | 0.0085 |
| ePRes (106 degree) | 0.843 ±0.344 | 1.35 ±0.602 | 0.0014 |
| ePRes (107 degree) | 0.828 ±0.280 | 1.18 ±0.494 | 0.0061 |
| CAMES IMTVpoly | 0.256 ±0.193 | 0.484 ±0.191 | 0.0017 |

Figure 29 (table)

SYMPTOMATIC VS. ASYMPTOMATIC CLASSIFIER MEASURES OBTAINED USING ALL
GREYSCALE FEATURES EXCEPT WALL VARIABILITY ($4^{TH}$ FEATURE)

| Classifier | TN | FN | TP | FP | Acc (%) | PPV (%) | Sn (%) | Sp (%) |
|---|---|---|---|---|---|---|---|---|
| SVM | | | | | | | | |
| Linear Kernel | 9 | 2 | 1 | 0 | 83.3 | 83.3 | 44.4 | 96.3 |
| Polynomial Kernel of order 1 | 9 | 2 | 1 | 0 | 83.3 | 83.3 | 44.4 | 96.3 |
| Polynomial Kernel of order 2 | 9 | 2 | 1 | 0 | 83.3 | 83.3 | 44.4 | 96.3 |
| Polynomial Kernel of order 3 | 9 | 2 | 1 | 0 | 83.3 | 83.3 | 44.4 | 96.3 |
| RBF Kernel | 9 | 2 | 1 | 0 | 83.3 | 83.3 | 44.4 | 96.3 |
| Other classifiers | | | | | | | | |
| KNN | 8 | 2 | 1 | 1 | 80.6 | 77.8 | 44.4 | 92.6 |
| PNN | 8 | 2 | 1 | 1 | 80.6 | 77.8 | 44.4 | 92.6 |
| DT | 7 | 1 | 2 | 2 | 75 | 50 | 55.6 | 81.5 |
| Fuzzy | 6 | 1 | 2 | 3 | 66.7 | 42.9 | 66.7 | 66.7 |

Figure 30 (table)

SYMPTOMATIC VS. ASYMPTOMATIC CLASSIFIER PERFORMANCE MEASURES
OBTAINED USING ALL GREYSCALE FEATURES INCLUDING WALL VARIABILITY

| Classifier | TN | FN | TP | FP | Acc (%) | PPV (%) | Sn (%) | Sp (%) |
|---|---|---|---|---|---|---|---|---|
| SVM | | | | | | | | |
| Linear Kernel | 9 | 2 | 1 | 0 | 86.1 | 100 | 44.4 | 100 |
| Polynomial Kernel of order 1 | 9 | 2 | 1 | 0 | 86.1 | 100 | 44.4 | 100 |
| Polynomial Kernel of order 2 | 9 | 1 | 2 | 0 | 88.9 | 91.7 | 66.7 | 96.3 |
| Polynomial Kernel of order 3 | 8 | 1 | 2 | 1 | 83.3 | 83.3 | 66.7 | 88.9 |
| RBF Kernel | 9 | 1 | 2 | 0 | 88.9 | 100 | 55.6 | 100 |
| Other classifiers | | | | | | | | |
| KNN | 9 | 0 | 3 | 0 | 94.4 | 91.7 | 88.9 | 96.3 |
| PNN | 8 | 0 | 3 | 1 | 91.7 | 83.3 | 88.9 | 92.6 |
| DT | 8 | 1 | 2 | 1 | 77.8 | 66.7 | 55.6 | 85.2 |
| Fuzzy | 8 | 0 | 3 | 1 | 86.1 | 70 | 88.9 | 85.2 |

Figure 31A (table)

Table 2. *Wall-dataset*: Significant features that had a p-value < 0.0001 and their ranges for symptomatic and asymptomatic classes

| Feature | Asymptomatic | Symptomatic | p-value |
|---|---|---|---|
| LBP(R=3,P=24)Energy ($LBP_{324}Ene$) | 0.9137±0.1957 | 0.3096±0.1272 | 0.0000 |
| Laws Mask Energy 2 ($LME2$) | 3.1159e+007±1.6741e+007 | 4.8117e+006±3.7818e+006 | 0.0000 |
| Laws Mask Energy 8 ($LME8$) | 1.9635e+007±1.3902e+007 | 2.3464e+006±2.3664e+006 | 0.0000 |
| $IMTV_{poly}$ | 0.104±8.298E-02 | 0.484 ±0.191 | 0.0000 |

Figure 31B (table)

| Classifier | TN | FN | TP | FP | Accu | PPV | Sn | Sp |
|---|---|---|---|---|---|---|---|---|
| SVM with features: FD, LBP and Law's Mass Energy (LME) | | | | | | | | |
| Linear | 2 | 10 | 89 | 1 | 88.9 | 99 | 89.6 | 66.7 |
| Polynomial (order 1) | 2 | 10 | 89 | 1 | 88.9 | 99 | 89.6 | 66.7 |
| Polynomial (order 2) | 2 | 10 | 89 | 1 | 88.9 | 99 | 89.6 | 66.7 |
| Polynomial (order 3) | 2 | 10 | 89 | 1 | 88.9 | 99 | 89.6 | 66.7 |
| RBF | 2 | 10 | 89 | 1 | 89.2 | 99.3 | 89.6 | 77.8 |
| Other Classifiers (KNN and RB-PNN) | | | | | | | | |
| KNN | 3 | 10 | 89 | 0 | 89.5 | 99.7 | 89.6 | 88.9 |
| RBPNN | 3 | 10 | 89 | 0 | 89.5 | 99.7 | 89.6 | 88.9 |

Figure 31C (table)

AtheroEdge™ parameters and experimental values used.

| Parameter | Value | Experimental Range and Effect |
|---|---|---|
| Stage-I ($AD_F$ Identification) | | |
| Scale Parameter ($\sigma$) | 8 pixels | $\sigma = 6\text{-}10$ pixels. Scale of the 1$^{st}$ order Gaussian Kernel derivative during the stage I process. |
| ROI width for lumen validation ($ROI_{Lumen}$) | 30 pixels | Sequence of points above $AD_F$ to check for lumen test. |
| Lumen test failure threshold ($T_{Lumen}$) | 15 pixels | Threshold for passing the lumen test. |
| Spike detection threshold ($T_{Spike}$) | 15 pixels | $T_{Spike} = 12 - 16$ pixels. Determines the difference between consecutive points of a profile that we consider a spike. |
| Stage II (LI/MA segmentation) | | |
| MRFOAM Calibration Factor ($\eta_{MRFOAM}$) | 0.3 mm | Determines noise robustness and LI/MA accuracy. |
| Gaussian Kernel size ($\theta_1$) | 5 pixels | $\theta_1 = \eta_{MRFOAM} / \tau_{Nicosia}$ Implements the GoG filter. ($\tau_{Nicosia}$ is the conversion factor of Table I) |
| Gaussian Kernel size ($\theta_2$) | 10 pixels | $\theta_2 = 2\theta_1$ Implements the GoG filter |
| Gaussian Kernel size ($\theta_3$) | 5 pixels | $\theta_3 = \eta_{MRFOAM} / \tau_{Nicosia}$ Regularization parameter. ($\tau_{Nicosia}$ is the conversion factor of Table I) |
| Gaussian scale $\sigma_1$ and $\sigma_3$ | 2 pixels | $\sigma_i = \lceil \theta_i / 3 \rceil$ |
| Gaussian scale $\sigma_2$ | 3 pixels | |

Figure 32 (table), AtheroEdge Parameters

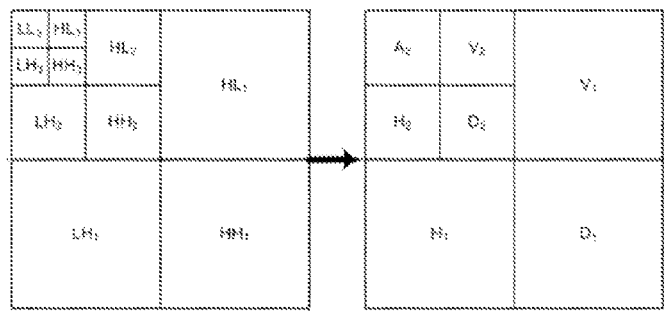
Figure 41
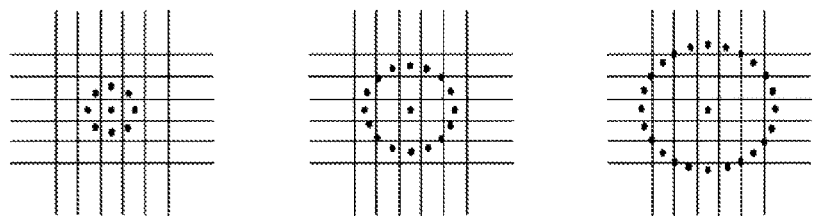
Figure 42
|  | Asymptomatic | Symptomatic | p-value |
|---|---|---|---|
| *AtheromaticWi* | 0.889 ±0.684 | 5.31 ±1.88 | 0.0000 |
Figure 43

IMAGING BASED SYMPTOMATIC CLASSIFICATION USING A COMBINATION OF TRACE TRANSFORM, FUZZY TECHNIQUE AND MULTITUDE OF FEATURES

PRIORITY APPLICATIONS

This is a continuation-in-part patent application of co-pending patent application Ser. No. 12/799,177; filed Apr. 20, 2010 by the same applicant. This is also a continuation-in-part patent application of patent application Ser. No. 12/802,431; filed Jun. 7, 2010 now U.S. Pat. No. 8,313,437 by the same applicant. This is also a continuation-in-part patent application of co-pending patent application Ser. No. 12/896,875; filed Oct. 2, 2010 by the same applicant. This is also a continuation-in-part patent application of co-pending patent application Ser. No. 12/960,491; filed Dec. 4, 2010 by the same applicant. This is also a continuation-in-part patent application of co-pending patent application Ser. No. 13/053,971; filed Mar. 22, 2011 by the same applicant. This is also a continuation-in-part patent application of co-pending patent application Ser. No. 13/077,631; filed Mar. 31, 2011 by the same applicant. This is also a continuation-in-part patent application of co-pending patent application Ser. No. 13/107,935; filed May 15, 2011 by the same applicant. This is also a continuation-in-part patent application of co-pending patent application Ser. No. 13/219,695; filed Aug. 28, 2011 by the same applicant. This present patent application draws priority from the referenced co-pending patent applications. The entire disclosures of the referenced co-pending patent applications are considered part of the disclosure of the present application and are hereby incorporated by reference herein in its entirety.

TECHNICAL FIELD

This patent application relates to methods and systems for use with data processing, data storage, and imaging systems, according to one embodiment, and more specifically, for medical image processing.

BACKGROUND

Atherosclerosis (or arteriosclerotic vascular disease) is a condition in which an artery wall thickens as a result of deposition of materials such as cholesterol, fat, and other substances resulting in the formation of hard structures called plaques. Formation of plaques makes the arteries stiff and narrow (stenosis), thereby restricting blood supply to the involved organs. Such restricted blood supply would damage the organ, and eventually lead to its failure. Pieces of plaque can also break away and move from the affected artery to smaller blood vessels, block these vessels completely, and consequently, result in tissue damage and death (embolization). This embolization process is one of the causes of heart attack and stroke. Recent statistics from the World Health Organization indicate that such cardiovascular diseases (CVDs) are the world's largest killers, resulting in 17.1 million deaths a year. Estimates indicate that by 2030, almost 23.6 million people will die from CVDs, mainly from heart disease and stroke. The earliest risk indicator of a possible CVD is the presence of atherosclerosis. Early detection of atherosclerosis and adequate treatment and lifestyle changes would enable the patient to prevent the onset of a CVD. Unfortunately, atherosclerosis is a chronic disease that remains asymptomatic for decades. Therefore, development of techniques that detect the presence of plaque at its earliest stages is of paramount importance.

Owing to its anatomical position and its relatively large diameter, the Common Carotid Artery (CCA) is the preferred artery for routine clinical examination to detect the presence of plaque and to study its characteristics. The examination is mostly carried out using non-invasive carotid artery ultrasound, which is a cost-effective and relatively fast imaging technique that does not use ionising radiation. However, ultrasound technique is operator dependent, and hence, the interpretation is subjective. Moreover, even though studies show that ultrasonographic B-mode characterization of plaque morphology is useful in assessing the vulnerability of atherosclerotic lesions, a confident and reproducible classification of dangerous plaques and its risk score from this plaque is still not available. Also, the correlation between ultrasonographic findings and the histological findings of carotid plaques is often poor. These limitations are due to the low image resolution and artifacts associated with ultrasound imaging. Thus, Computer Aided Diagnostic (CAD) techniques that adequately pre-process the ultrasound images before extracting discriminating features for further classification and giving a risk score would improve the correlation between ultrasound based results and histological results of carotid plaques.

Once plaque is detected, the treatment options to unblock the stenosis include Carotid Artery Stenting (CAS) and Carotid Endarterectomy (CEA). CAS is a non-invasive procedure that uses a catheter to correct stenosis, whereas CEA is a surgical procedure. It has been shown that CEA reduces the risk of ipsilateral stroke. In a clinical trial named CREST, both CAS and CEA were compared on the collective incidence of any stroke, any heart attack or death. The study concluded that there was a higher risk of stroke with CAS and a higher risk of myocardial infarction with CEA. This conclusion indicates that there is a considerable risk for the patient undergoing either of these procedures. Therefore, characterization of the patient as symptomatic or asymptomatic based on the wall plaque morphology would enable the vascular surgeons to decide whether the patient needs such risky procedures. This is because studies have shown that only symptomatic patients were found to have more frequent plaque rupture that cause life-threatening embolization. Plaque rupture was seen in 74% of symptomatic plaques and in only 32% of plaques from asymptomatic patients.

Thus, the development of an efficient completely automated CAD technique that not only detects plaque but also classifies it into symptomatic and asymptomatic while giving a cardiovascular risk score would immensely assist the doctors in managing atherosclerosis.

SUMMARY OF THE VARIOUS EMBODIMENTS

Atherosclerosis is a degenerative disease of the arteries that results in the formation of plaques, and consequent narrowing of blood vessels (stenosis). Characterization of carotid atherosclerosis and classification of plaque into symptomatic or asymptomatic along with the risk score estimation are key steps necessary for allowing the vascular surgeons to decide if the patient has to definitely undergo risky treatment procedures that are needed to unblock the stenosis. This application describes a (a) Computer Aided Diagnostic (CAD) technique for symptomatic versus asymptomatic plaque automated classification of carotid ultrasound images and (b) presents a cardiovascular risk score computation in longitudinal 2D Ultrasound, cross-sectional MR, CT and 3D Ultrasound and 3D IVUS. We show this for Ultrasound, CT and MR modalities and extendable to 3D Carotid Ultrasound and 3D IVUS.

The on-line system consists of Atherosclerotic Wall Region estimation using AtheroEdge™ (for longitudinal Ultrasound) or Athero-CTView™ (for CT) or Athero-MR-View (for MR) and extendable to 3D carotid Ultrasound or 3D IVUS. This grayscale Wall Region is then fed to a feature extraction processor which computes: (a) Higher Order Spectra-based features; (b) Discrete Wavelet Tansform (DWT)-based features; (c) Texture-based features and (d) Wall Variability. The output of the Feature Processor is fed to the Classifier which is trained off-line from the Database of similar Atherosclerotic Wall Region images. The off-line Classifier is trained from the significant features from (a) Higher Order Spectra; (b) Discrete Wavelet Transform (DWT); (c) Texture and (d) Wall Variability, selected using t-test. Symptomatic ground truth information about the training patients is drawn from cross modality imaging such as CT or MR or longitudinal Ultrasound or 3D ultrasound or 3D IVUS in the form of 0 or 1 (1 for symptomatic). Support Vector Machine (SVM) or similar classifier (such as KNN, PNN or Decision Tree or Adaboost) supervised classifier of varying kernel functions is used off-line for training. The obtained training parameters are then used to evaluate the test set. One can then achieve high accuracy with the radial basis function kernel and the one with a polynomial kernel of order two. The system also yields the risk score value on the basis of the wall features. The proposed technique demonstrates that plaque classification between symptomatic vs. asymptomatic could be achieved with a completely automated CAD tool with a significant accuracy. Performance of the system can be evaluated by computing the accuracy, sensitivity, specificity, and Positive Predictive Value (PPV). Hence, such a tool would prove to be a valuable inclusion in the current treatment planning protocol by vascular surgeons.

Most of the existing plaque classification CAD tools rely on human intervention to manually segment the plaque in the ultrasound images before features are extracted and processed. It is known that manual segmentation needs well trained experts in the field, and the results may be different from expert to expert. Generally, patients are considered symptomatic if they had experienced Amaurosis Fugax (AF), Transient Ischemic Attack (TIA), or focal transitory, reversible or established neurological symptoms in the ipsilateral carotid territory in the previous six months. However, in this application, in order to make the proposed technique independent of the previous history of the patients, the ground truth of whether the plaque is symptomatic or asymptomatic is obtained by studying the cross modality (other than ultrasound) such as Computer Tomography (CT) or MRI or 3D Ultrasound or 3D IVUS and their results are obtained from the patients. Patients without any history of recent neurologic symptoms or with nonspecific symptoms such as dizziness and vertigo were considered asymptomatic.

As described herein for various example embodiments, the embodiments can support and effect the following features:

(1) Symptomatic vs. Asymptomatic classification of plaque in the vessel wall region. Such a system would work for the vessel wall (with no plaque in it) or vessel wall (with plaque buildup in it). From now on when we say plaque vessel wall region, we imply that the system will be applicable to vessel wall with no plaque in it (non-plaque vessel walls) and vessel wall with plaque in it (following NASCET criteria).

(2) Cardiovascular risk score estimation, given the plaque vessel wall region.

(3) A data mining on-line system for Symptomatic vs. Asymptomatic classification of the patient image and cardiovascular risk score estimation, where the Atherosclerotic plaque region in the Arterial Wall (Atherosclerotic Wall Region (AWR)) is semi-automatically or automatically or manually computed.

(4) A data mining on-line system for Symptomatic vs. Asymptomatic classification of the patient image and cardiovascular risk score estimation, where as the training-based system computes features from the images in the Atherosclerotic Wall Region (AWR).

(5) A data mining on-line system for Symptomatic vs. Asymptomatic classification of the patient image and Cardiovascular risk score estimation, where as the training-based system computes features in the AWR and the training ground truth information can be taken from the cross-modality CT or MR or 3D ultrasound or 3D IVUS or longitudinal ultrasound itself.

(6) A data mining on-line system for Symptomatic vs. Asymptomatic classification of the patient image and Cardiovascular risk score estimation, where as the training-based system computes features in the Atherosclerotic Wall Region (AWR) and the training ground truth information can be taken from the cross-modality CT or MR or 3D ultrasound or 3D IVUS or longitudinal ultrasound itself, and where the on-line features are computed using a non-linear behaviour of a carotid stenosis and cerebrovascular disease.

(7) A data mining on-line system for Symptomatic vs. Asymptomatic classification of the patient image and Cardiovascular risk score estimation, where as the training-based system computes features in the AWR, and the training ground truth information can be taken from the cross-modality CT or MR or 3D ultrasound or 3D IVUS or longitudinal ultrasound itself, and where the on-line features are computed using a non-linear behaviour of a carotid stenosis and cerebrovascular disease. The non-linear behaviour uses Higher Order Spectra for feature extraction using Bispectrum.

(8) A data mining on-line system for Symptomatic vs. Asymptomatic classification of the patient image and Cardiovascular risk score estimation, where as the training-based system computes features in the AWR and the training ground truth information can be taken from the cross-modality CT or MR or 3D ultrasound or 3D IVUS or longitudinal ultrasound itself, and where the on-line features are computed using a non-linear behaviour of a carotid stenosis and cerebrovascular disease. The non-linear behaviour uses Higher Order Spectra for on-line feature extraction. Higher order statistics denote higher order moments (order greater than two) and non-linear combinations of higher order moments, called the higher order cumulants.

(9) A data mining on-line system for Symptomatic vs. Asymptomatic classification of the patient image and Cardiovascular risk score estimation, where the training-based system computes features in the AWR and the training ground truth information can be taken from the cross-modality CT or MR or 3D ultrasound or 3D IVUS or longitudinal ultrasound itself, where the on-line features are computed using a non-linear behaviour of a carotid stenosis and cerebrovascular disease. The non-linear behaviour uses Higher Order Spectra for feature extraction such as Bispectrum. Higher order statistics denote higher order moments (order greater than two) and non-linear combinations of higher order moments, called the higher order cumulants. The Ultrasound plaque image is subjected to Radon Transform for computation of Phase Entropy.

(10) A data mining on-line system for Symptomatic vs. Asymptomatic classification of the patient image and Cardiovascular risk score estimation, where the training-based system computes features in the AWR and the training ground truth information can be taken from the cross-modality CT or MR or 3D ultrasound or 3D IVUS or longitudinal ultrasound itself, where the on-line features are computed using a non-linear behaviour of a carotid stenosis and cerebrovascular disease. The non-linear behaviour uses Higher Order Spectra for feature extraction such as Bispectrum. Higher order statistics denote higher order moments (order greater than two) and non-linear combinations of higher order moments, called the higher order cumulants. The Ultrasound image is subjected to Radon Transform for computation of Phase Entropy. Also the feature computed is Normalized Bispectral Entropy and Normalized Squared Bispectral Entropy.

(11) A data mining on-line system for Symptomatic vs. Asymptomatic classification of the patient image and Cardiovascular risk score estimation, where the training-based system computes features in the AWR and the training ground truth information can be taken from the cross-modality CT or MR or 3D ultrasound or longitudinal ultrasound itself, where the on-line features are computed using a non-linear behaviour of a carotid stenosis and cerebrovascular disease. The non-linear behaviour uses Higher Order Spectra for feature extraction such as Bispectnim. Higher order statistics denote higher order moments (order greater than two) and non-linear combinations of higher order moments, called the higher order cumulants. The Ultrasound image is subjected to Radon Transform for computation of Phase Entropy. Also the on-line feature computed is Normalized Bispectral Entropy and Normalized Squared Bispectral Entropy. This on-line feature then combines with other features such as from Discrete Wavelet Transform (DWT), Texture, Wall Variability to improve the robustness of the Symptomatic vs. Asymptomatic classification of the patient image and cardiovascular risk score estimation.

(12) A data mining on-line system for Symptomatic vs. Asymptomatic classification of the patient image and Cardiovascular risk score estimation, where the off-line training system uses features like Normalized Bispectral Entropy and Normalized Squared Bispectral Entropy from the Radon Transform of the images in combination with DWT based features in Atherosclerotic Wall Region (AWR).

(13) A data mining system for Symptomatic vs. Asymptomatic classification of the patient image and Cardiovascular risk score estimation, where the off-line training system uses features like Normalized Bispectral Entropy and Normalized Squared Bispectral Entropy from the Radon Transform of the images in combination with DWT based features in Atherosclerotic Wall Region.

(14) A data mining system for Symptomatic vs. Asymptomatic classification of the patient image and Cardiovascular risk score estimation, where the off-line training system uses features like Normalized Bispectral Entropy and Normalized Squared Bispectral Entropy from the Radon Transform of the Atherosclerotic Wall Region in combination with DWT based features in the Atherosclerotic Wall Region. Four decomposition directions corresponding to 0° (horizontal, Dh), 90° (vertical, Dv) and 45° or 135° (diagonal, Dd) orientation were taken using DWT features. Three features such as vertical, horizontal and energy component were derived from the Atherosclerotic Wall Region.

(15) A data mining system for Symptomatic vs. Asymptomatic classification of the patient image and Cardiovascular risk score estimation, where the off-line training system uses features like Normalized Bispectral Entropy and Normalized Squared Bispectral Entropy from the Radon Transform of the Atherosclerotic Wall Region (AWR), DWT based features in Atherosclerotic Wall Region and texture-based features in Atherosclerotic Wall Region.

(16) A data mining system for Symptomatic vs. Asymptomatic classification of the patient image and Cardiovascular risk score estimation, where the off-line training system uses features like Normalized Bispectral Entropy and Normalized Squared Bispectral Entropy from the Radon Transform of the Atherosclerotic Wall Region in combination with DWT based features along with texture-based features, where texture-based features are computed using Gray Level Co-occurrence Matrix and three texture features in Atherosclerotic Wall Region are computed such as: Entropy, Symmetry and Run Length.

(17) A data mining system for Symptomatic vs. Asymptomatic classification of the patient image and Cardiovascular risk score estimation, where the off-line training system uses features like Normalized Bispectral Entropy and Normalized Squared Bispectral Entropy from the Radon Transform of the Atherosclerotic Wall Region in combination with DWT based features along with texture-based features in Atherosclerotic Wall Region. This is in combination with Wall Variability.

(18) A data mining system for Symptomatic vs. Asymptomatic classification of the patient image and Cardiovascular risk score estimation, where the off-line training system uses features like Normalized Bispectral Entropy and Normalized Squared Bispectral Entropy from the Radon Transform of the images in combination with DWT based features along with texture-based features. This is in combination with Wall Variability, where Wall Variability is computed using middle line (or centreline) or polyline methods or any distance methods.

(19) A system for Atherosclerotic Wall Region computation using an algorithm for computing the LI and MA borders of the wall region in longitudinal ultrasound. The region between the LI and MA is the Atherosclerotic Wall Region. Those skilled in the art can apply this to CT wall region, where the two borders are Lumen border and Outer Wall instead of LI and MA borders. Those skilled in the art can also apply to MR wall or IVUS wall where the two borders are lumen wall and outer wall. Those skilled in the art can also apply to 3D Carotid Ultrasound wall where the two borders are lumen wall and outer wall. Those skilled in the art can also apply to 3D IVUS wall where the two borders are lumen wall and outer wall. This system is applicable to longitudinal ultrasound, 3D carotid Ultrasound, carotid MR, Carotid CT.

(20) A system for automated Atherosclerotic Wall Region computation using multi-resolution system.

(21) In another data mining on-line system for Symptomatic vs. Asymptomatic classification of the patient image and Cardiovascular risk score estimation, where as the training-based system computes features in the AWR, and the training ground truth information can be taken from the cross-modality CT or MR or 3D ultrasound or 3D IVUS or longitudinal ultrasound itself, and where the on-line features are computed using a non-linear behaviour of a carotid stenosis and cerebrovascular disease. The non-linear behaviour uses Local Binary Pattern (LBP).

(22) In another data mining on-line system for Symptomatic vs. Asymptomatic classification of the patient image and Cardiovascular risk score estimation, where as the training-based system computes features in the AWR, and the training ground truth information can be taken from the cross-modality CT or MR or 3D ultrasound or 3D IVUS or longitudinal ultrasound itself, and where the on-line features are computed using a non-linear behaviour of a carotid stenosis and cerebrovascular disease. The non-linear behaviour uses Laws Mask Energy (LME).

(23) In another data mining on-line system for Symptomatic vs. Asymptomatic classification of the patient image and Cardiovascular risk score estimation, where as the training-based system computes features in the AWR, and the training ground truth information can be taken from the cross-modality CT or MR or 3D ultrasound or 3D IVUS or longitudinal ultrasound itself, and where the on-line features are computed using a non-linear behaviour of a carotid stenosis and cerebrovascular disease. The non-linear behaviour uses a combination of Local Binary Pattern (LBP) and Laws Mask Energy (LME).

(24) In another data mining on-line system for Symptomatic vs. Asymptomatic classification of the patient image and Cardiovascular risk score estimation, where as the training-based system computes features in the AWR, and the training ground truth information can be taken from the cross-modality CT or MR or 3D ultrasound or 3D IVUS or longitudinal ultrasound itself, and where the on-line features are computed using a non-linear behaviour of a carotid stenosis and cerebrovascular disease. The non-linear behaviour uses a combination of Local Binary Pattern (LBP) and Laws Mask Energy (LME) and Wall Variability.

Automated Wall Border Estimation in longitudinal Ultrasound:

The system of an example embodiment uses Coarse to Fine Resolution Processing: Previous art has focused on methods for either classification of media layer or finding the MA edges in the manual designated ROI. Since it is manual ROI, it is time consuming and non-practical for clinical applications, we have developed a new method which is fast, accurate, reliable and very practical for IMT measurement for ultrasound carotids, brachial, femoral and aortic blood vessels. Since the manual methods are time consuming and requires a lot of training, this applications is a two step stage process: (a) automated artery recognition and (b) automated calibration (segmentation) which finds the LIMA borders more accurately which is then used for Atherosclerotic Wall Region computation. The automated recognition process is hard given the Jugular vein in the neighborhood. Our concept is to recognize the artery in a smaller image with a high speed (so-called coarse resolution) and spot the artery out in longitudinal ultrasound images. The spotted artery can then be seen in the tine resolution or high resolution. This will allow processing the pixels in the correct region of interest. The statistics of the neighboring pixels will not affect the region of interest, which is where the accurate LIMA borders need to be determined. Normally, arteries are about 10 mm wide while the media thickness is about 1 mm wide. It is also known from our experience that the image resolution is about 15 pixels per mm. If we can bring the original resolution to a coarse resolution by one step down sample, we can bring the media layer to about 8 pixels per mm. Further, if this coarse resolution is down sampled by another half, then one can bring the image resolution from 8 pixels per mm to 4 pixels per mm. Thus, if the coarse resolution of the arterial ultrasound vessels has a medial thickness of 4 pixels per mm, one can easily detect such edges by convolving the higher order derivatives of Gaussian kernel with the coarse resolution image. Thus the new concept here to compute Atherosclerotic Wall Region is to automatically detect the arterial wall edges by down sampling the image and convolving the coarse images to higher order derivatives of Gaussian kernels. This allows the media layer to be automatically determined, thus generating the Atherosclerotic Wall Region which is then used for grayscale feature identification such as: FIOS-Bispectrum Phase Entropy, DWT features like vertical and horizontal and energy component (from decomposition directions corresponding to 0° (horizontal, Dh), 90° (vertical, Dv) and 45° or 135° (diagonal, Dd) orientation were taken using DWT features), Texture Features and Wall Variability.

In another methodology, Atherosclerotic Wall Region which is then used for grayscale feature identification such as Local Binary Pattern (LBP) and Laws Mask Energy (LME) and Wall Variability.

Such an approach for automated media layer detection from fine to coarse resolution will further improve the region of interest determination. The art of changing the fine to coarse resolution has been popular in computer vision sciences. There are several methods available to converting the image from high resolution to coarse resolution. One of them is wavelet-based method where wavelets are being applied for down sampling the image to half Another method can be hierarchical down sampling method using Peter Burt's algorithm. Thus the first advantage of the current system is automated recognition of the artery at coarse resolution and then using the MA border for visualization and recognition at the fine resolution (up-sampled resolution). This multi-resolution approach for Atherosclerotic Wall Region computation has several advantages to it:

(i) Robustness and Accurate Wall capture: it is very robust because the higher order derivative kernels are very good in capturing the vessel walls (see, A Review on MR Vascular Image Processing Algorithms: Acquisition and Pre-filtering: Part I, Suri et al., IEEE TRANSACTIONS ON INFORMATION TECHNOLOGY IN BIOMEDICINE, VOL. 6, NO. 4, pp. 324-337, December 2002; and A Review on MR Vascular Image Processing: Skeleton Versus Non skeleton Approaches: Part II, Suri et al., *IEEE TRANSACTIONS ON INFORMATION TECHNOLOGY IN BIOMEDICINE*, VOL. 6, NO. 4, DECEMBER 2002).

(ii) Validation Embedded Segmentation of Vascular IMT estimation: Here the recognition of artery has been validated by the anatomic information during the segmentation process. Since lumen is the anatomic information which is blood carrier to brain and is next to the far adventitia borders, which needs to be located, therefore, this patent application uses the anatomic information (lumen) to ensure that the far adventitia borders are robustly computed and do not penetrate the lumen region or near wall region, while estimating the far adventitia walls. This adds robustness to our automated recognition and Atherosclerotic Wall Region estimation process.

(iii) Faster than the conventional processing: Since the recognition is strategized at coarse level down sampled twice from its original size of the image, it is therefore processing $\frac{1}{4}^{th}$ the number of pixels for automated recognition of the media layer. This improves the speed of the system for computation of Atherosclerotic Wall Region.

(iv) Independent of Orientation of the vascular scan: Another major advantage to the system is that these Gaussian kernels are independent of the orientation of the blood vessels in the image. Since the ultrasound vascular scans do not always have the vessel orientation horizontal with respect bottom edge of the image, manual methods can pose a further challenge towards the Atherosclerotic Wall Region estimation.

(v) Guiding Method for the Calibration System: Since the recognition is followed by the calibration (segmentation) process, the calibration system becomes very robust since the calibration processing is done in the region of interest determined by the automated recognition system. Thus the calibration system adds the value determined by the automated recognition system for vascular ultrasound such as IMT measurement for carotid, femoral, aortic and brachial. Such a combination where the calibration system is guided by the automated recognition system for Atherosclerotic Wall Region estimation and helps in mass processing of huge database processing.

(vi) Running the classification and risk score system real time for Clinical Analysis: Since the recognition is automated followed by the calibration system, the largest value such a system would deliver will be in its real time use for analysis of on-line symptomatic vs. asymptomatic image classification and cardiovascular risk score estimation. Running clinical databases on still images would be even more beneficial because such a system would be completely automated in terms of recognition, Atherosclerotic Wall Region, symptomatic vs. asymptomatic image classification and cardiovascular risk score estimation.

(vii) Applications: Since the ultrasound probes use almost the same frequency of operation for scanning the vascular arteries such as carotid, femoral, brachial and aortic, it is thus possible to use such a system for these blood vessels.

In prior art, we have seen that the speckle reduction has been used for removing speckles in the ultrasound images. Though speckle reduction is common in ultrasound imaging, but the way speckle reduction is used here is very conservative. The idea here is to find out where the LIMA borders are using automated recognition system and then apply the local statistical speckle reduction filter in specific set of pixels which come under the LIMA band or media layer. Such a strategy allows multiple advantages:

(i) Avoiding Large Computation Times on Speckle Reduction: The computation time for speckle reduction is not wasted in such a strategy, unlike conventional methods, where the speckle reduction is part of the whole streamline flow and is being run on the whole image.

(ii) Speckle Reduction is implemented on the original raw intensity in the region estimated at a coarse Resolution: Second, the speckle reduction filter is run in the automated recognized region (MA borders) which is actually applied on the original image rather than on the coarse image. This way the original speckles are removed preserving the intensities of high gradient structures like LI and MA peaks. This is very important because the calibration system acts on these speckle reduction region of interest.

(iii) Guidance to the Calibration System: The calibration system is guided by the speckle reduction filter which is optimized for the region of interest.

Extracting LIMA borders in presence of Calcium Shadow: Calcium is an important component of the media layer. It is not exactly known how the calcium is formed, but it is said that calcium accumulates in the plaques. During the beginning of Atherosclerosis disease, the arterial wall creates a chemical signal that causes a certain type of WBC (white blood cells) such as monocytes and T cells that attaches the arterial wall. These cells then move into the wall of the artery. These T cells or monocyles are then transformed into foam cells, which collect cholesterol and other fatty materials and trigger the growth of the muscle cells (which are smooth in nature) in the artery. Over time, it is these fat-laden foam cells that accumulate into plaque covered with a fibrous cap. Over time, the calcium accumulates in the plaque. Often times, the calcium is seen in the near wall (proximal wall) of the carotid artery or aortic arteries. This causes the shadow cone formation in the distal wall (far wall). As a result the LI boundaries (for Atherosclerotic Wall Region computation) are over computed from its actual layer. The shadow causes the LI lining over the actual LI boundary. As a result, the LI-MA distances are over computed in the shadow zone. Because of this, the Atherosclerotic Wall Region formation is over computed in these cases. This application particularly takes care of Atherosclerotic Wall Region computation during the shadow cone formation. We will see how the actual LI boundaries are recovered if calcium is present causing the shadow cone. As a result, the Atherosclerotic Wall Region computation has the following advantages when using shadow cones (a) Accurate Atherosclerotic Wall Region computation in real time when the calcium is present in the proximal wall (near wall) causing the shadow cone formation; (b) The system allows computing the Atherosclerotic Wall Region in both cases: (a) when calcium is present and when calcium is not present.

BRIEF DESCRIPTION OF THE DRAWINGS

FIG. 23 shows that if there is a calcium cone shadow computes the Atherosclerotic Wall Region and IMT by correcting the IMT so-called the shadow correction. Shadow corrected processes estimates the Atherosclerotic Wall Region and IMT values under calcium shadow projection, while these processes simply run if there is no calcium shadow cone.

FIG. 29 (table) results show the significant features that had a p-value less than 0.05.

FIG. 30 (table) shows the symptomatic vs. asymptomatic classifier measures obtained using all the grayscale features (HOS, Texture and DWT), but without the wall variability feature.

FIGS. 31A, 31B, and 31C (tables) show the symptomatic vs. asymptomatic classifier measures obtained using all the grayscale features (HOS, Texture and DWT), and with the wall variability feature FIG. 32 (table) shows the AtheroEdge™ system parameters for stage I and stage II.

FIG. 41 shows the pass band structure for a 2D sub-band transform at three levels.

FIG. 42 shows the LBP method for computing the texture features.

FIG. 43 shows the table for Atheromatic™ index.

DETAILED DESCRIPTION

Figure 1:
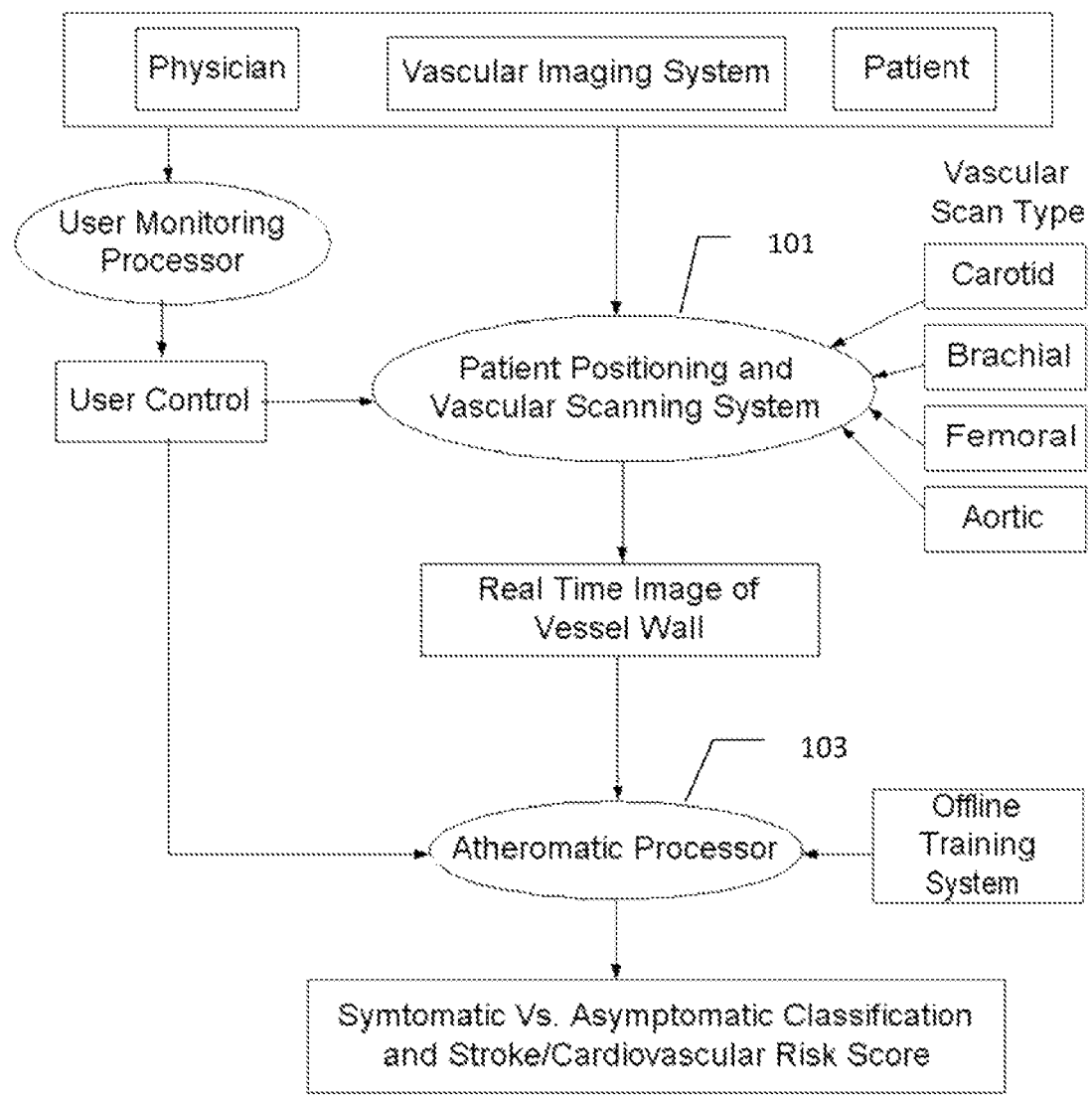
FIG. 1 shows an on-line vascular characterization system (called Atheromatic™) for classifying if the patients is "symptomatic vs. asymptomatic" along with its "cardiovascular-risk score (CVRS) score.

In the following description, for purposes of explanation, numerous specific details are set forth in order to provide a thorough understanding of the various embodiments. It will he evident, however, to one of ordinary skill in the art that the various embodiments may be practiced without these specific details.

Description of the CVRS Estimation

This section presents (a) how the plaque in the Atherosclerotic Wall Region can be classified into symptomatic vs. asymptomatic patient and (b) Cardiovascular Risk Score (CVRS) estimation.

The concept of this application lines in modeling the vessel wall region to classify the patient plaque and coming out with the cardiovascular risk score. The modeling of the vessel wall requires non-linear processing of the plaque in the vessel wall, especially the media layer. The non-linear process requires computing the features of the plaque which presents the symptomatic information and asymptomatic information. These features are characteristics of the plaque in the vessel wall such as: (a) Higher Order Spectra; (b) Discrete Wavelet Transform (DWT); (c) Texture and (d) Wall Variability. In another methodology used here is to compute the grayscale features in the Atherosclerotic Wall Region such as: Local Binary Pattern (LBP) and Laws Mask Energy (LME) and Wall Variability.

One way to classify the wall plaque is to train a system with a similar kind of features and use this trained system to identify if it can recognize a similar featured vessel and give a cardiovascular risk score. This recognition can be considered on a test ultrasound image scan having the vessel wall. This protocol can be the testing protocol on a new incoming test patient. Thus the combination of training and testing can assist in the classification of symptomatic and asymptomatic carotid vessel wall. The training system can be called as an off-line system while the testing system can be called as an on-line system. Since the training and testing systems are applied in the region-of-interest (ROI) or Guidance Zone (GZ) where the features are supposed to be extracted. Thus the region of interest can be considered as an Atherosclerotic Wall Region (AWR) and plays a critical role in development of an invention where the plaque wall features are extracted for training and the parameters computed during the training system can then be applied to the test image. The concept involves feature selection using t-test. Another novel concept is to use cross-modality information for the learning process during the training system. This means even if the symptomatic vs. asymptomatic classification system and cardiovascular risk score estimation system works for the ultrasound vascular wall, the system allows getting its training attributes from the cross-modality and it can be ultrasound, MR or CT or 3D carotid ultrasound or 3D IVUS. This idea brings a greater flexibility for development of the training system for Symptomatic vs. Asymptomatic (SymVsAsym) Classification and cardiovascular risk score (CVRS) estimation.

Since this is a vascular wall based system, it therefore requires that the far wall of the vessel wall in the longitudinal ultrasound or the region of interest or guidance zone be accurately and automatically developed. Thus an accurate determination of the media wall thickness and the grayscale region needs to be determined and analyzed. One way is to get the accurate vessel far wall is to get the initma media thickness (IMT) thickness accurately. The IMTs are normally 1 mm in thickness, which nearly corresponds to approximately 15 pixels on the screen or display. IMT estimation having a value close to 1 mm is a very challenging task in ultrasound images due to large number of variabilities such as: poor contrast, orientation of the vessels, varying thickness, sudden fading of the contrast due to change in tissue density, presence of various plaque components in the intima wall such as lipids, calcium, hemorrhage, etc. Under normal resolutions, a one mm thick media thickness is difficult to estimate using stand-alone image processing techniques. Over and above, the image processing algorithms face an even tighter challenge due to the presence of speckle distribution. The speckle distribution is different in nature from these interfaces. This is because of the structural information change between intima, media and adventitia layers of the vessel wall. As a result, the sound reflection from different cellular structures is different. The variability in tissue structure—all that happens in one mm of the vessel wall—brings fuzziness in the intensity distribution of the vessel wall. Under histology, media and adventitia walls are clearly visible and one can observe even their thicknesses. This one mm zone is hard to discern in a normal resolution image of 256×256 pixels in a region of interest (ROI) or in a higher resolution image of 512×512 pixels in a region of interest (ROI). One needs a high resolution image to process and identify the intensity gradient change in ultrasound images from lumen to intima and media to adventitia layers. The ultrasound image resolution may not be strong enough like MRI or computerized axial tomography (CAT or CT) images, which can be meaningful for soft tissue structural information display.

Thus, an on-line system can consist of Atherosclerotic Wall Region estimation using AtheroEdge™ for longitudinal Ultrasound or Athero-CTView™ for CT or Athero-MRView from MR. AtheroEdge™ is a boundary estimation system for LI and MA borders for the ultrasound longitudinal blood vessel image such as Carotid, Brachial, Femoral or Aorta. Athero-CTView™ is a boundary estimation system for computing the lumen and outer wall borders from the CT slices of the carotid artery. Similarly, Athero-MRView is the boundary estimation system for computing the lumen and outer wall borders from the MR carotid slices. Similarly, AtheroEdge3D is the boundary estimation system for computing the lumen and outer wall borders from the 3D carotid ultrasound slices.

Atherosclerotic Wall Region (AWR) is the region between LI and MA borders in the ultrasound image for the blood vessel. For CT or MR or 3D Carotid Ultrasound or 3D IVUS, the Atherosclerotic Wall Region (AWR) is considered to be the grayscale region between the lumen border and outer wall of the carotid artery.

This grayscale Atherosclerotic Wall Region (AWR) is then fed to a feature extraction processor which computes: (a) Higher Order Spectra; (b) Discrete Wavelet Transform (DWT); (c) Texture and (d) Wall Variability.

In another methodology used here is to compute the grayscale features in the Atherosclerotic Wall Region such as: Local Binary Pattern (LBP) and Laws Mask Energy (LME) and Wall Variability.

The output of the Feature Processor is fed to the Classifier which is trained off-line from the Database of similar Atherosclerotic Wall Region images. The off-line Classifier is trained from the significant features from (a) Higher Order Spectra; (b) Discrete Wavelet Transform (DWT); (c) Texture and (d) Wall Variability, selected using t-test. Symptomatic ground truth information about the training patients is drawn from cross modality imaging such as CT or MR or 3D Carotid Ultrasound or 3d IVUS in the form of 0 or 1. Support Vector Machine (SVM) supervised classifier of varying kernel functions is used off-line for training. Those skilled in the art can use: Radial Basis Probabilistic Neural Network (RBPNN), Nearest Neighbor (KNN) classifier, Decision Trees (DT), Adaboost Classifier, or of similar kind. The obtained training parameters are then used to evaluate the test set. The highest accuracy close to 90% was registered by the SVM classifier with the radial basis function kernel and the one with a polynomial kernel of order two. The system also yields the risk score value on the basis of the four set of wall features. The proposed technique demonstrates that plaque classification between symptomatic vs. asymptomatic could be achieved with a completely automated data mining CAD tool with a significant accuracy. Performance of the system is evaluated by computing the accuracy, sensitivity, specificity, and Positive Predictive Value (PPV).

Atherosclerotic Wall Region (AWR) Computation:

In the longitudinal ultrasound image, the CCA (lumen) appears as a region of low intensity between two layers of high intensity, namely, the Near Adventitia (ADN) and Far Adventitia (ADF). The Intima-Media Thickness (IMT) of the CCA is the most commonly used measure for atherosclerosis monitoring, and is defined as the distance between the Lumen-Intima (LI) and Media-Adventitia (MA) interfaces. Manual Atherosclerotic Wall Region (AWR) and measurement of IMT from B-mode images is time consuming, subjective, and difficult. In the past two decades, several CAD tools, both fully automated and semi-automated, have been developed. Typically, in CAD tools for IMT measurement, the calculation of Atherosclerotic Wall Region (AWR) computation and IMT measurement involves the following two steps.
1. Accurate recognition of the CCA, and tracing of Near Adventitia ($AD_N$) and Far Adventitia (ADO layers.
2. Segmentation of the distal CCA wall, i.e., determination of the LI and MA borders, Atherosclerotic Wall Region (AWR) computation and calculation of IMT.

Several algorithms in the literature for the automated segmentation of the CCA (image gradients and edge detection based and parametric deformable models based) rely on user interaction in Step 1 described above. Therefore, complete automation cannot he achieved and also inter-observer variability prevails.

A completely automated procedure for carotid layers extraction called CALEX (Completely Automated Layers Extraction; F. Molinari, G. Zeng, and J. S. Suri, An integrated approach to computer-based automated tracing and its validation for 200 common carotid arterial wall ultrasound images: A new technique, J Ultras Med, 29, (2010), 399-418) was developed. In another automated technique called CULEX (Completely User-independent Layers Extraction, S. Delsanto, F. Molinari, P. Giustetto, W. Liboni, S. Badalamenti, and J. S. Suri, Characterization of a Completely User-Independent Algorithm for Carotid Artery Segmentation in 2-D Ultrasound Images, Instrumentation and Measurement, IEEE Transactions on, 56(4), (2007), 1265-1274) demonstrated the usage of local statistics, signal analysis, and fuzzy-based classification for IMT measurement and subsequently for plaque delineation.

Another recent technique called CAMES (Completely Automated Multiresolution Edge Snapper; F. Molinari, C. Loizou, G. Zeng, C. Pattichis, D. Chandrashekar, M. Pantziaris, W. Liboni, A. Nicolaides, and J. Suri, *Completely Automated Multi-Resolution Edge Snapper* (CAMES)—A New Technique for an Accurate Carotid Ultrasound IMT Measurement and its Validation on a Multi-Institutional Database, in SPIE Medical Imaging Conference. 2011: Lake Buena Vista (Orlando), Fla., USA) was developed, that measures the segmentation of LI and MA borders and IMT measurement by utilizing the morphological properties of the CCA. Herein, for Step 1, we first down-sample the original image (multi-resolution approach) and then capture the (near adventitia border) ADN and far adventitia borders (ADF) edges using derivative of Gaussian Kernel with known a priori scale, and finally up-sample the determined ADF profile in order to determine the Region Of Interest (ROI) for Step 2. In Step 2, only the ROI was considered, and the First Order Absolute Moment (FOAM) operator was used to enhance the intensity edges (guided by the multiresolution approach in stage 1), and finally, the LI and MA borders were heuristically determined in this ROI. CAMES is a revolutionary technique as it is the first technique to automatically recognize the CA. This method showed 100% accuracy in artery recognition process.

Since our aim is to develop a completely automated Atherosclerotic Wall Region (AWR), CAMES was one of the preferred choice for CCA segmentation and subsequent LI and MA border determination. The system consists of an on-line system where the wall region is automatically segmented from the given set of images from database based on multi-resolution approach. The segmentation output gives LI and MA borders and the grayscale region between this the LI and MA borders constitute the Atherosclerotic Wall Region. This is called the Guidance Zone (GZ).

This grayscale information (or guidance zone, GZ) is modeled as non-linear information by taking the Radon Transform of the grayscale wall region and then computing the Normalized Bispectral Entropy and Normalized Squared Bispectral Entropy. The DWT features are computed as vertical and horizontal and energy component, in four decomposition directions corresponding to 0° (horizontal, Dh), 90° (vertical, Dv) and 45° or 135° (diagonal, Dd) orientation were taken. Texture features are also computed (symmetry and state of disorderness entropy). Finally, the vessel wall variability is computed due to presence of plaque is computed.

Once the LIMA borders are determined, one can get the Atherosclerotic Wall Region (AWR) and is ready for on-line processing of the patient's image. If the system is for CT, instead of LIMA borders, we have lumen border and outer wall border of the carotid artery. If the SysVsAsym Classification system is for MR, the protocol will compute the lumen and outer wall borders. If it is 3D Carotid Ultrasound, we have lumen border and outer wall border of the carotid artery in ultrasound cross-sectional slices. The region between the lumen and outer walls for MR or CT or 3D Ultrasound will constitute carotid artery wall thickness (CAWT). The Atherosclerotic Wall Region grayscale image is fed for feature extraction process which consists on (a) Normalized Bispectral Entropy, (b) Normalized Bispectral Squared Entropy; (c) Average Dh1, Average Dv1, Energy (from DWT coefficients); (d) Texture symmetry and Entropy; (e) Wall Variability.

Figure 38:
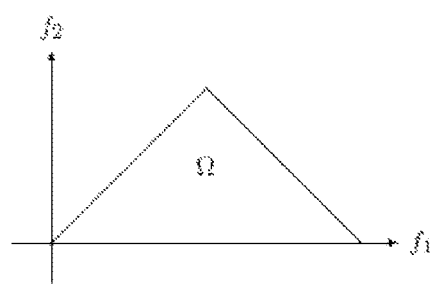
FIG. 38 shows principal domain region $\Omega$.

HOS Feature:

Higher Order Spectra or polyspectra allow one to study the non-linear behavior of a process. Higher order statistics denote higher order moments (order greater than two) and non-linear combinations of higher order moments, called the higher order cumulants. In the case of a Gaussian process, all cumulant moments of order greater than two are zero. Hence, such cumulants can be used to evaluate how much a process deviates from Gaussian behavior. One of the most commonly used HOS parameter is the bispectrum. The bispectrum is the spectrum of the third order cumulant, and is a complex valued function of two frequencies given by $$B(f_1, f_2) = E[A(f_1)X(f_2)^*X(f_2+f_2)] \quad (1)$$

where X(f) is the Fourier transform of the signal studied. As per the equation, the bispectrum is the product of the three Fourier coefficients. The function exhibits symmetry, and is computed in the non-redundant/principal domain region Ω as shown in FIG. 38.

Principal domain region (Ω) used for the computation of the bispectrum for real signals.

The bispectrum phase entropy obtained from the bispectrum is used as one of the features in this application. This entropy is defined as:

Bispectrum Phase Entropy:

$$ePRes = \sum_n p(\psi_n) \log p(\psi_n) \quad (2)$$

where $$p(\psi_n) = L^{-1} \sum_{106} l(\phi(B(f_1, f_2)) \in \psi_n) \quad (3)$$

$$\psi_n = \{\phi | -\pi + 2\pi n/N \le \phi < -\pi + 2\pi(n+1)/N\},$$

$$n = 0, 1, \ldots N-1 \quad (4)$$

where L is the number of points within the region $\Omega$, $\phi$ is the phase angle of the bispectrum, and l(.) is an indicator function which gives a value of 1 when the phase angle is within the range depicted by $\psi_n$ in equation (4).

In order to calculate the bispectrum, and hence, the phase entropy, the pre-processed ultrasound Atherosclerotic Wall Region images were first subjected to Radon transform. This transform computes line integrals along many parallel paths in the Atherosclerotic Wall Region image from different angles θ by rotating the image around its centre. Such a transformation projects the intensity of the pixels along these lines into points in the resultant transformed signal. Thus, Radon transform converts an Atherosclerotic Wall Region image into a one-dimensional signal at various angles. In this patent application, we calculated the Radon transformed signals for every 10 step size and then determined the phase entropy of these signals. Those skilled in the art can change the step size to higher and lower numbers. The system computes two bi-spectral entropies from the Radon transformed signals. These entropies are defined as follows.

Normalized Bi-spectral Entropy (e1Res):

$$e1Res = -\sum_n p_i \log p_i \quad (5)$$

where $$p_i = \frac{|B(f_1, f_2)|}{\sum_\Omega |B(f_1, f_2)|} \quad (6)$$

Normalized Bi-spectral Squared Entropy (e2Res):

$$e2Res = -\sum_n p_n \log p_n \quad (7)$$

where $$p_n = \frac{|B(f_1, f_2)|^2}{\sum_\Omega |B(f_1, f_2)|^2} \quad (8)$$

DWT Feature:

Discrete Wavelet Transform (DWT) is a transform that captures both the time and frequency information of the signal. DWT analyzes the atherosclerotic wall region image by decomposing it into coarse approximation via low-pass filtering and into detail information via high-pass filtering. Such decomposition is done recursively on the low-pass approximation coefficients obtained at each level, until the necessary iterations are reached.

Figure 39:
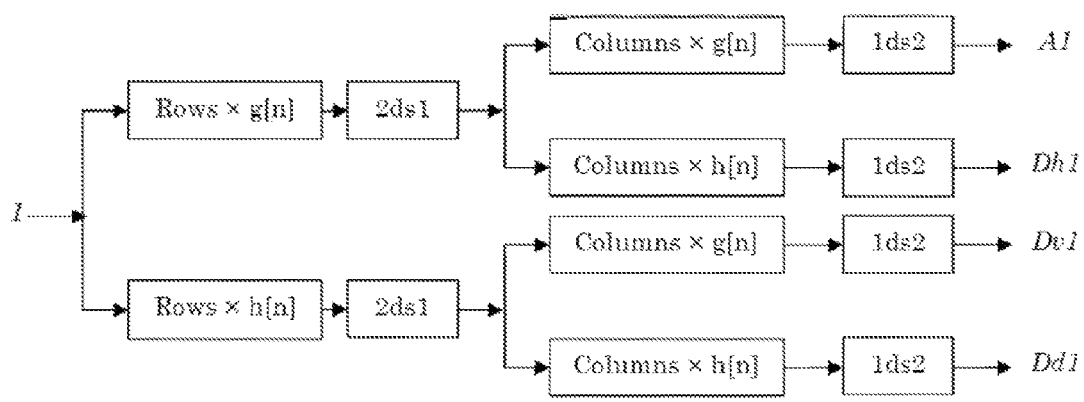
FIG. 39 shows the DWT decomposition.

Let each atherosclerotic wall region image he represented as a p×q grayscale matrix I[i,j], where each element of the matrix represents the grayscale intensity of one pixel of the image. Each non-border pixel has eight adjacent neighboring pixel intensities. These eight neighbors can be used to traverse through the matrix. The resultant 2D-DWT coefficients will be the same irrespective of whether the matrix is traversed right to left or left to right. Hence, it is sufficient that we consider four decomposition directions corresponding to 0° (horizontal, Dh), 90° (vertical, Dv) and 45° or 135° (diagonal, Dd) orientation. The decomposition structure for one level is illustrated in the diagram below. I is the image, g[n] and h[n] are the low-pass and high-pass filters, respectively and A is the approximation coefficients. In this work, the results from level 1 were found to yield significant features. FIG. 39 shows the 2D DWT decomposition. 2ds1 indicates that rows are down sampled by 2 and columns by 1. 1ds2 indicates that rows are down sampled by 1 and columns by 2. '×' operator indicates convolution operation.

As is evident from diagram above, the first level of decomposition results in four coefficient matrices, namely, A1, Dh1, Dv1, and Dd1. Since the number of elements in these matrices is high, and since we only need a single number as a representative feature, we employed averaging methods to determine such single-valued features. The following are the definitions of the three features that were determined using the DWT coefficients.

$$\text{Average } Dh1 = \frac{1}{p \times q} \sum_{x=\langle p \rangle} \sum_{y=\langle q \rangle} |Dh1(x, y)| \quad (9)$$

$$\text{Average } Dv1 = \frac{1}{p \times q} \sum_{x=\langle p \rangle} \sum_{y=\langle q \rangle} |Dv1(x, y)| \quad (10)$$

$$\text{Energy} = \frac{1}{p^2 \times q^2} \sum_{x=\langle p \rangle} \sum_{y=\langle q \rangle} (Dv1(x, y))^2 \quad (11)$$

Equations (9) and (10) calculate averages of the corresponding intensity values, whereas equation (11) is an averaging of the energy of the intensity values.

Texture Feature:

The texture of an image is characterized by the regular repletion of patterns in the image. There are several approaches to analyzing the textural properties, and in this work, we studied the statistical textural features that are based on the relationship and distribution of pixel intensities. Consider $\phi(i)$ as the number of pixels with intensity value i, i ranging from 1 to n. Let A be the area of the Atherosclerotic wall region image. The probability of intensity i in the image is given by:

$$h(i) = \frac{\varphi(i)}{A} \quad (12)$$

The standard deviation is then defined as $$\text{Deviation} = \sum_{i=1}^{n} (i - \mu)^2 h(i) \quad (13)$$

where μ is the mean of the pixel intensities.

Next, two matrices, namely, the Gray Level Co-occurrence Matrix (GLCM) and the Run Length Matrix were determined based on the pixel intensities, and features were extracted from these matrices. They are defined as follows.

Gray Level Co-occurrence Matrix:

The GLCM of an image I of size m×n is given by $$C_d = \left| \left\{ \begin{array}{l} (p,q), (p+\Delta x, q+\Delta y) : I(p,q) = i, \\ I(p+\Delta x, q+\Delta y) = j \end{array} \right\} \right| \quad (14)$$

where (p,q), (p+Δx, q+Δy) belongs to m×n, d=(Δx,Δy), and |...| denotes the set cardinality. The probability of a pixel with intensity i having a pixel with an intensity j at a distance (Δx, Δy) away is given by:

$$P_d(i,j) = \frac{C_d(i,j)}{\sum_{(i)} \sum_{(j)} C_d(i,j)} \quad (15)$$

where the summation is over all possible i and j. From equations (14) and (15), the following two features can be calculated.

$$\text{Symmetry} = 1 - \sum_i \sum_j |{}_c C_d(i,j) - {}_c C_d(j,i)| \quad (16)$$

$$\text{Entropy} = -\sum_i \sum_j P_d(i,j) \times \ln[P_d(i,j)] \quad (17)$$

Entropy, which denotes the degree of disorder in an image, will have high value if the elements in the GLCM are the same.

Run Length Matrix:

The run length matrix $P_\theta$ consists of all the elements where the intensity value i has the run length j continuous in direction θ. Typically values of θ are 0°, 45°, 90°, or 135°. The feature called Run Length Non-uniformity (RLnU) is then determined as follows.

$$RLnU = \sum_{(j)} \left( \sum_{(i)} P_\theta(i,j) \right)^2 \quad (18)$$

Since RLnU measures the similarity of the run lengths, its value will be less if the run lengths are uniform throughout the image.

LBP Feature

A circular neighborhood is considered around a pixel. 'P' points are chosen on the circumference of the circle with radius 'R' such that they are all equidistant from the center pixel. The gray values at points on the circular neighborhood that do not coincide exactly with pixel locations are estimated by interpolation. These points are then converted into a circular bit-stream of 0 s and 1 s according to whether the gray value of the point is less than or greater than the gray value of the center pixel. If the number of bit-transitions in the circular bit-stream is less than or equal to 2, the center pixel is labeled as uniform. A look up table is generally used to compute the bit-transitions to reduce computational complexity. Uniform LBP was then defined in the following manner. FIG. 42 showing the circularly symmetric neighbor sets for different P and R [2].

$$LBP_{P,R}(x) = \begin{cases} \sum_{p=0}^{P-1} s(g_p - g_c), & U(x) \leq 2 \\ P+1, & \text{otherwise} \end{cases}$$

$$s(x) = \begin{cases} 1, & x > 0 \\ 0, & x \leq 0. \end{cases}$$

$g_c$ is the gray value of the center voxel and $g_p$ is the gray value of its neighbors. U(x) is the uniformity function calculated using the method described above. Multi-Scale analysis of the image using LBP is done by choosing circles with various radii around the center pixels and thus constructing separate LBP image for each scale. For our work, energy and entropy of the LBP image, constructed over different scales are then used as feature descriptors (see FIG. 42).

Law's Mask Energy (LME) Feature

The Laws mask has evolved with the idea of representing image features without referring to the frequency domain [1]. The idea of inferring as what looks like where, instead of the conventional what happens where, is the essence of using this approach as a conjunction to the human visual perception [2]. Laws empirically determined that several masks of appropriate sizes were very informative for discriminating between different kinds of texture [3]. Originally, he classified samples based on expected values of variance-like square measures of these convolutions, called texture energy measures [3]. The texture energy measure is quantified using the three masks L3=[1, 2, 1], E3=[−1, 0, 1], and S3=[−1, 2,−1], for level, edge, and spot detection respectively. The appropriate convolution of these masks yield nine different combination of 3×3 masks, of which we use the eight zero-sum masks. The image under inspection is filtered using these eight masks, and their energies are computed and used as the feature descriptor [2].

Trace Transform (TT) Feature

Trace transform is a generalized approach to the Radon transform, and consists of tracing an image with straight lines along which certain functional of the image function. The purpose of a functional is to characterize a function by a number. Different functionals are used for representation of rotation, translation and scaling invariant features of an image, construction of features that may correlate well with the visual texture (A. Kadyrov, and M. Petrou, "The trace transform and its applications," *IEEE Trans. Pattern Anal., Machine Intel.*, vol. 23, no. 8, pp. 811-828, August 2001). Let the studied image be scanned with lines in all directions. Let A be the set of all these lines. The Trace transform can then be defined as a function g defined on Δ with the help of T which is some functional of the image function of variable t. T is called the trace functional. In order to define a triple feature, two more functionals designated by letters P and Φ are defined. P, called the diametrical functional, is a functional of the Trace transform function when it is considered as a function of the length of the normal to the line only. Φ, called the circus functional, is a functional operating on the orientation variable, after the previous two operations (use of T and P) have been performed. Thus, the triple feature can be defined as $$\Pi(F,C_1) = \Phi(P(T(F(C_1;\Phi;p;t)))) \quad \text{(TT-1)}$$

where $F(C_1;\Phi;p;t)$ indicates the values of the image function along the chosen line. $C_1$ is the co-ordinate system parameterized by (Φ;p;t). We calculate two triple features using the invariant functionals defined as follows:

$$\Pi_1 = (T \to IF_1, P \to IF_2, \Phi \to IF_3) \tag{TT-2}$$

$$\Pi_2 = (T \to IF_3, P \to IP_2, \Phi \to IF_1) \tag{TT-3}$$

where $\Pi_1$ is the normalized version of the triple feature formed by using $IF_1$, $IF_2$, and $IF_3$ for functionals T, P, and Φ respectively in Eq. (1). $\Pi_2$ is the normalized version of the triple feature formed by using $IF_3$, $IF_2$, and $IF_1$ for functionals T, P, and Φ respectively in Eq. (1). $\Pi_1$ and $\Pi_2$ are the rotation, scale and translation invariant texture features that were used to quantify visual texture measure in our application.

Fuzzy Grayscale Level Co-occurrence Matrix (FGLCM) Feature

Gray Level Co-occurrence Matrix (GLCM) represents second-order texture moments, and it is made up of the frequency of appearance of a gray level in a specified linear relationship with another gray level within the neighborhood of interest. The Fuzzy GLCM (FGLCM) [24] of an image I of size L×L is given by:

$$F_d(m,n) = [f_{mn}]_{L \times L} \tag{F-4}$$

where $f_{mn}$ corresponds to the frequency of occurrence of a gray-value 'around m' separated from another pixel, with gray-value 'around n', by a distance d in a specific direction θ. It is represented as F=f (I,d,θ).

In this study, we used rotational invariant co-occurrence matrix F', obtained by averaging the four symmetrical fuzzy co-occurrence matrices computed with θ=0°, 45°, 90°, 135° and d=20, to find the texture feature value. The pyramidal membership function $\mu_{\tilde{m}I(x,y),\tilde{n}I(x,y\pm d)}$ used to build these matrices has a support of 11×11 pixels. Here, μ represents fuzzy membership distribution of gray values around 'm' and 'n'. Given F', it is normalized to obtain $F_{norm}$ which gives the joint probability of occurrence of one pixel having gray-value 'around m' with another pixel separated by a defined spatial relationship and having gray-value 'around n'. Based on the above-mentioned, we obtain the following FGLCM based features:

$$\text{Energy: } E_{fuzzy} = \sum_m \sum_n [F_d(m,n)]^2 \tag{F-5}$$

$$\text{Contrast: } C_{fuzzy} = \sum_m \sum_n (m-n)^2 F_d(m,n) \tag{F-6}$$

$$\text{Homogeneity: } G_{fuzzy} \sum_m \sum_n \frac{F_d(m,n)}{1+(m-n)^2} \tag{F-7}$$

$$\text{Entropy: } H_{fuzzy} = -\sum_m \sum_n F_d(m,n) \cdot \ln F_d(m,n) \tag{F-8}$$

$$\text{Correlation: } \text{Corr}_{fuzzy} = \frac{\sum_m \sum_n [mn F_d(m,n)] - \mu_m \mu_n}{\sigma_m \sigma_n} \tag{F-9}$$

where $$\mu_m = \sum m F_d(m,n), \sigma_m^2 = \sum m^2 F_d(m,n) - \mu_m^2 \tag{F-10}$$

$$\mu_n = \sum n F_d(m,n), \sigma_n^2 = \sum n^2 F_d(m,n) - \mu_n^2 \tag{F-11}$$

Moments $M_1$, $M_2$, $M_3$, and $M_4$:

$$M^g_{fuzzy} = \sum_m \sum_n (m-n)^g F_d(m,n) \tag{F-12}$$

The similarity between two pixels that are (Δm,Δn) apart is measured by the homogeneity feature. On the contrary, the local variation between those two pixels is captured by the contrast feature. The denseness and the degree of disorder in an image are measured by energy and entropy features. The entropy feature will have a maximum value when all elements of the co-occurrence matrix are the same. Difference statistics is defined as "the distribution of the probability that the gray-level difference is k between the points separated by δ in an image" (F. Tomita and S. Tsuji, *Computer analysis of visual textures*. Kluwer Academic Publishers, Boston, 1990). The difference statistics vector being a subset of the fuzzy co-occurrence matrix can be obtained from FGLCM as:

$$F_\delta(k) = \sum_{\substack{m \ n \\ |m-n|=k}} \sum F_d(m,n) \tag{F-13}$$

where k=0, 1 ... c−1, c is the number of gray scale levels [26], and δ is d=(Δm,Δn). Based on the acquired vector, we obtain the following difference statistics based features (J. S. Weszka and A. Rosenfield, "An application of texture analysis to material inspection," *Pattern Recogn.*, vol. 8, no. 4, pp.195-200, 1976):

$$\text{Angular Second Moment: } ASM_{diff} = \sum_{k=0}^{c-1} F_\delta(k)^2 \tag{F-14}$$

When the $F_\delta(k)$ values are very similar or close, ASM is small. ASM is large when certain values are high and others are low.

$$\text{Mean: } \mu_{diff} = \sum_{k=0}^{c-1} k F_\delta(k) \tag{F-15}$$

When $F_\delta(k)$ values are concentrated near the origin, mean is small and mean is large when they are far from the origin.

$$\text{Contrast: } C_{diff} = \sum_{k=1}^{c-1} k^2 F_\delta(k) \tag{F-16}$$

Contrast is also known as the second moment of $F_\delta$ (its moment of inertia about the origin).

$$\text{Entropy: } H_{diff} = -\sum_{k=0}^{c-1} F_\delta(k) \log F_\delta(k) \quad \text{(F-17)}$$

Entropy is smallest when $F_\delta(k)$ values are unequal, and largest when $F_\delta(k)$ values are equal. Entropy is directly proportional to unpredictability.

The above mentioned features were calculated for $\delta=(0, 1)$, $(1, 1)$, and $(1, 0)$, and the total mean values for the four features were taken.

The FGLCM contains information about the positions of pixels having similar gray level values, and hence, the features in Eqns. (F-5 to F-12) quantify this information. However, the difference statistics based features (Eqns. F-13 to Eqns. F-17)) are derived from the vector based on absolute differences between pairs of gray levels. Even though the definitions of features like contrast (Eq. (F-6) and Eq. (F-16)) and entropy (Eq. (F-8) and Eq. (F-17)) are similar, they are calculated on different matrices/vectors that quantify the texture of the image in different ways.

Fuzzy Run Length Matrix (FRLM)

The run length matrix, $F_\theta(m,n)$ consists of the number of elements where gray level value i has the run length j continuous in direction $\theta$. Often the direction $\theta$ is set as 0°, 45°, 90°, and 135° (M. M. Galloway, "Texture analysis using gray level run lengths," *Comput. Graphics Image Process.*, vol. 4, no. 2, pp. 172-179, 1975 and K. V. Ramana and B. Ramamoorthy, "Statistical methods to compare the texture features of machined surfaces," *Pattern Recogn.*, vol. 29, pp. 1447-1459, 1996). The features listed below were calculated for analysis and classification:

Fuzzy Short Run Emphasis:

$$SRE_{fuzzy} = \sum_m \sum_n \frac{F_\theta(m,n)}{n^2} \bigg/ \sum_m \sum_n F_\theta(m,n) \quad \text{(F-18)}$$

Fuzzy Long Run Emphasis:

$$LRE_{fuzzy} = \sum_m \sum_n n^2 F_\theta(m,n) \bigg/ \sum_m \sum_n F_\theta(m,n) \quad \text{(F-19)}$$

Fuzzy Gray Level Non-Uniformity:

$$GLNU_{fuzzy} = \sum_m \left\{ \sum_n F_\theta(m,n) \right\}^2 \bigg/ \sum_m \sum_n F_\theta(m,n) \quad \text{(F-20)}$$

Fuzzy Run Length Non-Uniformity:

$$RLNU_{fuzzy} = \sum_n \left\{ \sum_m F_\theta(m,n) \right\}^2 \bigg/ \sum_m \sum_n F_\theta(m,n) \quad \text{(F-21)}$$

Fuzzy Run Percentage:

$$RP_{fuzzy} = \sum_m \sum_n F_q(m,n) / A \quad \text{(F-22)}$$

where A is the area of the image of interest.

Wall Variability (WV):

This is computed by measuring the standard deviation of the IMT from the longitudinal ultrasound image. As mentioned in the previous section, AtheroEdge™ algorithm was employed to determine the LI and MA borders. In order to calculate the distance between LI and MA borders (IMT), the Polyline Distance Measure (PDM) was used. PDM is based on vector calculus, and in this method, we measure the distance of each vertex of one boundary to the segments of the second boundary.

Consider two boundaries $B_1$ and $B_2$ that represents LI and MA borders. The distance $d(v,s)$ between a vertex $v=(x_0, y_0)$ on the $B_1$ and a segment s formed by the endpoints $v_1=(x_1, y_1)$ and $v_2=(x_2, y_2)$ on $B_2$ can be defined as:

$$d(v, s) = \begin{cases} d_\perp & 0 \le \lambda \le 1 \\ \min\{d_1, d_2\} & \lambda < 0, \lambda > 1 \end{cases} \quad (19)$$

where $d_1$ and $d_2$ are the Euclidean distances between the vertex v and the endpoints of segment s; $\lambda$ is the distance along the vector of the segment s; $d_\perp$ is the perpendicular distance between v and the segment s.

The polyline distance from vertex v to the boundary $B_2$ can be defined as $$d(v, B_2) = \min_{v \in B_2}\{d(v, s)\}.$$

The distance between the vertexes of $B_1$ to the segments of $B_2$ is defined as the sum of the distances from the vertexes of $B_1$ to the closest segment of $B_2$:

$$d(B_1, B_2) = \sum_{v \in B_1} d(v, B_2) \quad (20)$$

Similarly, $d(B_2, B_1)$, which is the distance between the vertices of $B_2$ to the closest segment of $B_1$, can be calculated by simply swapping the boundaries. The polyline distance between boundaries is the defined as:

$$D(B_1, B_2) = \frac{d(B_1, B_2) + d(B_2, B_1)}{(\text{\# of vertices of } B_1 + \text{\# of vertices of } B_2)} \quad 21)$$

When $B_1$ is taken to be the LI boundary, and $B_2$ the MA boundary, the resultant $D(B_1, B_2)$ is called the IMT measure. The variability in the distance measurements can be computed as:

$$\sigma^2(B_1, B_2) = \sum_{v \in B_1} (d(v, B_2) - d(B_1, B_2))^2 \quad (22$$

-continued $$\sigma^2(B_2, B_1) = \sum_{v \in B_2} (d(v, B_1) - d(B_2, B_1))^2 \quad (23)$$

and the $WV_{poly}$ (also called as IMTVpoly since it is the variability of the IMT and computed using polyline method) can be determined using the following equation.

$$IMTV_{poly} = \sqrt{\frac{\sigma^2(B_1, B_2) + \sigma^2(B_2, B_1)}{\# \text{ vertices of } B_1 + \# \text{ vertices of } B_2}} \quad (24)$$

The key advantage of using PDM over other IMT measurement techniques is that the measured distance is robust because it is independent of the number of points on each boundary. More details on the centerline vs. polyline will be discussed ahead. This variability is the wall thickness variability in MR or CT or 3D carotid Ultrasound or 3D IVUS.

In the various embodiments described herein, a CAD system for symptomatic vs. Asymptomatic patient image classification and computing the cardiovascular risk score based on the grayscale features of atherosclerotic wall. The image classification is a training-based system using cross-modality a priori knowledge binary information for training the classifier off-line. The on-line system consists of Atherosclerotic Wall Region estimation using AtheroEdge™ for longitudinal Ultrasound (or Athero-CTView™ for CT) or (Athero-MR-View for MR) or AtheroEdge3D (for 3D carotid Ultrasound). This grayscale Wall Region is then fed to a feature extraction processor which computes features using: (a) Higher Order Spectra; (b) Discrete Wavelet Transform (DWT); (c) Texture and (d) Wall Variability. In another methodology used here is to compute the grayscale features in the Atherosclerotic Wall Region such as: Local Binary Pattern (LBP) and Laws Mask Energy (LME) and Wall Variability.

The output of the Feature Processor is fed to the Classifier which is trained off-line from the database of similar Atherosclerotic Wall Region images. The off-line Classifier is trained from the significant features from (a) Higher Order Spectra; (b) Discrete Wavelet Transform (DWT); (c) Texture and (d) Wall Variability, selected using t-test. Symptomatic ground truth information about the training patients is drawn from cross modality imaging such as CT or MR or 3D carotid ultrasound or 3D IVUS in the form of binary information such as 0 or 1. Support Vector Machine (SVM) supervised classifier of varying kernel functions is used off-line for training. The obtained training parameters are then used to evaluate the test set. The system also yields the risk score value on the basis of the four set of wall features. The proposed technique demonstrates that plaque classification between symptomatic vs. asymptomatic could be achieved with a completely automated CAD tool with a significant accuracy. Performance of the system is evaluated by computing the accuracy, sensitivity, specificity, and Positive Predictive Value (PPV).

FIG. 1 shows an on-line vascular characterization system (called Atheromatic™) for classifying if the patients is "symptomatic vs. asymptomatic" along with its "cardiovascular-risk score (CVRS) score. The main processor is the Atheromatic™ (classification system for symptomatic vs. asymptomatic patient images) demonstrated for real time longitudinal ultrasound imaging system. Though this system is developed for the carotid vascular wall, but this art can be easily transformed to Brachial, Femoral and Aortic Arteries and claimed for. This art of Atheromatic™ can also be extending to MRI or CT or 3D carotid ultrasound or 3D IVUS wall images. The input to the Atheromatic™ processor is Off-line training system. The user has full control on the real time Atheromatic™ system at any time during image acquisition and running the Atheromatic™ software for classification of the plaque image between symptomatic and asymptomatic classification. The input to the system is any vascular scanning system such as for Carotid, Brachial, Femoral or Aorta. The important point to note is that if input to the Atheromatic™ system is an ultrasound longitudinal image, then off-line training system must be trained on longitudinal ultrasound images, but the ground truth binary information used for training the classifier can be derived from CT or MRI or 3D Carotid Ultrasound or longitudinal Ultrasound or 3D Intravascular Ultrasound (IVUS). Similarly, if the input image is a MR image, then off-line training system must be trained on MR images, and the ground truth binary information used for training the classifier can be derived from CT or MRI or longitudinal Ultrasound or 3D carotid Ultrasound or IVUS. Similarly, if the input image is a CT image, then off-line training system must be trained on CT images, and the ground truth binary information for training the classifier can be derived from CT or MRI or Ultrasound or IVUS. Similarly, if the input image is a 3D Ultrasound image, then off-line training system must be trained on 3D Ultrasound images, and the ground truth binary information for training the classifier can be derived from CT or MRI or 3D Carotid Ultrasound or IVUS. Similarly, if the input image is for Brachial, Femoral or Aorta, then off-line training system must be trained on Brachial, Femoral or Aorta, and the ground truth binary information for training the classifier can be derived from CT or MRI or 3D Carotid Ultrasound or IVUS.

Thus the overall system (off-line and on-line) is flexible for any of the three imaging modalities: Ultrasound, CT, MR, while the binary information used for training the off-line classifier can be any. The off-line system must be trained on the same system on which the on-line operates, while the binary information used for training the off-line system can be derived from any sources such as longitudinal Ultrasound, or 3D ultrasound or MR or CT.

Figure 2:
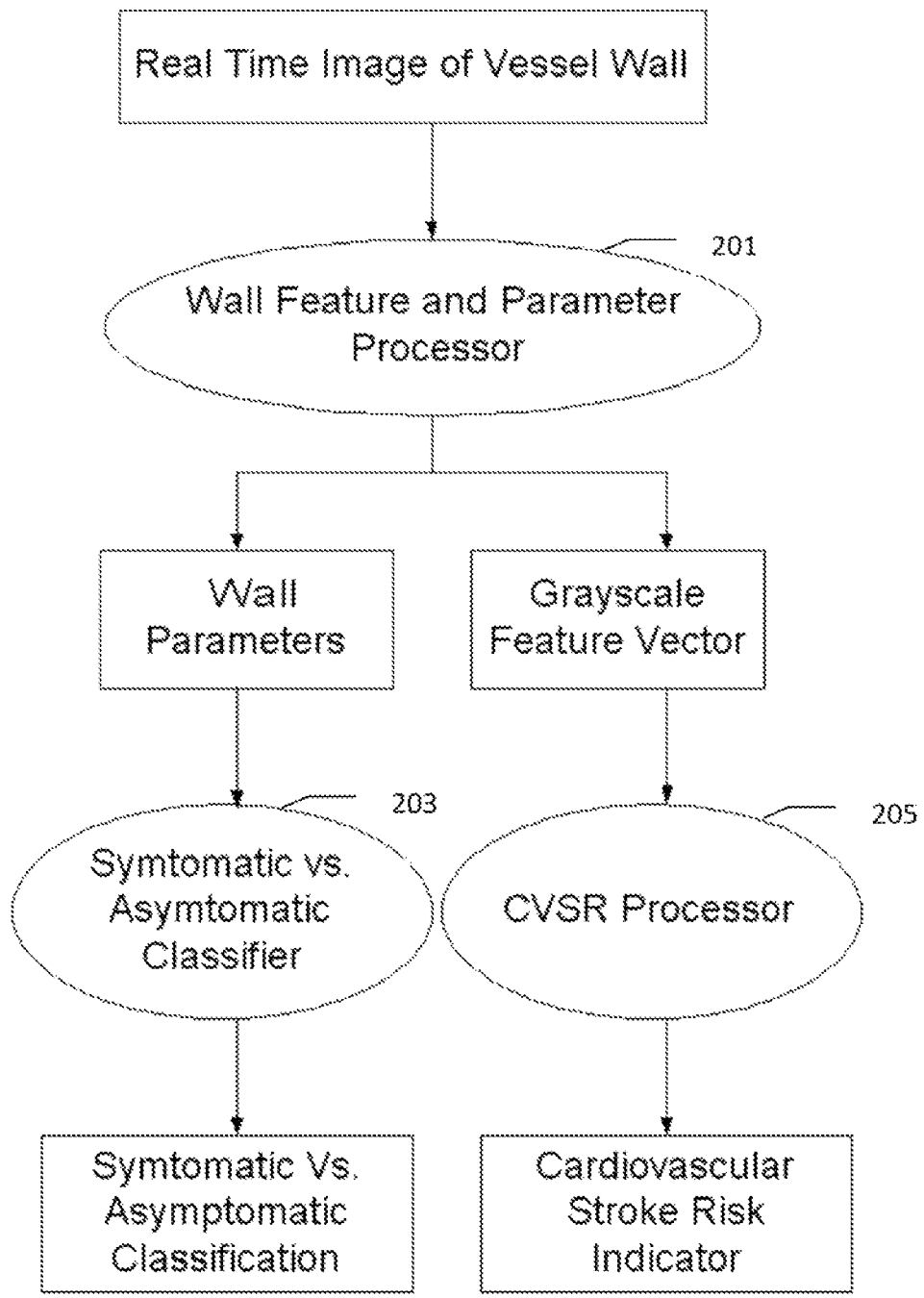
FIG. 2 shows on-line Atheromatic™ Processor which consists of three processors: (a) on-line Wall feature and parameter processor; (b) Symptomatic vs. Asymptomatic Processor and (c) Cardiovascular Risk score Processor.

FIG. 2 shows on-line Atheromatic™ processor which consists of three processors: (a) on-line Wall feature and parameter Processor; (b) Symptomatic vs. Asymptomatic Processor and (c) Cardiovascular Risk score Processor. Wall Feature Processor is used for computing the grayscale features given the on-line input test image of an ultrasound image. If the overall system (in-line and off-line systems) are MR-based, then the grayscale features are computed on the MRI wall region image. If the overall system (in-line and off-line systems) are CT-based, then the grayscale features are computed on the CT wall region image. If the overall system (in-line and off-line systems) are 3D ultrasound-based, then the grayscale features are computed on the Ultrasound cross-section wall region image. It is the carotid artery wall thickness (CAWT) which is estimated first as the region of interest instead of Atherosclerotic Wall Region (AWR). The on-line Atheromatic™ classifier is then applied with the input grayscale features. The CVRS (Cardiovascular Risk Score) Processor is then applied once the grayscale features are estimated. The output is the Cardiovascular Score Risk Indicator.

Figure 3:
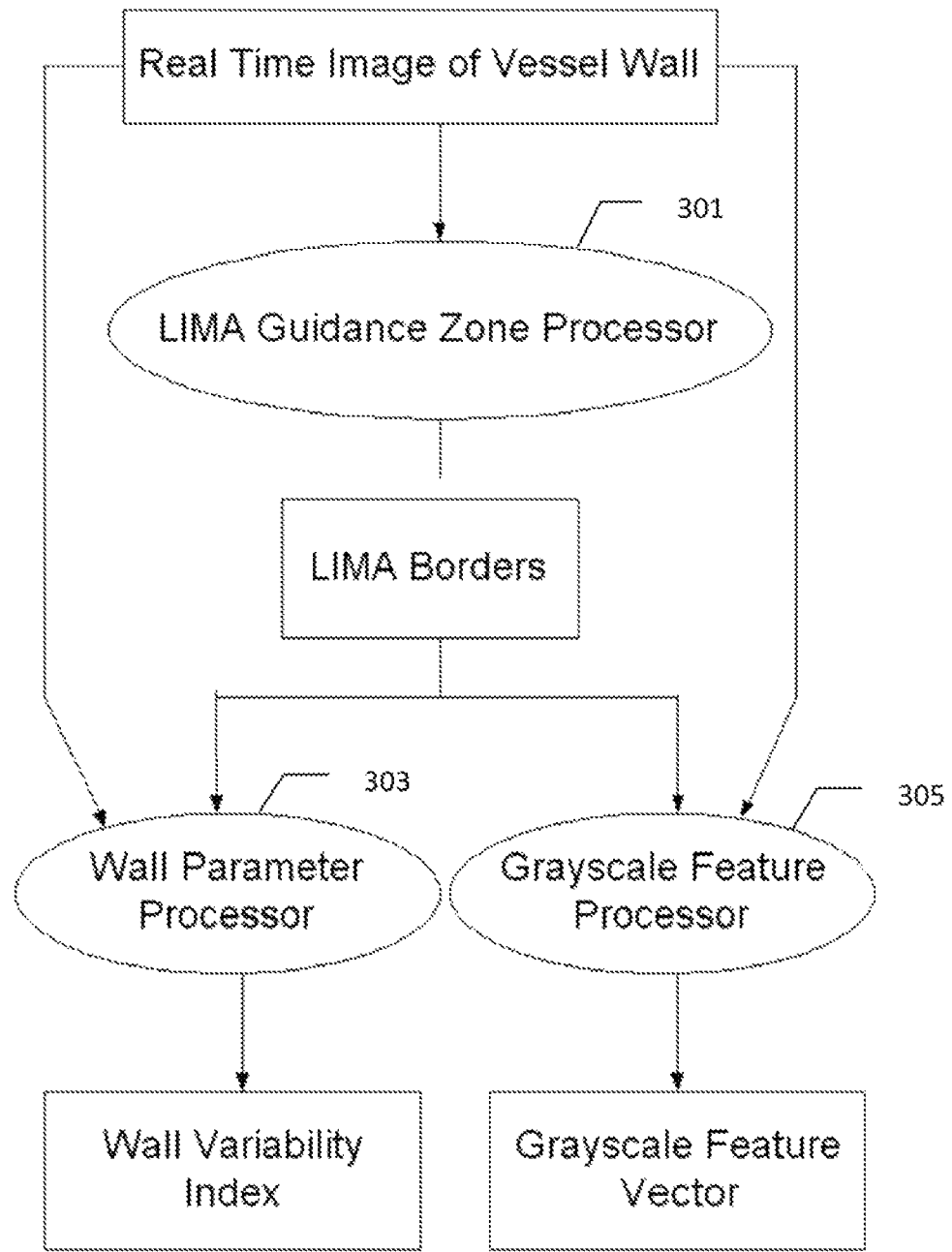
FIG. 3 shows the grayscale Wall Feature Processor which consists of (a) LIMA processor; (b) Wall Variability Processor and (c) Grayscale Feature Processor.

FIG. 3 shows the grayscale on-line Wall Feature processor which consists of: (a) LIMA processor; (b) Wall Variability Processor and (c) Grayscale Feature Processor. The LIMA processor finds the Lumen-Intima (LI) border and Media-Adventitia (MA) borders. The process takes an input real time ultrasound image and finds the LIMA border and corresponding grayscale region inside the LIMA border. The grayscale region is subjected to Grayscale Feature extraction using Grayscale Feature Processor and the LIMA borders are subjected to Wall Variability using Wall Variability Processor. The wall variability is a significance indicator about the extensiveness of the variability of the changes in the media layer where the plaque deposition starts early in the walls. This variability figure can be computed using several methods such as middle line method, polyline distance methods, distance transform methods, variation method or manual methods. The grayscale feature Processor computes grayscale features based on: (a) Higher Order Spectra; (b) Discrete Wavelet Transform (DWT); and (c) Texture. Those skilled in the art can also use Fuzzy methods for feature extraction.

Figure 4:
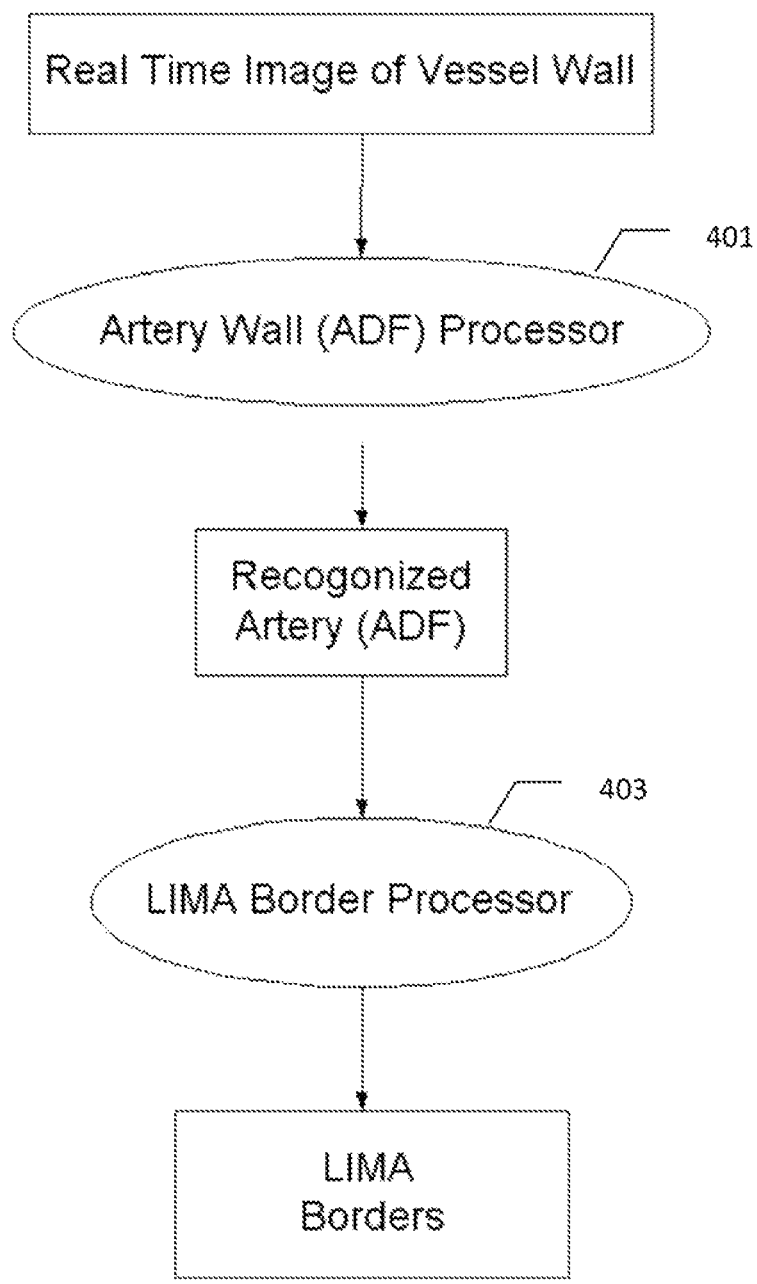
FIG. 4 shows the LIMA Processor. This consists of two processors: (a) Artery recognition Processor and (b) LIMA border Processor.

FIG. 4 shows the LIMA processor for the on-line process. This consists of two processors: (a) Artery recognition processor (ARP) and (b) LIMA border processor. Artery recognition processor is used for recognition of the far wall of the artery in the image frame. Since the image frame has Jugular vein and CCA artery, the ARP automatically identifies the far wall of the CCA. The same method is applicable to Brachial, Femoral or Aortic Arteries when dealing with ultrasound images. The output of the ARP is the ADF (far adventitia) border. The LIMA border processor inputs the grayscale image and the ADF border and the output is the LIMA borders. The LIMA border consists of LI and MA borders. This the list of coordinates (x,y) for the LI and list of coordinates (x,y) for the MA border. These borders are then fitted with spines or higher order polynomials for smoothing.

Figure 5:
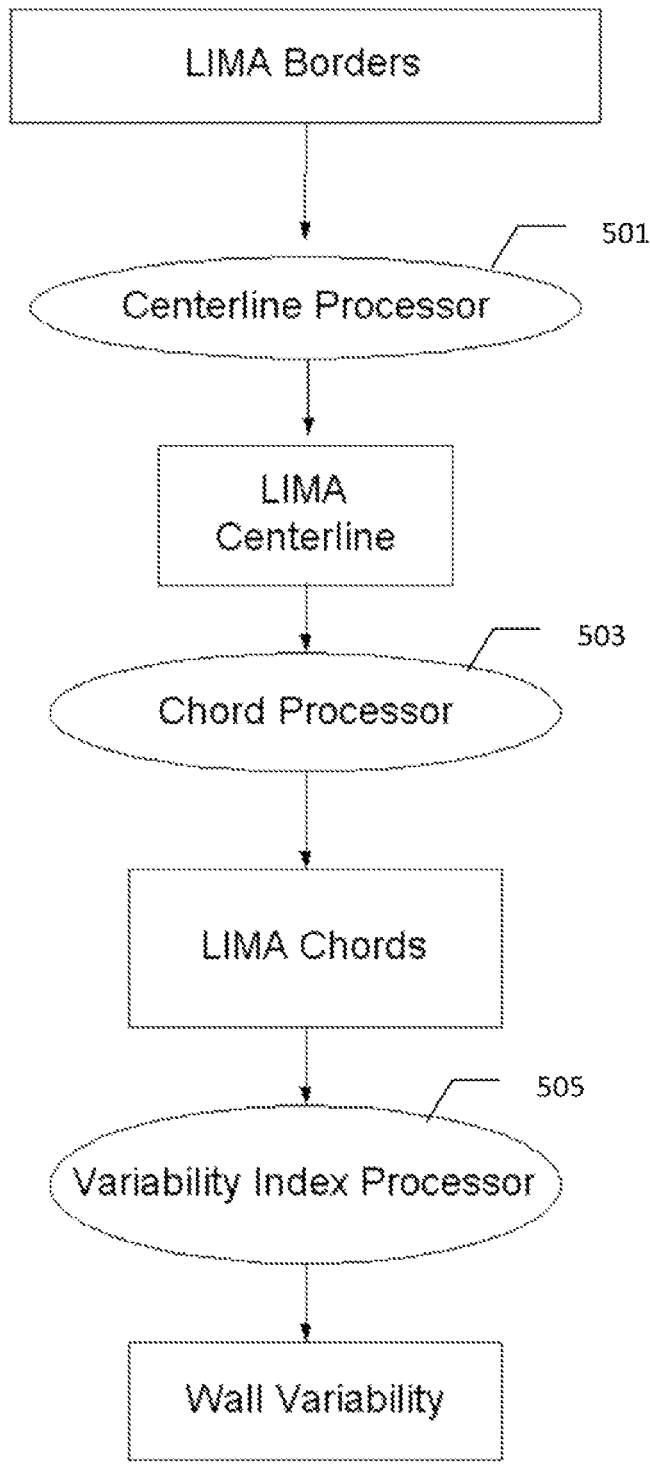
FIG. 5 shows the wall variability Processor. It consists of (a) Middle line Processor, (b) Chord Processor and (c) Variability Index Processor.

FIG. 5 shows the wall variability processor for the on-line system. It consists of (a) Middle line Processor, (b) Chord Processor and (c) Variability Index Processor. This processor gets its inputs from the LIMA processor, which consists of (x,y) list of coordinates. The processor can compute the middle line of the LIMA borders, the middle line chords of the vessel wall borders and it variability index. The middle line borders are the set of list of (x,y) coordinates which are exactly middle between the LI and MA borders. Chord processor helps in computing the perpendicular lines along the arterial vessel wall between the LI and MA borders. For the MR, CT, 3D carotid ultrasound and 3D IVUS, the middle line is set of points which are equal distance from lumen border and outer wall border. This variability indicator for longitudinal ultrasound (or for MR, CT, 3D Carotid Ultrasound and 3D IVUS) is critical in computing the feature vector for the on-line test image. Feature vector is computed as a combination of grayscale features and the wall variability. This includes: (a) Higher Order Spectra; (b) Discrete Wavelet Transform (DWT); and (c) Texture and (d) wall variability.

Figure 6A:
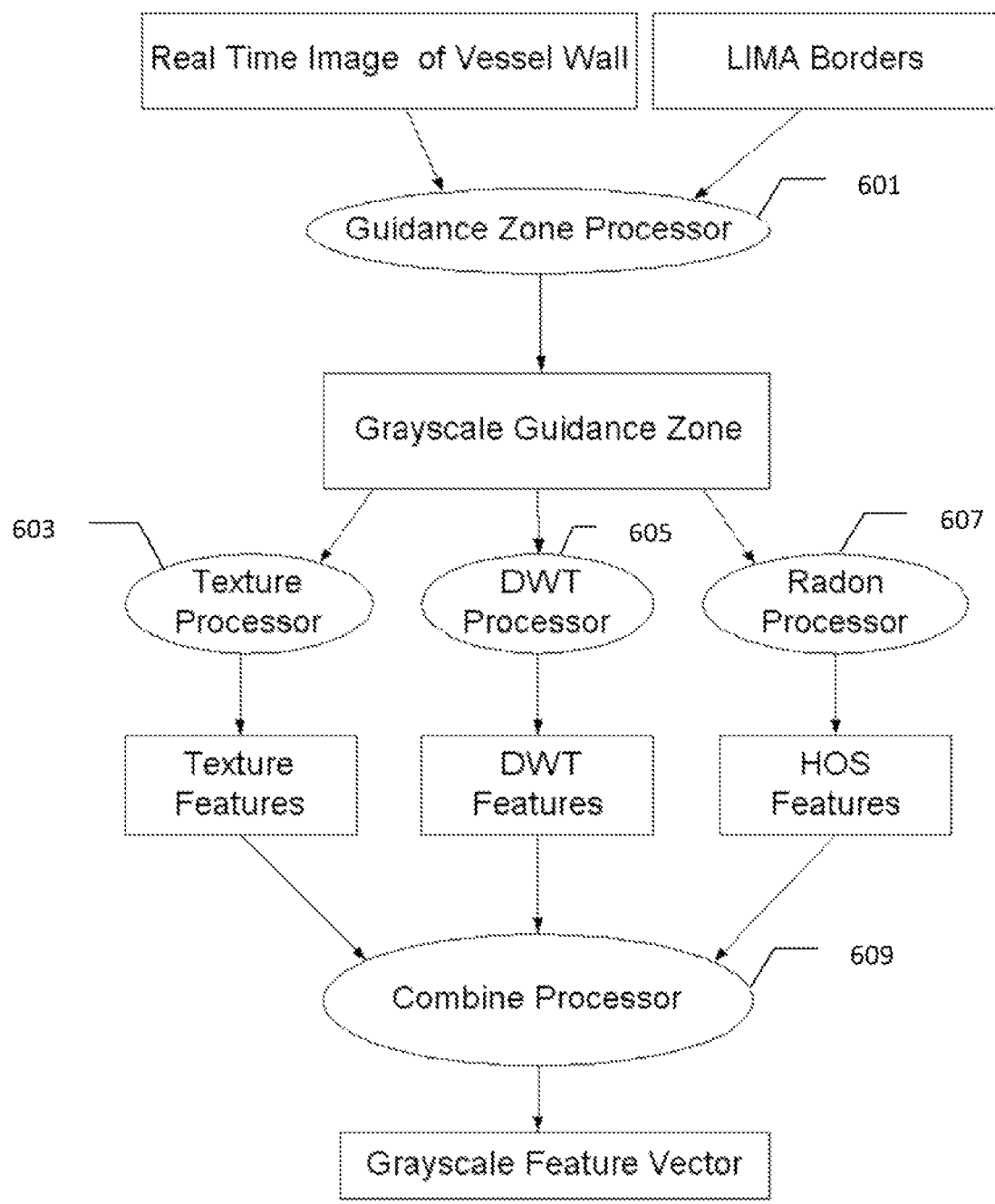
FIG. 6A shows the Grayscale Feature Processor which consists of (a) Texture Processor; (b) DWT Processor and (c) Radon Processor.

FIG. 6A shows the Grayscale on-line Feature Processor which consists of: (a) Texture Processor; (b) DWT Processor and (c) Radon Processor and (d) Combine Processor. Once the Guidance zone is computed using the LIMA borders (output of the LIMA processor), the on-line system runs the feature extraction process there by computing the grayscale features. These features are then combined to get an output using the Combined Processor. Texture Processor computes the texture features, DWT Processor computes the discrete wavelet transform features and radon processor computes the higher order spectra features for the walls. Combine processor combines all these grayscale features along with the wall variability features yielding the combined features. For the MR, CT, 3D carotid ultrasound and 3D IVUS, once the arterial wall thickness region is computed, feature processor is applied for feature computation. This consists of texture features, DWT features, higher order spectra features (using radon processor), which are then combined using combine processor.

Figure 6B:
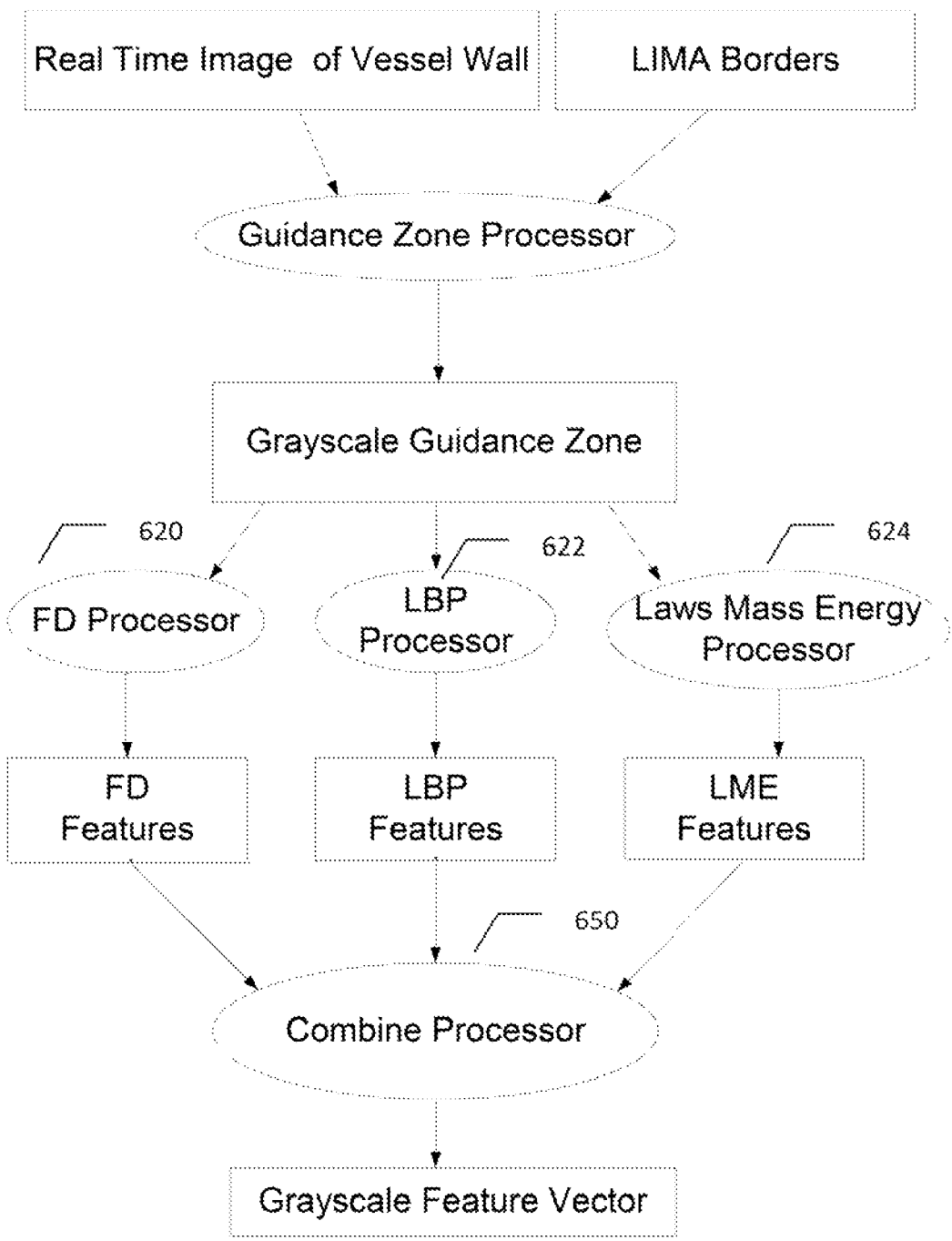
FIG. 6B shows the Grayscale Feature Processor which consists of (a) Local Binary Pattern (LBP) Processor and (b) Law's Mask Energy (LME) Processor.

FIG. 6B shows the Grayscale on-line Feature Processor which consists of: (a) Fractal Dimension Processor; (b) LBP Processor and (c) LME Processor and (d) Combine Processor. Once the Guidance zone is computed using the LIMA borders (output of the LIMA processor), the on-line system runs the feature extraction process there by computing the grayscale features. These features are then combined to get an output using the Combined Processor. Fractal Processor computes the fractal features, LBP Processor computes the local binary pattern features and LME processor computes the Law's Mass Energy features for the walls. Combine processor combines all these grayscale features along with the wall variability features yielding the combined features. For the MR, CT, 3D carotid ultrasound and 3D IVUS, once the arterial wall thickness region is computed, feature processor is applied for feature computation. This consists of fractal features, LBP features and LME features, which are then combined using combine processor.

Figure 6C:
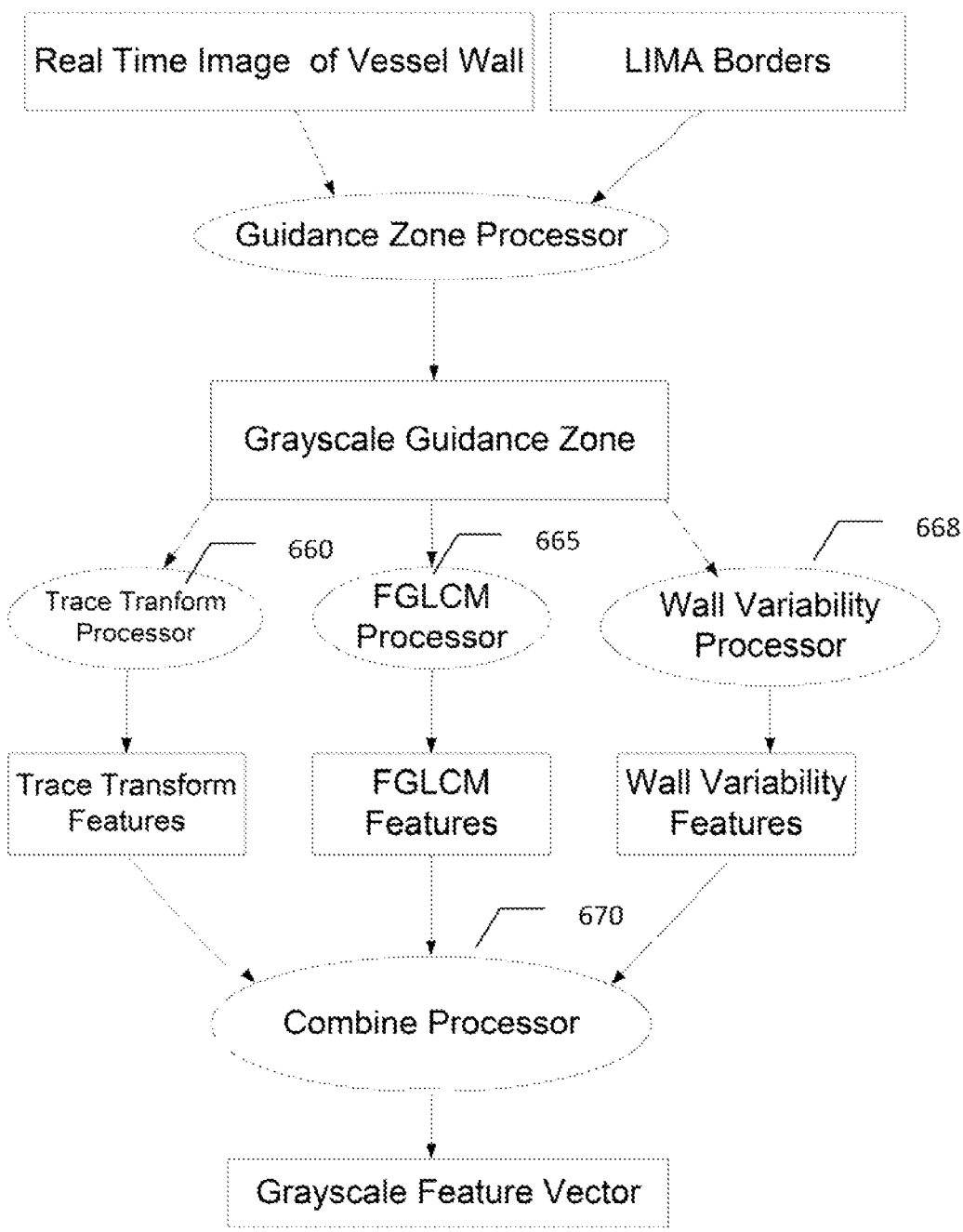
FIG. 6C shows the Grayscale Feature Processor which consists of: (a) Trace Transform (TT) Processor and (b) Fuzzy Grayscale Level Co-occurrence Matrix (FGLCM) Processor and Wall Variability Process

FIG. 6C shows the Grayscale on-line Feature Processor which consists of: (a) Trace Transform Processor; (b) Fuzzy GLCM Processor and (c) Wall Variability Processor and (d) Combine Processor. Once the Guidance zone is computed using the LIMA borders (output of the LIMA processor), the on-line system runs the feature extraction process there by computing the grayscale features. These features are then combined to get an output using the Combined Processor. Trace Transform Processor computes the trace functional features, Fuzzy GLCM Processor computes the Fuzzy Pattern features and Wall Variability processor computes the Wall features for the walls. Combine processor combines all these grayscale features along with the wall variability features yielding the combined features. For the MR, CT, 3D carotid ultrasound and 3D IVUS, once the arterial wall thickness region is computed, feature processor is applied for feature computation. This consists of Trace Transform Features, Fuzzy GLCM Features and Wall Variability Features, which are then combined using combine processor.

On-line HOS Processor:

Higher Order Spectra or polyspectra allow one to study the non-linear behavior of a process. Higher order statistics denote higher order moments (order greater than two) and non-linear combinations of higher order moments, called the higher order cumulants. In the case of a Gaussian process, all cumulant moments of order greater than two are zero. Hence, such cumulants can be used to evaluate how much a process deviates from Gaussian behavior. One of the most commonly used HOS parameter is the bispectrum. The bispectrum is the spectrum of the third order cumulant, and is a complex valued function of two frequencies given by the following equation:

$$B(f_1, f_2) = E[A(f_1)X(f_2)^* X(f_2 + f_2)] \quad (I)$$

where X(f) is the Fourier transform of the signal studied. As per the equation, the bispectrum is the product of the three Fourier coefficients. The function exhibits symmetry, and is computed in the non-redundant/principal domain region $\Omega$ as shown in FIG. 39.

Principal domain region ($\Omega$) used for the computation of the bispectrum for real signals.

The bispectrum phase entropy obtained from the bispectrum is used as one of the features in this application. This entropy is defined as:

Bispectrum Phase Entropy:

$$ePRes = \sum_n p(\psi_n) \log p(\psi_n) \quad (2)$$

where $$p(\psi_n) = L^{-1} \sum_{106} l(\phi(B(f_1, f_2)) \in \psi_n) \quad (3)$$

$$\psi_n = \{\phi | -\pi + 2\pi n/N \leq \phi < -\pi + 2\pi(n+1)/N\},$$

$$n = 0, 1, \ldots N-1 \quad (4)$$

where L is the number of points within the region $\Omega$, $\phi$ is the phase angle of the bispectrum, and l(.) is an indicator function which gives a value of 1 when the phase angle is within the range depicted by $\psi_n$ in equation (4).

In order to calculate the bispectrum, and hence, the phase entropy, the pre-processed ultrasound plaque region images were first subjected to Radon transform. This transform computes line integrals along many parallel paths in the image from different angles $\theta$ by rotating the image around its centre. Such a transformation projects the intensity of the pixels along these lines into points in the resultant transformed signal. Thus, Radon transform converts an image into a one-dimensional signal at various angles. In this study, we calculated the Radon transformed signals for every 1° step size and then determined the phase entropy of these signals. The system computes two bi-spectral entropies from the Radon transformed signals. These entropies are defined as follows.

Normalized Bi-spectral Entropy (e1Res):

$$e1\ Res = -\sum_n p_i \log p_i \quad (5)$$

where $$p_i = \frac{|B(f_1, f_2)|}{\sum_\Omega |B(f_1, f_2)|} \quad (6)$$

Normalized Bi-spectral Squared Entropy (e2Res):

$$e2\ Res = -\sum_n p_n \log p_n \quad (7)$$

where $$p_n = \frac{|B(f_1, f_2)|^2}{\sum_\Omega |B(f_1, f_2)|^2} \quad (8)$$

On-line DWT Processor:

Discrete Wavelet Transform (DWT) is a transform that captures both the time and frequency information of the signal. DWT analyzes the atherosclerotic wall longitudinal ultrasound image (or Atherosclerotic Wall region image of MR, CT, 3D Carotid Ultrasound or 3D IVUS) by decomposing it into coarse approximation via low-pass filtering and into detail information via high-pass filtering. Such decomposition is done recursively on the low-pass approximation coefficients obtained at each level, until the necessary iterations are reached.

Let each atherosclerotic wall region longitudinal image (or Atherosclerotic Wall region image of MR, CT, 3D Carotid Ultrasound or 3D IVUS) be represented as a p×q grayscale matrix I[i,j], where each element of the matrix represents the grayscale intensity of one pixel of the image. Each non-border pixel has eight adjacent neighboring pixel intensities. These eight neighbors can be used to traverse through the matrix. The resultant 2D-DWT coefficients will be the same irrespective of whether the matrix is traversed right to left or left to right. Hence, it is sufficient that we consider four decomposition directions corresponding to 0° (horizontal, Dh), 90° (vertical, Dv) and 45° or 135° (diagonal, Dd) orientation. The decomposition structure for one level is illustrated in the diagram below. I is the image, g[n] and h[n] are the low-pass and high-pass filters, respectively and A is the approximation coefficients. In this work, the results from level I were found to yield significant features. FIG. 39 shows the 2D DWT decomposition. 2ds1 indicates that rows are down sampled by 2 and columns by 1. 1ds2 indicates that rows are down sampled by 1 and columns by 2. '×' operator indicates convolution operation.

As is evident from the diagram above, the first level of decomposition results in four coefficient matrices, namely, A1, Dh1, Dv1, and Dd1. Since the number of elements in these matrices is high, and since we only need a single number as a representative feature, we employed averaging methods to determine such single-valued features. The following are the definitions of the three features that were determined using the DWT coefficients.

$$\text{Average } Dh1 = \frac{1}{p \times q} \sum_{x=<p>} \sum_{y=<q>} |Dh1(x, y)| \quad (9)$$

$$\text{Average } Dv1 = \frac{1}{p \times q} \sum_{x=<p>} \sum_{y=<q>} |Dv1(x, y)| \quad (10)$$

$$\text{Energy} = \frac{1}{p^2 \times q^2} \sum_{x=<p>} \sum_{y=<q>} (Dv1(x, y))^2 \quad (11)$$

Equations (9) and (10) calculate averages of the corresponding intensity values, whereas equation (11) is an averaging of the energy of the intensity values. For the Atherosclerotic Wall region image of MR, CT, 3D Carotid Ultrasound or 3D IVUS, same features, Average Dh1, Average v1 and Energy are computed which are then used for classification and risk score estimation.

On-line Texture Processor:

The texture of an image is characterized by the regular repletion of patterns in the image. There are several approaches to analyzing the textural properties, and in this work, we studied the statistical textural features that are based on the relationship and distribution of pixel intensities. Consider $\phi(i)$ as the number of pixels with intensity value i, ranging from 1 to n. Let A be the area of the image. The probability of intensity i in the image is given by:

$$h(i) = \frac{\varphi(i)}{A} \quad (12)$$

The standard deviation is then defined as $$\text{Deviation} = \sum_{i=1}^{n} (i - \mu)^2 h(i) \quad (13)$$

where $\mu$ is the mean of the pixel intensities.

Next, two matrices, namely, the Gray Level Co-occurrence Matrix (GLCM) and the Run Length Matrix were determined based on the pixel intensities, and features were extracted from these matrices. They are defined as follows.

Gray Level Co-occurrence Matrix
The GLCM of an image I of size m×n is given by $$C_d = \left| \left\{ \begin{array}{c} (p,q), (p+\Delta x, q+\Delta y): I(p,q) = i, \\ I(p+\Delta x, q+\Delta y) = j \end{array} \right\} \right| \quad (14)$$

where (p,q), (p+Δx, q+y) belongs to m×n, d=(Δx,Δy), and |...| denotes the set cardinality. The probability of a pixel with intensity i having a pixel with an intensity j at a distance (Δx, Δy) away is given by:

$$P_d(i,j) = \frac{C_d(i,j)}{\sum_{(i)}\sum_{(j)} C_d(i,j)} \quad (15)$$

where the summation is over all possible i and j. From equations (14) and (15), the following two features can be calculated.

$$\text{Symmetry} = 1 - \sum_i \sum_j |_c C_d(i,j) -_c C_d(j,i)| \quad (16)$$

$$\text{Entropy} = -\sum_i \sum_j P_d(i,j) \times \ln[P_d(i,j)] \quad (17)$$

Entropy, which denotes the degree of disorder in an image, will have high value if the elements in the GLCM are the same.

Run Length Matrix:

The run length matrix $P_\theta$ consists of all the elements where the intensity value i has the run length j continuous in direction θ. Typically values of θ are 0°, 45°, 90°, or 135°. The feature called Run Length Non-uniformity (RLnU) is then determined as follows.

$$RLnU = \sum_{(j)} \left( \sum_{(i)} P_\theta(i,j) \right)^2 \quad (18)$$

Since RLnU measures the similarity of the run lengths, its value will be less if the run lengths are uniform throughout the image. For the Atherosclerotic Wall region image of MR, CT, 3D Carotid Ultrasound or 3D IVUS, same features, Symmetry, Entropy, RLnU are estimated from Gray Level Co-occurrence Matrix (GLCM) and the Run Length Matrix. They are based on the pixel intensities computed in the wall region between the lumen border and outer wall border. These texture features are then used for classification and risk score estimation.

LBP Feature

Local Binary Pattern (LBP): Local Binary Pattern (LBP) has been established as a robust and efficient texture descriptor and was first presented by Ojala et al. (1996, 2002). LBP has been successfully applied to a wide range of different applications from texture segmentation (Liao et al. 2009) to face recognition (Zhang et al. 2010). The LBP feature vector, in its simplest form, is determined using the following method.

A circular neighborhood is considered around a pixel. P points are chosen on the circumference of the circle with radius R such that they are all equidistant from the center pixel. The gray values at points on the circular neighborhood that do not coincide exactly with pixel locations are estimated by interpolation. Let $g_c$ be the gray value of the centre pixel and $g_p$, p=0, ..., P−1, corresponds to the gray values of the P points. These P points are converted into a circular bit-stream of 0s and 1s according to whether the gray value of the pixel is less than or greater than the gray value of the center pixel. FIG. 5.*depicts* circularly symmetric neighbor sets for different values of P and R.

Ojala et al. (2002) introduced the concept of uniformity in texture analysis. They did so by classifying each pixel as uniform or non-uniform and used the uniform pixels for further computation of texture descriptor. These "uniform" fundamental patterns have a uniform circular structure that contains very few spatial transitions U (number of spatial bitwise 0/1 transitions), and thus, function as templates for microstructures such as bright spot (U=0), flat area or dark spot (U=8), and edges of varying positive and negative curvature (U=1–7). Therefore, a rotation invariant measure called $LBP_{P,R}$ using uniformity measure U is calculated based on the number of transitions in the neighborhood pattern. Only patterns with U<2 are assigned the LBP code as depicted in equation (3) i.e. if the number of bit-transitions in the circular bit-stream is less than or equal to 2, the centre pixel is labelled as uniform. A look up table is generally used to compute the bit-transitions to reduce computational complexity.

$$LBP_{P,R}(x) = \begin{cases} \sum_{p=0}^{P-1} s(g_p - g_c) & \text{if } U(x) \leq 2 \\ P+1 & \text{otherwise} \end{cases} \quad (1)$$

$$\text{where } s(x) = \begin{cases} 1, & x \geq 0 \\ 0, & x < 0 \end{cases}$$

Multi-scale analysis of the image using LBP is done by choosing circles with various radii around the centre pixels and thus constructing separate LBP image for each scale. In our work, energy and entropy of the LBP image, constructed over different scales (R=1, 2, and 3 with the corresponding pixel count P being 8, 16, and 24, respectively) were used as feature descriptors.

Law's Musk Energy (LME) Feature

Laws mask has evolved with the idea of representing image features without referring to the frequency domain (Gupta and Undrill 1995). The idea of inferring as what looks like where, instead of the conventional what happens where, is the essence of using this approach as a conjunction to the human visual perception (Petrou and Sevilla 1980). Laws empirically determined that several masks of appropriate sizes were very informative for discriminating between different kinds of texture (Laws 1980). Originally, he classified samples based on expected values of variance-like square measures of these convolutions, called texture energy measures (Laws 1980). The texture energy measure is quantified using the three masks L3=[1, 2, 1], E3=[−1, 0, 1], and S3=[−1, 2, −1], for level, edge, and spot detection, respectively. The appropriate convolution of these masks yield nine different combination of 3×3 masks, of which we use the eight zero-sum masks numbered 1 to 8. The image under inspection is filtered using these eight masks, and their energies are computed and used as the feature descriptor (Petrou and Sevilla 1980). A more detailed analysis of applications of Law's texture can be seen in the recent book by Mermehdi et al. (2008).

On Line Trace Transform Processor

Trace transform is a generalized approach to the Radon transform, and consists of tracing an image with straight lines along which certain functional of the image function. The purpose of a functional is to characterize a function by a number. Different functionals are used for representation of rotation, translation and scaling invariant features of an image, construction of features that may correlate well with the visual texture (A. Kadyrov, and M. Petrou, "The trace transform and its applications," *IEEE Trans. Pattern Anal., Machine Intel.*, vol. 23, no. 8, pp. 811-828, August 2001). Let the studied image be scanned with lines in all directions. Let A be the set of all these lines. The Trace transform can then be defined as a function g defined on A with the help of T which is some functional of the image function of variable t. T is called the trace functional. In order to define a triple feature, two more functionals designated by letters P and $\Phi$ are defined. P, called the diametrical functional, is a functional of the Trace transform function when it is considered as a function of the length of the normal to the line only. $\Phi$, called the circus functional, is a functional operating on the orientation variable, after the previous two operations (use of T and P) have been performed. Thus, the triple feature can be defined as $$\Pi(F,C_1) = \Phi(P(T(F(C_1;\phi;p;t)))) \quad \text{(TT-1)}$$

where $F(C_1;\phi;p;t)$ indicates the values of the image function along the chosen line. $C_1$ is the co-ordinate system parameterized by $(\phi; p;t)$. We calculate two triple features using the invariant functionals defined as follows:

$$\Pi_1 = (T \rightarrow IF, P \rightarrow IF_2, \Phi \rightarrow IF_3) \quad \text{(TT-2)}$$

$$\Pi_2 = (T \rightarrow IF_3, P \rightarrow IP_2, \Phi \rightarrow IF_1) \quad \text{(TT-3)}$$

where $\Pi_1$ is the normalized version of the triple feature formed by using $IF_1$, $IF_2$, and $IF_3$ for functionals T, P, and $\phi$ respectively in Eq. (1). $\Pi_3$ is the normalized version of the triple feature formed by using $IF_3$, $IF_2$, and $IF_1$ for functionals T, P, and $\phi$ respectively in Eq. (1). $\Pi_1$ and $\Pi_2$ are the rotation, scale and translation invariant texture features that were used to quantify visual texture measure in our application.

Fuzzy Grayscale Level Co-occurrence Matrix (FGLCM) Feature

Gray Level Co-occurrence Matrix (GLCM) represents second-order texture moments, and it is made up of the frequency of appearance of a gray level in a specified linear relationship with another gray level within the neighborhood of interest. The Fuzzy GLCM (FGLCM) [24] of an image I of size L×L is given by:

$$F_d(m,n) = [f_{mn}]_{L \times L} \quad \text{(F-4)}$$

where $f_{mn}$ corresponds to the frequency of occurrence of a gray-value 'around m' separated from another pixel, with gray-value 'around n', by a distance d in a specific direction $\theta$. It is represented as $F = f(I,d,\theta)$.

In this study, we used rotational invariant co-occurrence matrix F', obtained by averaging the four symmetrical fuzzy co-occurrence matrices computed with $\theta = 0°, 45°, 90°, 135°$ and d=20, to find the texture feature value. The pyramidal membership function $\mu_{\tilde{m}I(x,y),\tilde{n}I(x,y\pm d)}$ used to build these matrices has a support of 11×11 pixels. Here, $\mu$ represents fuzzy membership distribution of gray values around 'm' and 'n'. Given F', it is normalized to obtain $F'_{norm}$ which gives the joint probability of occurrence of one pixel having gray-value 'around in' with another pixel separated by a defined spatial relationship and having gray-value 'around n'. Based on the above-mentioned, we obtain the following FGLCM based features:

$$\text{Energy: } E_{fuzzy} = \sum_m \sum_n [F_d(m,n)]^2 \quad \text{(F-5)}$$

$$\text{Contrast: } C_{fuzzy} = \sum_m \sum_n (m-n)^2 F_d(m,n) \quad \text{(F-6)}$$

$$\text{Homogeneity: } G_{fuzzy} = \sum_m \sum_n \frac{F_d(m,n)}{1+(m-n)^2} \quad \text{(F-7)}$$

$$\text{Entropy: } H_{fuzzy} = -\sum_m \sum_n F_d(m,n) \cdot \ln F_d(m,n) \quad \text{(F-8)}$$

$$\text{Correlation: } Corr_{fuzzy} = \frac{\sum_m \sum_n [mn F_d(m,n)] - \mu_m \mu_n}{\sigma_m \sigma_n} \quad \text{(F-9)}$$

where $$\mu_m = \sum m F_d(m,n), \; \sigma_m^2 = \sum m^2 F_d(m,n) - \mu_m^2 \quad \text{(F-10)}$$

$$\mu_n = \sum n F_d(m,n), \; \sigma_n^2 = \sum n^2 F_d(m,n) - \mu_n^2 \quad \text{(F-11)}$$

Moments $M_1, M_2, M_3$, and $M_4$:

$$M^g_{fuzzy} = \sum_m \sum_n (m-n)^g F_d(m,n) \quad \text{(F-12)}$$

The similarity between two pixels that are $(\Delta m, \Delta n)$ apart is measured by the homogeneity feature. On the contrary, the local variation between those two pixels is captured by the contrast feature. The denseness and the degree of disorder in an image are measured by energy and entropy features. The entropy feature will have a maximum value when all elements of the co-occurrence matrix are the same. Difference statistics is defined as "the distribution of the probability that the gray-level difference is k between the points separated by $\delta$ in an image" (F. Tomita and S. Tsuji, *Computer analysis of visual textures*. Kluwer Academic Publishers, Boston, 1990). The difference statistics vector being a subset of the fuzzy co-occurrence matrix can be obtained from FGLCM as:

$$F_\delta(k) = \sum_{\substack{m \\ |m-n|=k}} \sum_n F_d(m,n) \quad \text{(F-13)}$$

where k=0, 1, ... c−1, c is the number of gray scale levels [26], and $\delta$ is d=$(\Delta m, \Delta n)$. Based on the acquired vector, we obtain the following difference statistics based features (IS. Weszka and A. Rosenfield, "An application of texture analysis to material inspection." *Pattern Recogn.*, vol. 8. no. 4. pp. 195-200. 1976):

$$\text{Angular Second Moment: } ASM_{diff} = \sum_{k=0}^{c-1} F_\delta(k)^2 \quad \text{(F-14)}$$

When the $F_{67}$ (k) values are very similar or close, ASM is small. ASM is large when certain values are high and others are low.

$$\text{Mean: } \mu_{diff} = \sum_{k=0}^{c-1} k F_\delta(k) \quad \text{(F-15)}$$

When $F_\delta(k)$ values are concentrated near the origin, mean is small and mean is large when they are far from the origin.

$$\text{Contrast: } C_{diff} = \sum_{k=0}^{c-1} k^2 F_\delta(k) \quad \text{(F-16)}$$

Contrast is also known as the second moment of $F_\delta$ (its moment of inertia about the origin).

$$\text{Entropy: } H_{diff} = -\sum_{k=0}^{c-1} F_\delta(k) \log F_\delta(k) \quad \text{(F-17)}$$

Entropy is smallest when $F_\delta(k)$ values are unequal, and largest when $F_\delta(k)$ values are equal. Entropy is directly proportional to unpredictability.

The above mentioned features were calculated for $\delta=(0, 1)$, $(1, 1)$, and $(1, 0)$, and the total mean values for the four features were taken.

The FGLCM contains information about the positions of pixels having similar gray level values, and hence, the features in Eqns. (F-5 to F-12) quantify this information. However, the difference statistics based features (Eqns. F-13 to Eqns. F-17)) are derived from the vector based on absolute differences between pairs of gray levels. Even though the definitions of features like contrast (Eq. (F-6) and Eq. (F-16)) and entropy (Eq. (F-8) and Eq. (F-17)) are similar, they are calculated on different matrices/vectors that quantify the texture of the image in different ways.

Fuzzy Run Length matrix (FRLM)

The run length matrix, $F_\theta(m,n)$ consists of the number of elements where gray level value i has the run length j continuous in direction $\theta$. Often the direction $\theta$ is set as 0°, 45°, 90°, and 135° (M. M. Galloway, "*Texture analysis using gray level run lengths,*" *Comput. Graphics Image Process.*, vol. 4, no. 2, pp. 172-179, 1975 and K. V. Ramana and B. Ramamoorthy, "Statistical methods to compare the texture features of machined surfaces," *Pattern Recogn.*, vol. 29, pp. 1447-1459, 1996). The features listed below were calculated for analysis and classification:

Fuzzy Short Run Emphasis:

$$SRE_{fuzzy} = \sum_m \sum_n \frac{F_\theta(m, n)}{n^2} \Big/ \sum_m \sum_n F_\theta(m, n) \quad \text{(F-18)}$$

Fuzzy Long Run Emphasis:

$$LRE_{fuzzy} = \sum_m \sum_n n^2 F_\theta(m, n) \Big/ \sum_m \sum_n F_\theta(m, n) \quad \text{(F-19)}$$

Fuzzy Gray Level Non-Uniformity:

$$GLNU_{fuzzy} = \sum_m \left\{ \sum_n F_\theta(m, n) \right\}^2 \Big/ \sum_m \sum_n F_\theta(m, n) \quad \text{(F-20)}$$

Fuzzy Run Length Non-Uniformity:

$$RLNU_{fuzzy} = \sum_n \left\{ \sum_m F_\theta(m, n) \right\}^2 \Big/ \sum_m \sum_n F_\theta(m, n) \quad \text{(F-21)}$$

Fuzzy Run Percentage:

$$RP_{fuzzy} = \sum_m \sum_n F_\theta(m, n) / A \quad \text{(F-22)}$$

where A is the area of the image of interest.

On-line Wall Variability Processor:

This is computed by measuring the standard deviation of the IMT. As mentioned in the previous sections, AtheroEdge™ algorithm was employed to determine the LI and MA borders. We will discuss the AtheroEdge™ system for non-shadow ultrasound scans and with shadow ultrasound scans. In order to calculate the distance between LI and MA borders (IMT), the Polyline Distance Measure (PDM) was used. PDM is based on vector calculus, and in this method, we measure the distance of each vertex of one boundary to the segments of the second boundary.

Consider two boundaries $B_1$ and $B_2$. The distance $d(v,s)$ between a vertex $v=(x_0,y_0)$ on the $B_1$ and a segment s formed by the endpoints $v_1=(x_1,y_1)$ and $v_2=(x_2,y_2)$ on $B_2$ can be defined as:

$$d(v, s) = \begin{cases} d_\perp & 0 \leq \lambda \leq 1 \\ \min\{d_1, d_2\} & \lambda < 0, \lambda > 1 \end{cases} \quad (19)$$

where $d_1$ and $d_2$ are the Euclidean distances between the vertex v and the endpoints of segment s; $\lambda$ is the distance along the vector of the segment s; $d_\perp$ is the perpendicular distance between v and the segment s.

The polyline distance from vertex v to the boundary $B_2$ can be defined as $$d(v, B_2) = \min_{x \in B_2} \{d(v, s)\}.$$

The instance between the vertexes of $B_1$ to the segments of $B_2$ is defined as the sum of the distances from the vertexes of $B_1$ to the closest segment of $B_2$:

$$d(B_1, B_2) = \sum_{v \in B_1} d(v, B_2) \qquad (20)$$

Similarly, $d(B_2, B_1)$, which is the distance between the vertices of $B_2$ to the closest segment of $B_1$, can be calculated by simply swapping the boundaries. The polyline distance between boundaries is the defined as:

$$D(B_1, B_2) = \frac{d(B_1, B_2) + d(B_2, B_1)}{(\# \text{ of vertices of } B_1 + \# \text{ of vertices of } B_2)} \qquad (21)$$

When $B_1$ is taken to be the LI boundary, and $B_2$ the MA boundary, the resultant $D(B_1, B_2)$ is called the IMT measure. The variability in the distance measurements can be computed as:

$$\sigma^2(B_1, B_2) = \sum_{v \in B_1} (d(v, B_2) - d(B_1, B_2))^2 \qquad (22)$$

$$\sigma^2(B_2, B_1) = \sum_{v \in B_2} (d(v, B_1) - d(B_2, B_1))^2 \qquad 1.1 \ (23)$$

and the $WV_{poly}$ (or IMTVpoly) can be determined using the following equation.

$$IMTV_{poly} = \sqrt{\frac{\sigma^2(B_1, B_2) + \sigma^2(B_2, B_1)}{\# \text{ vertices of } B_1 + \# \text{ vertices of } B_2}} \qquad (24)$$

Figure 40:
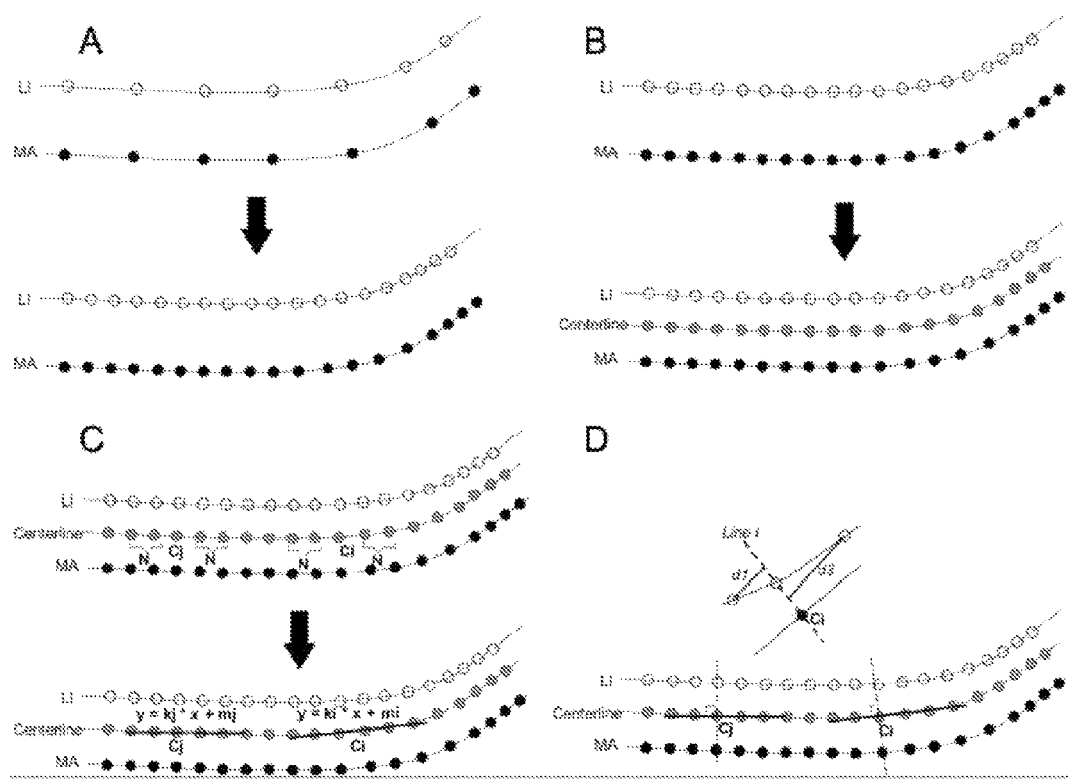
FIG. 40 shows the concept of centerline method.

Those skilled in the art, can also use Centerline method. The algorithm consists of the following stages: (a) interpolating the LI and MA borders to say a fixed number of points (say 100); (b) finding the centreline points between the LI and MA borders along the longitudinal carotid artery; (c) finding the chords and their lengths which are perpendicular to the LI and MA segments passing through the centreline points; (d) estimating the mean and standard deviations of the chord lengths corresponding to each centreline points along the carotid artery and (e) IMTV is defined as the standard deviation of the far carotid LI and MA walls. The Figure (A, B, C and D) summarizes the computation steps. Examples showing the chords along the carotid artery as shown in FIG. 40.

The key advantage of using PDM over other IMT and variability measurement techniques is that the measured distance is robust because it is independent of the number of points on each boundary.

Feature Selection Process:

Student's t-test is used to assess whether the means of a feature from two classes are significantly different. In order to determine this, initially, the null hypothesis is assumed that the means of the features from the two classes are equal. Then, the t-statistic, which is the ratio of difference between the means of two classes to the standard error between class means, and the corresponding p-value are calculated. The p-value is the probability of rejecting the null hypothesis given that the null hypothesis is true. A low p-value (less than 0.01 or 0.05) indicates rejection of null hypothesis, and therefore, the fact that means are significantly different for the two classes. FIG. 29 (table) presents the significant features obtained for longitudinal carotid artery scan.

In the case of HOS based features, two significant phase entropy based features were obtained for Radon transform angles $\theta=106°$ and $\theta=107°$. These features are denoted in FIG. 29 (table) as ePRes(106°) and ePRes (107°). Two other features were the normalized bispectral entropies obtained at $\theta=38°$ and $\theta=39°$ denoted by e1Res(38°) and e1Res(39°). Another HOS feature is the normalized bispectral squared entropy obtained at $\theta=39°$ denoted by e2Res(39°) in FIG. 29 (Table). The Wall Variability feature was also found to be highly significant.

In the case of DWT features, we calculated the three features (Average Dh1, average Dv1, and energy) for 54 different wavelet functions based on the following mother wavelet families: reverse biorthogonal wavelet family (rbio), Daubechies wavelet (db), Biorthogonal 3.1 wavelet (bior), Coiflets, Symlets, Discrete Meyer (FIR approximation) (dmey) and Haar family. HOS features were most significant feature, however other combinations of these feature can be adapted. In the case of texture features, the four features (deviation, symmetry, entropy, and RLnU) were also not found to be as significant as the HOS and wall variability features. These features were very affective for 3D application such as CT, MR, 3D carotid Ultrasound and 3D IVUS.

Figure 7:
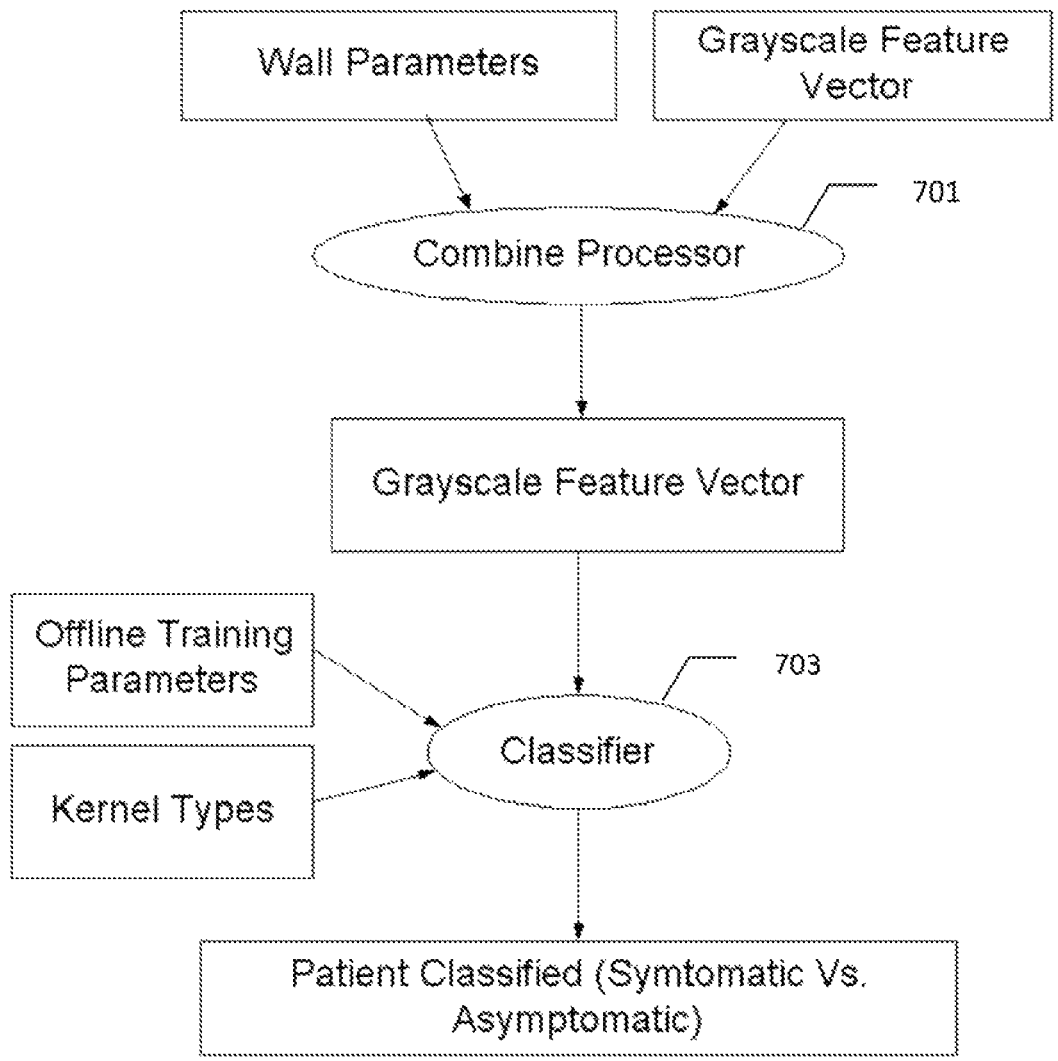
FIG. 7 shows the on-line symptomatic vs. asymptomatic classification system.

FIG. 7 shows the on-line symptomatic vs. asymptomatic classification system. The classifier system accepts the feature vector (combined from the combined processor). This feature vector is the combination of the grayscale features and the wall variability features. The on-line classification system accepts the input from the off-line training parameters which are then applied to the classification system to check if the patient is symptomatic or asymptomatic. This classification can be any classification such as Support Vector Machine (SVM), Adaboot Classifier, Fuzzy Classifier, etc. Same online system is applicable for CT, MR, 3D carotid Ultrasound and 3D IVUS classification system.

Figure 8:
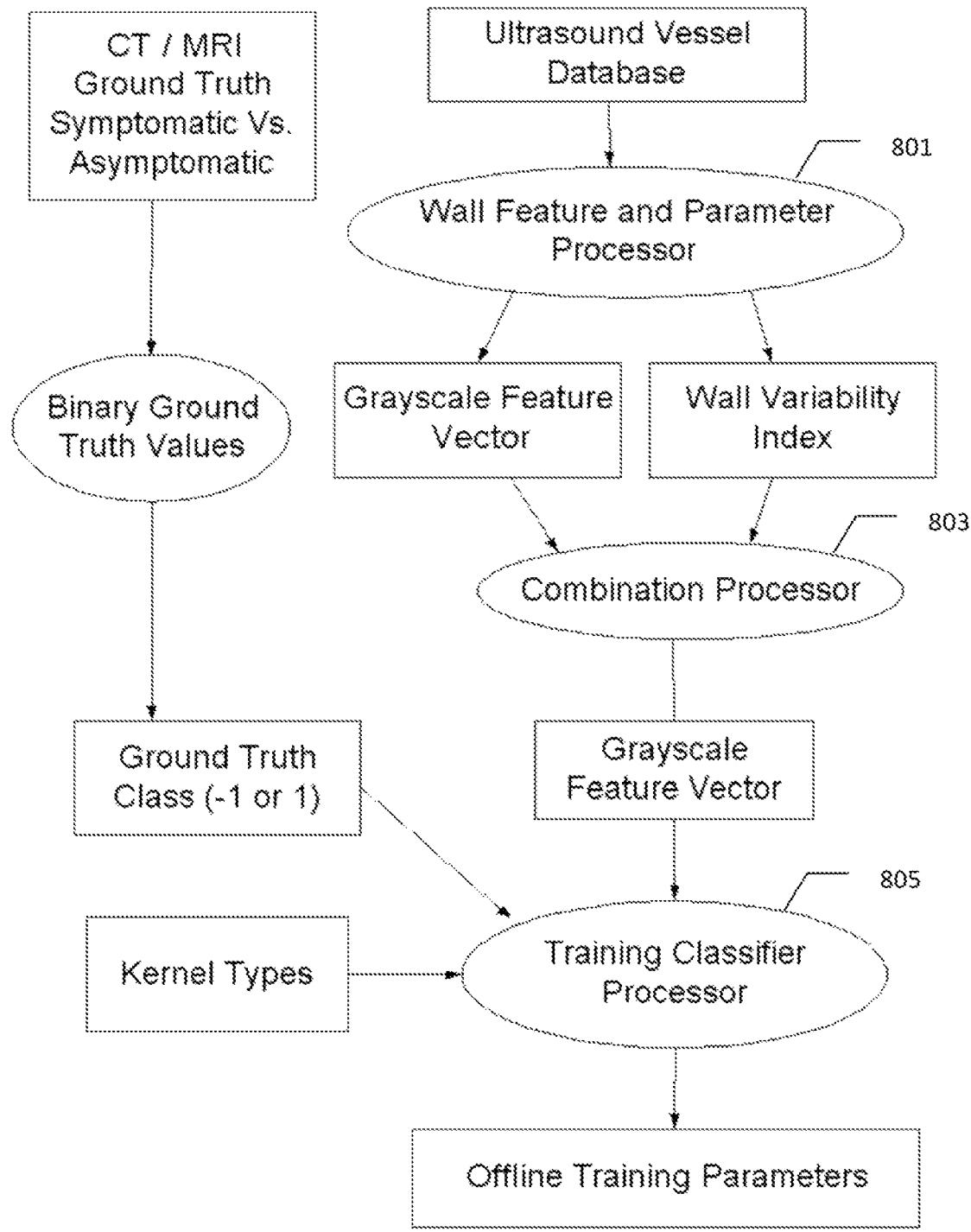
FIG. 8 shows the off-line system for generating the training parameters. It uses the binary ground truth processor which uses off-line CT/MR system to collect the ground truth symptomatic/asymptomatic which is used for training system.
Figure 33:
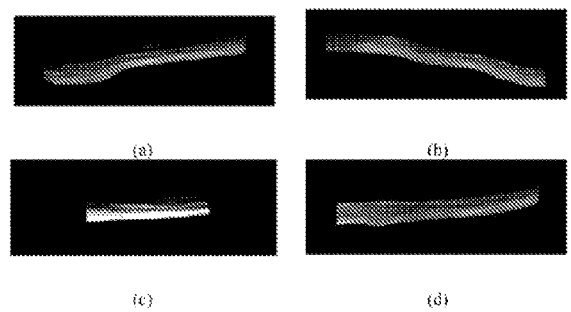
FIG. 33 showing the Atherosclerotic Wall Region used for grayscale feature extraction (HOS feature, DWT feature and Texture Feature). Figure (a) and (b) for the symptomatic wall region and (c) and (d) for Asymptomatic wall region.
Figure 34:
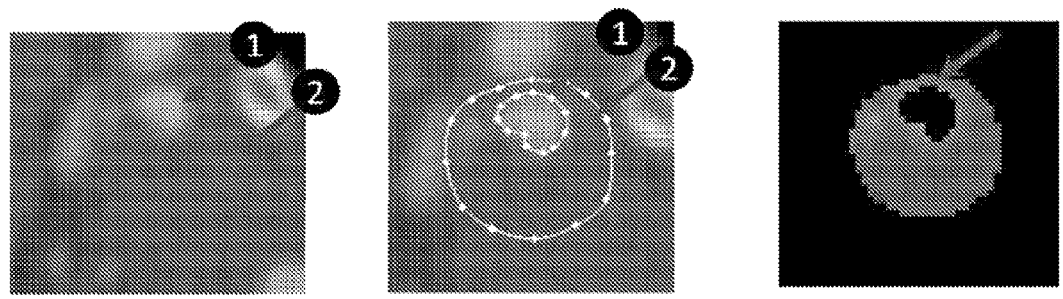
FIGS. 34, 35, 36, 37 are the symptomatic and asymptomatic cases using CT.
Figure 35:
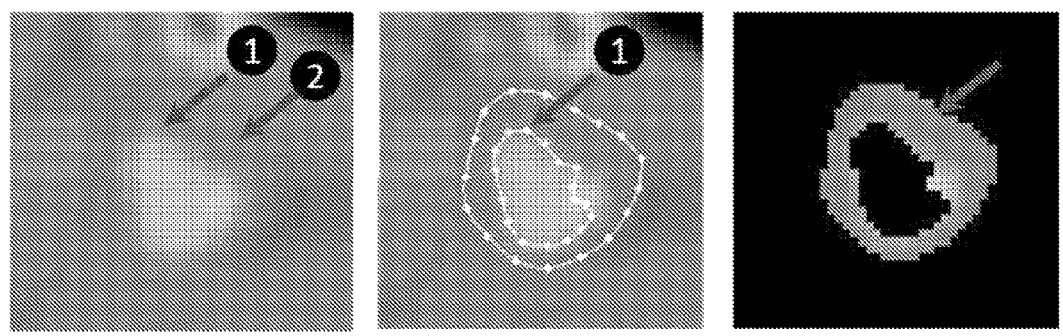
Figure 36:
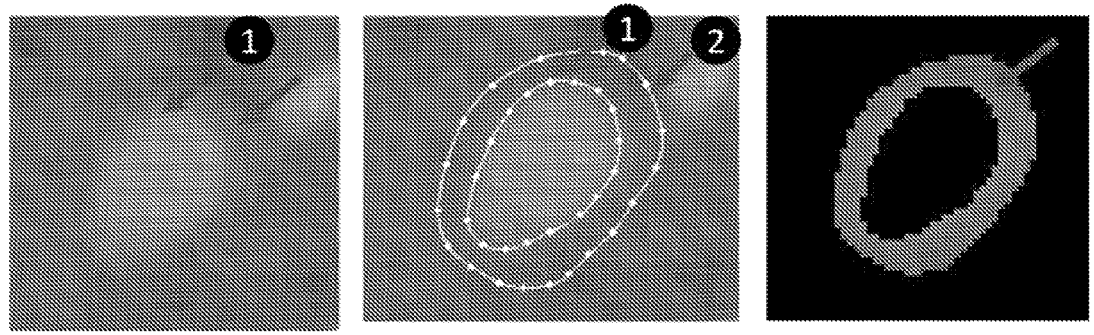
Figure 37:
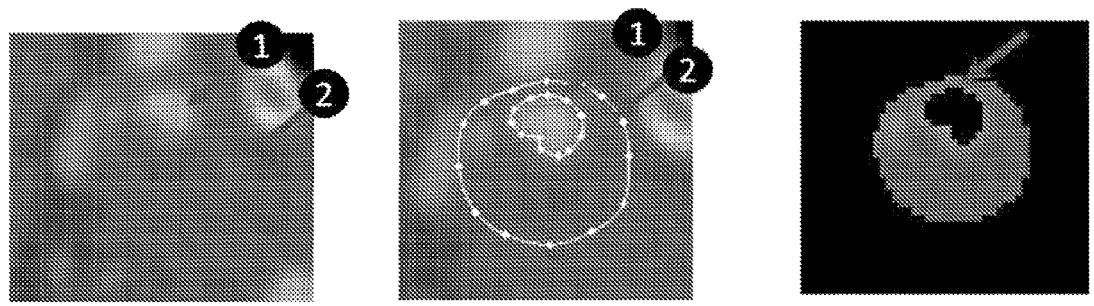

FIG. 8 shows the off-line system for generating the training coefficients. There are four processors in the training-based system: (a) Wall Feature and Wall Parameter Processor; (h) Combination Processor; (c) Off-line Ground Truth Processor; (d) Training Processor. Wall Feature and Wall Parameter Processor consists of Wall LIMA processor just like we had during the on-line process (as shown in FIG. 3). The only difference is that, the Wall Feature Processor is applied to the training images off-line. The off-line Wall Feature Processor consists of: (a) LIMA processor; (b) Wall Variability Processor and (c) Grayscale Feature Processor. The LIMA processor finds the Lumen-Intima (LI) border and Media-Adventitia (MA) borders on the training longitudinal CCA ultrasound image database. The process takes an input training ultrasound image and finds the LIMA border and corresponding grayscale region inside the LIMA border. An example of the grayscale region is shown in FIG. 33. The grayscale region is subjected to Grayscale Feature extraction using Grayscale Feature Processor and the LIMA borders are subjected to Wall Variability using Wall Variability Processor, off-line. The wall variability is a significance indicator about the extensiveness of the variability of the changes in the media layer where the plaque deposition starts early in the walls. This variability figure can be computed using several methods such as centerline method, polyline distance methods, distance transform methods, variation method or manual methods. The grayscale feature Processor computes grayscale features based on: (a) Higher Order Spectra; (b) Discrete Wavelet Transform (DWT); and (c) Texture. In another methodology used here is to compute the grayscale features in the Atherosclerotic Wall Region such as: Local Binary Pattern (LBP) and Laws Mask Energy (LME) and Wall Variability. Those skilled in the art can also use Fuzzy methods for feature extraction during the training process. The LIMA borders are computed using the LIMA process off-line. This is similar to the FIG. 4 what consists of two processors: (a) Artery recognition processor (ARP) and (b) LIMA border processor. Artery recognition processor is used for recognition of the far wall of the artery in the training image frame. Since the training image frame has Jugular vein and CCA artery, the ARP automatically identifies the far wall of the CCA in the training image. The same method is applicable to training Brachial, Femoral or Aortic Arteries. The output of the ARP is the ADF (far adventitia) border. The LIMA border processor inputs the grayscale image and the ADF border and then computes the LIMA borders. The LIMA border consists of LI and MA borders. This the list of coordinates (x,y) for the LI and list of coordinates (x,y) for the MA border (off-line). The off-line wall variability is computed the same way as it is computed for the on-line wall variability. This can be seen in the FIG. 5. It consists of off-line (a) Middle line Processor, (b) off-line Chord Processor and (c) off-line Wall Variability Processor. This off-line processor gets its inputs from the off-line LIMA processor, which consists of (x,y) list of coordinates. The off-line processor can compute the middle line of the LIMA borders, the middle line chords of the vessel wall borders and it off-line variability index. The off-line middle line borders are the set of list of (x,y) coordinates which are exactly half way between the LI and MA borders. Off-line chord processor helps in computing the perpendicular lines along the arterial vessel wall between the off-line LI and MA borders. This variability indicator is critical in computing the feature vector for the off-line training image. Feature vector is computed as a combination of grayscale features and the wall variability. This includes computation of off-line features using: (a) Higher Order Spectra; (b) Discrete Wavelet Transform (DWT); and (c) Texture and (d) wall variability. In another methodology used here is to compute the grayscale features in the Atherosclerotic Wall Region such as: Local Binary Pattern (LBP) and Laws Mask Energy (LME) and Wall Variability. Grayscale off-line Features are computed in the same way as shown in FIG. 6A, FIG. 6B, and FIG. 6C. The Grayscale off-line Feature Processor consists of off-line: (a) Texture Processor; (b) DWT Processor and (c) Radon Processor and (d) Combine Processor. In another methodology used here is to compute the grayscale features in the Atherosclerotic Wall Region such as: Local Binary Pattern (LBP), Laws Mask Energy (LME) and Wall Variability. Once the off-line Guidance zone is computed using the off-line LIMA borders (output of the off-line LIMA processor), the off-line system runs the feature extraction process there by computing the grayscale features. These off-line features are then combined to get an output using the off-line Combined Processor. Off-line texture Processor computes the off-line texture features, off-line DWT Processor computes the discrete wavelet transform features and off-line radon processor computes the off-line order spectra features for the walls. Off-line combine processor combines all these grayscale features along with the wall variability features yielding the combined features. These combined features (shown in FIG. 8) are used with the ground truth information to generate the training parameters. The off-line Ground Truth information consists of symptomatic vs. asymptomatic information about the training database images. This Ground Truth information is a binary list of 0's and 1's representing as asymptomatic and symptomatic class in the Atherosclerotic plaque region. An example of the GT information is shown in the table below where row #1 represent the patient ultrasound training scan image while the row #2 shows the binary information in the form of 1's or 0's representing the symptomatic and asymptomatic nature of the plaque in the carotid arterial wall.

| | Trg. Pat# | | | | | | | |
|---|---|---|---|---|---|---|---|---|
| | 1003 | 1004 | 1005 | 1006 | 1007 | 1008 | 1009 | 1010 |
| GT info | 1 | 1 | 0 | 0 | 0 | 0 | 1 | 1 |

Note that the FIG. 8 is an off-line representative system when applied to the carotid artery. The same system is applicable to brachial, femoral and aortic walls. Also note that the system is applicable to the cross-modality training. This means that the off-line system can be used for Magnetic Resonance arteries or Computer Tomography or 3D carotid Ultrasound or 3D IVUS arteries. The only flexibility this system has that during the training process, the ground truth information can be taken from cross-modalities such as MR, CT or Ultrasound or IVSU images.

Classification Strategy:

Generally, 70% of the available images are used for training and the remaining 30% are used for testing. Those skilled in the art can use lot of different kind of training protocols such as equal partition, different permutation and combination methods and/or jack knifing, etc. The performance measures are reported based on the results obtained using the test set. These measures, reported using the hold-out technique, are highly dependent on the samples chosen for the training and test sets. In order to obtain more generalized measures, especially for small sample size datasets such as the one in this application, the preferred data re-sampling technique is the k-fold cross validation technique. In this work, we employed three-fold cross validation wherein the dataset is split into three folds. In the first run, two folds are used for training and the remaining one fold is used for testing and for obtaining the performance measures. This procedure is repeated two more times by using a different fold for testing every time. The overall performance measures are the averages of the performance measures obtained in each run. This procedure was stratified, in the sense that, we ensured that the ratio of the samples belonging to the two classes (class distribution) remained the same in every run.

Figure 9:
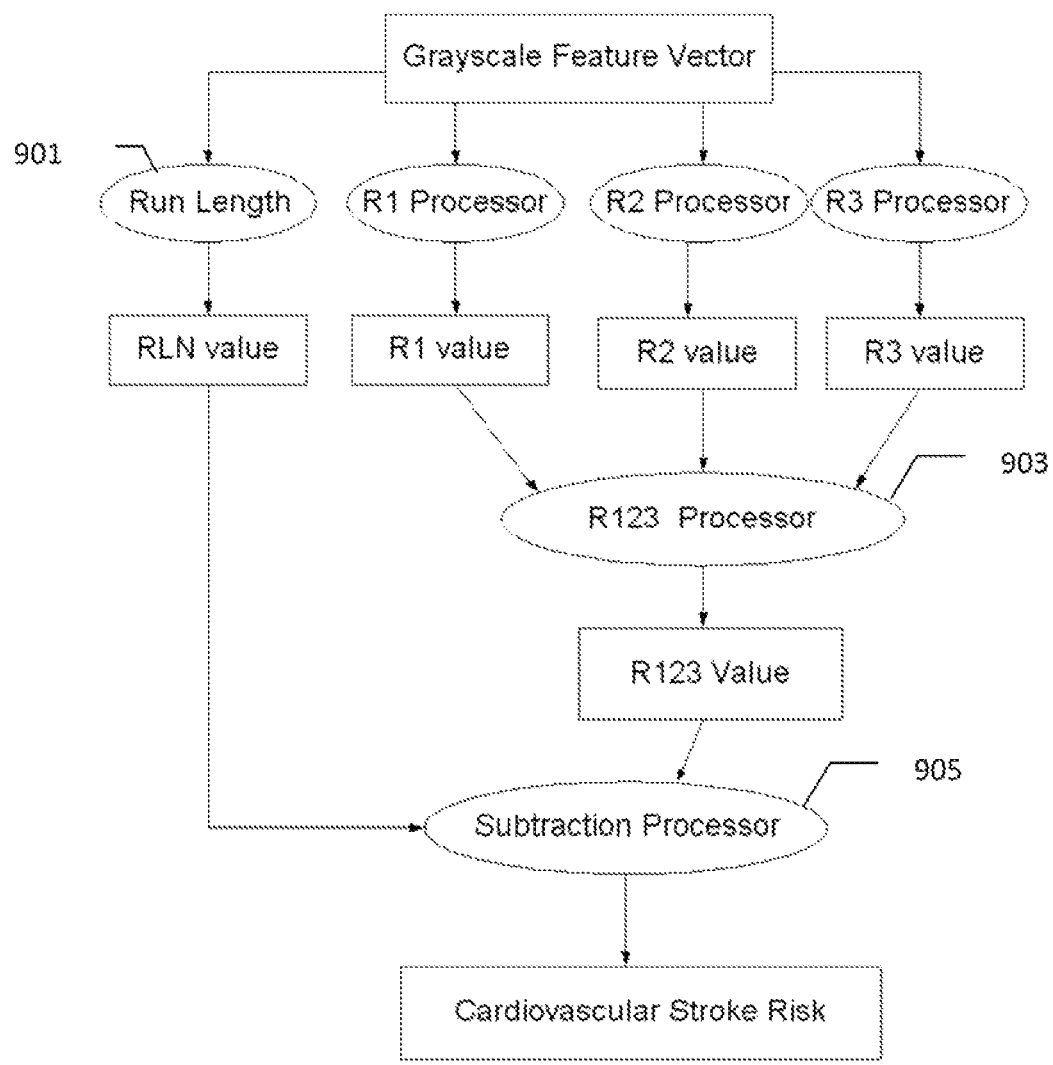
FIG. 9 shows the Cardiovascular Risk Score (CVRS) system.

FIG. 9 shows the Cardiovascular Risk Score (CVRS) system. This consists of four processors: (a) Run Length Processor; (b) R1 processor; (c) R2 processor; and (d) R3 processor. The output of the R1, R2 and R3 processors give three outputs: R1, R2 and R3. Processor R123 combines the three values R1, R2 and R3, which yields the combined clinical feature called R123. The final cardiovascular risk score is estimated by using a subtraction processor which inputs the R123 and RunLength values. Risk Score (without Wall Variability): e1Res38+e1Res39+e2Res39−ePRes106+ePRes107, where e1Res=−$\Sigma_i p_i \log p_i$ is the Normalized Bi-spectral Entropy and e2Res=−$\Sigma_n p_n \log p_n$ is the Normalized Bi-spectral Entropy. An representative example of the features used in designing the cardiovascular risk score is shown in the table below:

| Feature | Asymptomatic | Symptomatic | P value |
|---|---|---|---|
| e1Res (38 degree) | 0.477 ± 6.196E-02 | 0.418 ± 5.834E-02 | 0.0089 |
| e1Res (39 degree) | 0.470 ± 6.751E-02 | 0.407 ± 6.627E-02 | 0.010 |
| e2Res (39 degree) | 9.833E-02 ± 4.172E-02 | 6.132E-02 ± 2.396E-02 | 0.0085 |
| ePRes (106 degree) | 0.843 ± 0.344 | 1.35 ± 0.602 | 0.0014 |
| ePRes (107 degree) | 0.828 ± 0.280 | 1.18 ± 0.494 | 0.0061 |
| Wall Variability | 0.256 ± 0.193 | 0.484 ± 0.191 | 0.0017 |

Using the risk score without wall variability is given as: Cardiovascular Risk Score=K+e1Res38+e1Res39+e2Res39−ePRes106+ePRes107.

| Class | Asymptomatic | Symptomatic | P value |
|---|---|---|---|
| Risk Score | 6.03 ± 0.282 | 5.71 ± 0.312 | 0.0034 |

K was taken to be 5.0 for scaling reasons. This table shows that the risk score value for Symptomatic and Asymptomatic shows a scale of 5.7 compared to 6.0 without wall variability as a feature. The stability of score is partially dependent upon the number of cases used in the training set.

Using the wall variability as a feature, the risk score separation index between the Symptomatic vs. Asymptomatic with all the three grayscale features and wall variability feature included are shown in table as:

| Class | Asymptomatic | Symptomatic | P value |
|---|---|---|---|
| Risk Score | 5.77 ± 0.249 | 5.23 ± 0.449 | <0.0001 |

Cardiovascular Risk Score=K+(e1Res38−WallVariability (poly)+e1Res39+e2Rcs39−ePRes106+ePRes107) K was taken to be 5.0 for scaling reasons. This table shows that the risk score value for Symptomatic and Asymptomatic shows a scale of 5.2 compared to 5.7. The stability of score is partially dependent upon the number of cases used in the training set. The above numbers are with a low size data set of around 40 subjects.

Our protocol when tried on ultrasound plaque data (without wall region) and without wall variability can be seen in the publication (Rajendra U. Acharya & Oliver Faust & A. P. C. Alvin & S. Vinitha Sree & Filippo Molinari & Luca Saba & Andrew Nicolaides & Jasjit S. Suri, Symptomatic vs. Asymptomatic Plaque Classification in Carotid Ultrasound), Journal of Medical Systems, DOI 10.1007/s10916-010-9645-2. The publication shows the range of SACI (Risk Score) for symptomatic and asymptomatic cases as: 9.26 vs. 6.13 for Symptomatic vs. Asymptomatic.

Different types of risk scores can be obtained depending upon the feature set used.

Figure 10:
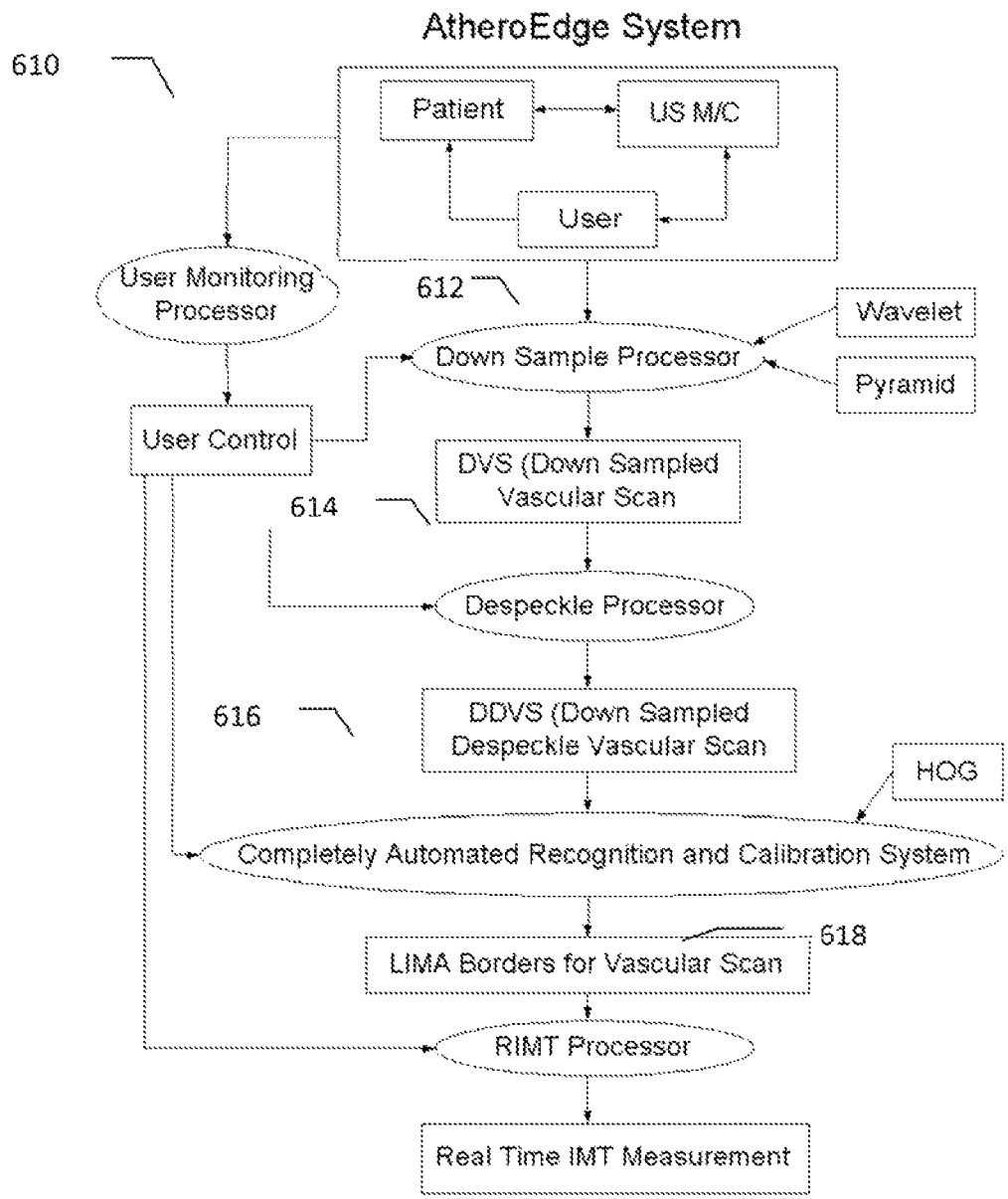
FIG. 10 shows the LIMA border extraction system (a class of AtheroEdge™ system), which is then used to create the Atherosclerotic Wall Region.

Border Estimation System in Longitudinal Carotids:

FIG. 10 shows the LIMA border extraction system which is then used to create the AWR. This is also called as AtheroEdge™ system. This AtheroEdge™ system is an edge detection system which finds the LI and MA edges of the artery far wall. It consists of three processors: (a) despeckle processor; (b) down sampling processor; and (c) Completely Automated Recognition and Calibration system and (d) AWR Estimation and IMT quantification system.

Figure 11:
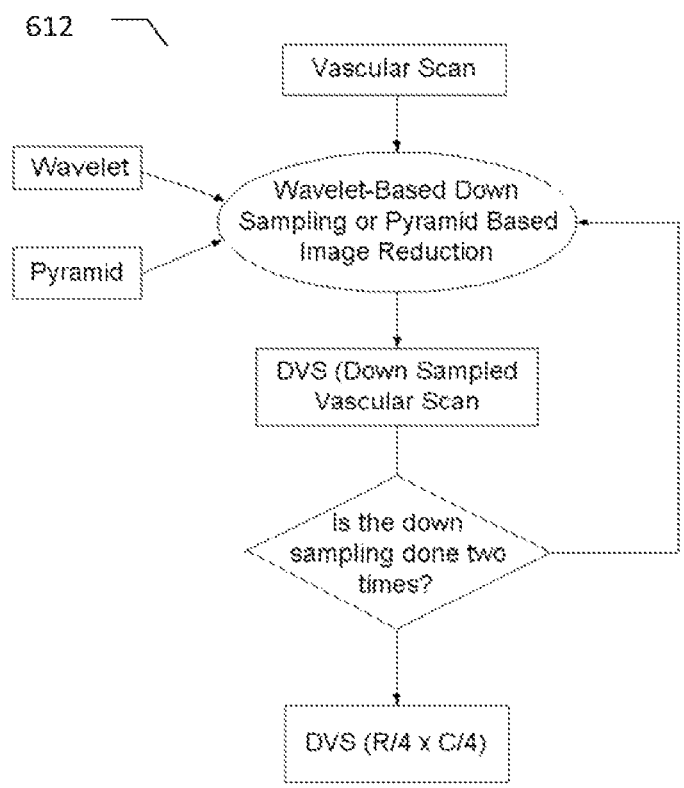
FIG. 11 Down Sampling Processor used in the LIMA border estimation Processor.

FIG. 11: Down Sampling Processor used in the LIMA border estimation processor. The FIG. 11 shows the down sampling or fine to coarse resolution system. One of the four systems can be used for fine to coarse sampling. The role of the multi-resolution process is to convert the image from fine resolution to coarse resolution. Those skilled in the art of down sampling any use off the shelf down sampling methods. One of the very good down samplers is Lanczos interpolation. This is based on the sine function which can be given mathematically as $$\mathrm{sinc}(x) = \frac{\sin(\pi x)}{\pi x}.$$

Since the sine function never goes to zero, practical filter can be implemented by taking the sine function and multiplying it by a "window", such as Hamming and Hann, giving an overall filter with finite size. We can define the Lanczos window as a sine function scaled to be wider, and truncated to zero outside of the main lobe. Therefore, Lanczos filter is a sine function multiplied by a Lanczos window. Three lobed Lanczos filter can be defined as $$\mathrm{Lanczos3}(x) = \begin{cases} \dfrac{\sin(\pi x)\sin\left(\pi \frac{x}{3}\right)}{\pi x \cdot \pi \frac{x}{3}}, & \text{if } |x| \leq 3 \\ 0, & \text{if } |x| > 3 \end{cases}$$

Although Lanczos interpolation is slower than other approaches, it can obtain the best interpolation results because Lanczos' method attempts to reconstruct the image by using a series of overlapping sine waves to produce what's called a "best fit" curve. Those skilled in the art of down sample can also use Wavelet transform filters as they are very useful for multi-resolution analysis. The orthogonal wavelet transform of a signal f can be formulated by $$f(t) = \sum_{k \in z} c_j(k) \varphi_{j,k}(t) + \sum_{J=1}^{J} \sum_{k \in Z} d_j(k) \varphi_{j,k}(t)$$

where the $c_j(k)$ is the expansion coefficients and the $d_i(k)$ is the wavelet coefficients. The basis function $\phi_{j,k}(t)$ can be presented as $$\phi_{j,k}(t) = 2^{-j/2}\phi(2^{-j}t-k),$$

where k, j are translation and dilation of a wavelet function φ(t). Therefore, wavelet transforms can provide a smooth approximation of f(t) at scale J and a wavelet decomposition at per scales. For 2-D images, orthogonal wavelet transforms will decompose the original image into 4 different sub-band (LL, LH, HL and MI).

Bicubic interpolation can also be used as it will estimates the value at a given point in the destination image by an average of 16 pixels surrounding the closest corresponding pixel in the source image. Given a point (x,y) in the destination image and the point (l,k) (the definitions of l and k are same as the bilinear method) in the source image, the formulae of bicubic interpolation is $$f(x, y) = \sum_{m=l-1}^{l+2} \sum_{n=k-1}^{k+2} g(m, n) \cdot r(m - l - dx) \cdot (dy - n + k),$$

where the calculation of dx and dy are same as the bilinear method. The cubic weighting function r(x) is defined as $$r(x) = \frac{1}{6}[p(x+2)^3 - 4p(x+1)^3 + 6p(x)^3 - 4p(x-1)^3],$$

where $p(x)$ is $$p(x) = \begin{cases} x & x > 0 \\ 0 & x \leq 0 \end{cases}$$

Bicubic approach can achieve a better performance than the bilinear method because more neighboring points are included to calculate the interpolation value.

Bilinear interpolator can also be used as it is very simple to implement. Mathematically, it is given as: if g represents a source image and f represents a destination image, given a point (x,y) in f, the bilinear method can be presented as:

$$f(x,y) = (1-dx)\cdot(1-dy)\cdot g(l,k) + dx\cdot(1-dy)\cdot g(l+1,k) + (1-dx)\cdot dy\cdot g(l,k+1) + dx\cdot dy\cdot g(l+1,k+1),$$

where $l = \lfloor x \rfloor$ and $k = \lfloor y \rfloor$, and the dx, dy are defined as dx=x−l and dy=y−k respectively. Bilinear interpolation is simple. However it can cause a small decrease in resolution and blurring because of the averaging nature.

Figure 12:
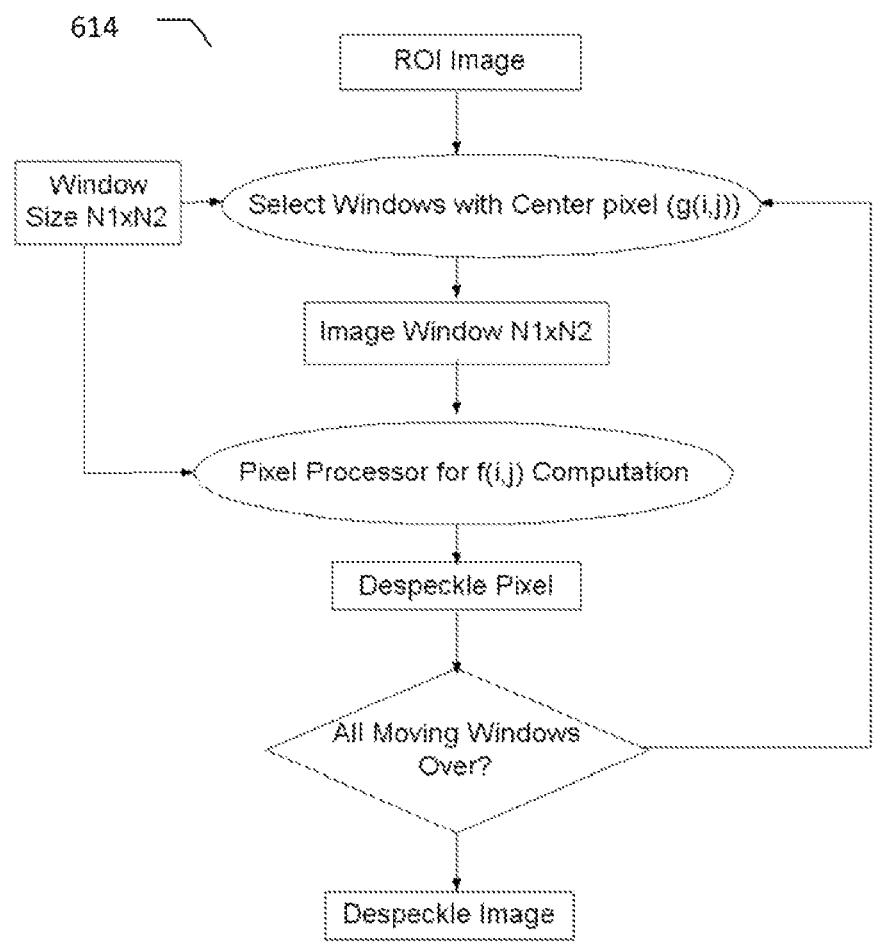
FIG. 12 De-speckle Processor which remove the speckles in the ultrasound region of interest. A moving window method is used for generating despeckle filtering process.

FIG. 12 shows the despeckle processor which remove the speckles in the ultrasound region of interest. A moving window method is used for generating despeckle filtering process. Speckle noise was attenuated by using a first-order statistics filter (named as lsmv by the authors), which gave the best performance in the specific case of carotid imaging. This filter is defined by the following equation:

$$J_{x,y} = \bar{I} + k_{x,y}(I_{x,y} - \bar{I}) \quad (1)$$

where, $I_{x,y}$ is the intensity of the noisy pixel, $\bar{I}$ is the mean intensity of a N×M pixel neighborhood and $k_{x,y}$ is a local statistic measure. The noise-free pixel is indicated by $I_{x,y}$. Mathematically $k_{x,y}$ is defined as $$k_{x,y} = \frac{\sigma_I^2}{\bar{I}^2 \sigma_I^2 + \sigma_n^2},$$

where $\sigma_I^2$ represents the variance of the pixels in the neighborhood, and $\sigma_n^2$ the variance of the noise in the cropped image. An optimal neighborhood size was shown to be 7×7.

Prior to despeckle filtering, the system crops the image in order to discard the surrounding black frame containing device headers and image/patient data. For DICOM image, we relied on the data contained in the specific field named SequenceOfUltrasnundRegions, which contains four sub-fields that mark the location of the image containing the ultrasound representation. These fields are named RegionLocation (their specific label is xmin, xmax, ymin and ymax) and they mark the horizontal and vertical extension of the image. The raw B-Mode image is then cropped in order to extract only the portion that contains the carotid morphology. Those skilled in the art of DICOM will know that if the image came in from other formats or if the DICOM tags were not fully formatted, one can adopt a gradient-based procedure. One can compute the horizontal and vertical Sobel gradient of the image. The gradients repeat similar features for the entire rows/columns without the ultrasound data: they are zero at the beginning and at the end. Hence, the beginning of the image region containing the ultrasound data can be calculated as the first row/column with gradient different from zero. Similarly, the end of the ultrasound region is computed as the last non-zero row/column of the gradient.

Figure 13:
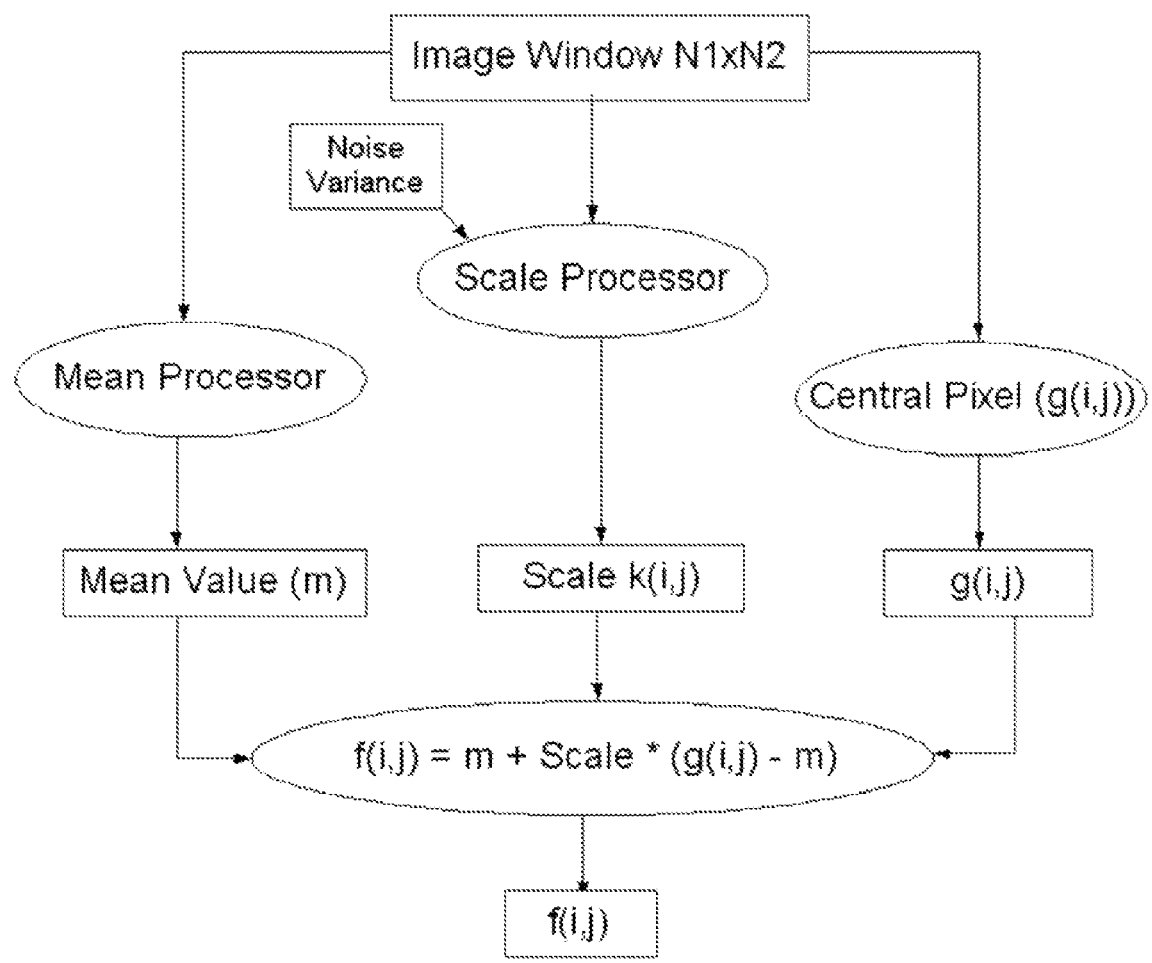
FIG. 13 shows the process for computing despeckle pixel and replacing the original noisy pixel. The process uses the scaling of the original pixel. The noise variance process is being used by the scale processor.

FIG. 13 shows the process for computing the despeckle pixel and replacing the original noisy pixel. The process uses the scaling of the original pixel. The noise variance process is being used by the scale processor.

Figure 14:
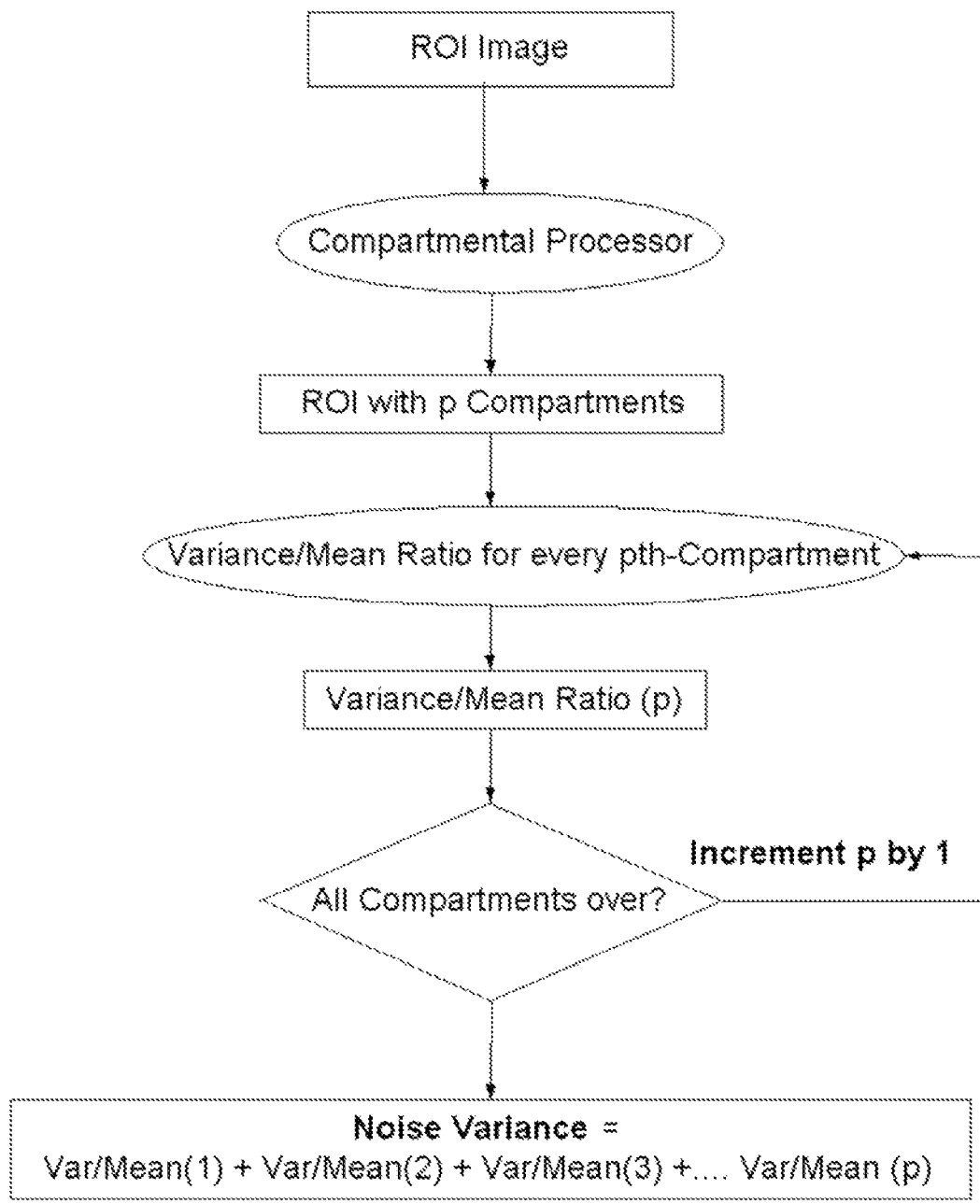
FIG. 14 shows the computation of the noise variance processor. The noise variance is computed by summing the variance to mean ration for all the compartments of the ROI region. The Figure shows if there are "p" compartments, then the noise variance is computed by summing the variance to mean ratio of each of the "p" compartments.

FIG. 14 shows the computation of the noise variance processor. The noise variance is computed by summing the variance to mean ratio for all the compartments of the ROI region. The Figure shows if there are "p" compartments, then the noise variance is computed by summing the variance to mean ratio of each of the "p" compartments.

Figure 15:
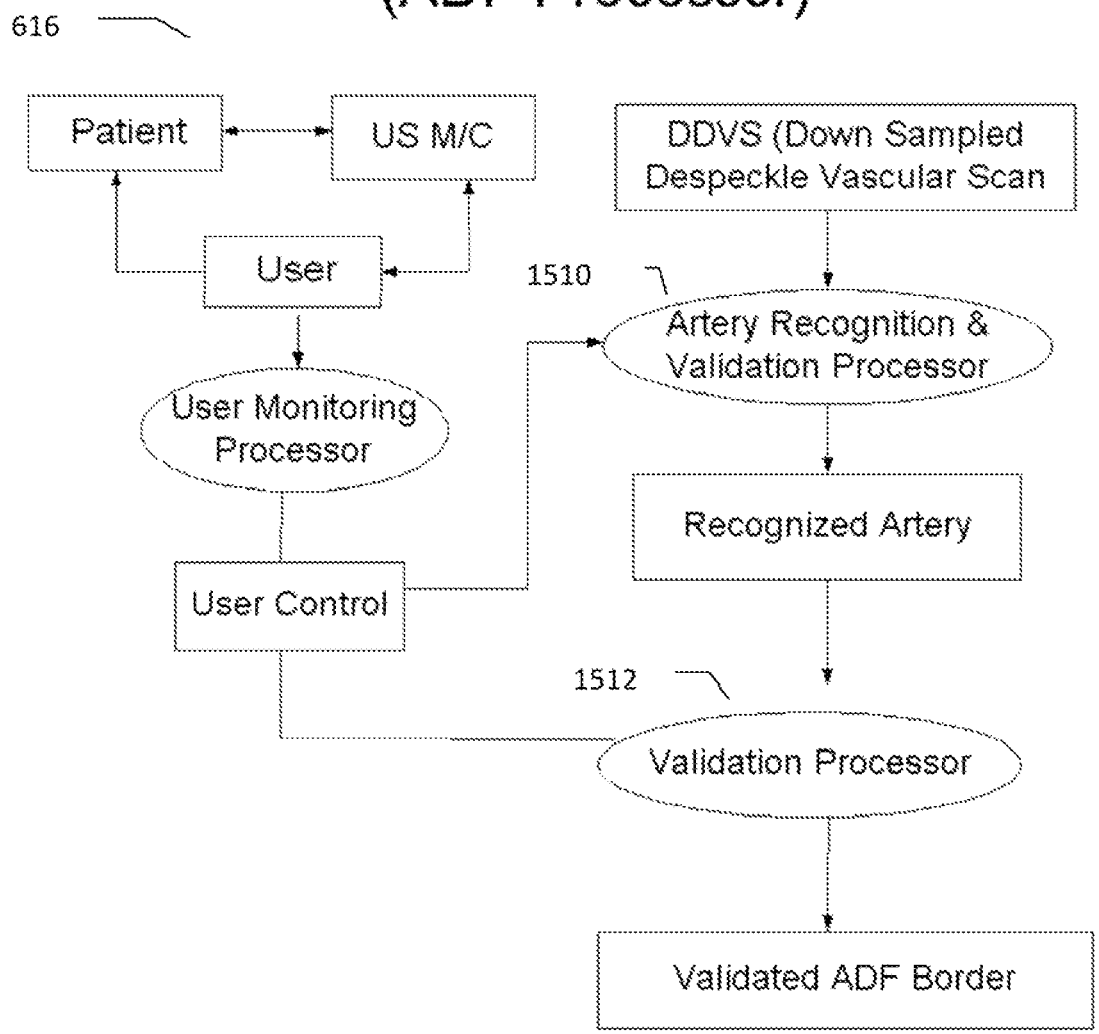
FIG. 15 shows the Artery Recognition and Validation Processor. It shows two phases: (a) recognition and validation processor for computing the LIMA borders after the automated recognition process and (b) Calibration phase is definite phase for any LIMA borders to be estimated along with the IMT values.

FIG. 15 shows the Artery Recognition and Validation Processor. It shows two phases: (a) recognition and validation processor for computing the LIMA borders after the automated recognition process and (b) Calibration phase is definite phase for any LIMA borders to be estimated along with the IMT values. Recognition and validation process consists as follows:

Higher order Gaussian derivative filter: The despeckled image is filtered by using a first order derivative of a Gaussian kernel filter. It is possible to observe how the CA walls become enhanced to white. The sigma parameter of the Gaussian derivative kernel was taken equal to 8 pixels, i.e. to the expected dimension of the IMT value. In fact, an average IMT value of say 1 mm corresponds to about 16 pixels in the original image scale and, consequently, to 8 pixels in the down-sampled scale.

$AD_F$ refinement using anatomic information and spike removal. Pilot studies showed that the traced $AD_F$ profile could be characterized by spikes and false points identification. This could be due to several reasons such as variations in intensities, gaps in the media walls, presence of jugular vein, shadow effects or combination of these. This innovation, therefore introduced a validation protocol, which provides a check on the far adventitia ($AD_F$) profile ensuring that the location of carotid artery is at correct place and the segmentation edge is not very bumpy. This validation step refines the far adventitia ($AD_F$) profile and is done in two steps: (a) refinement using anatomic lumen and (b) spike removal.

Refinement by anatomic reference (Lumen). This check has been introduced to avoid error conditions of $AD_E$ curve protruding into the lumen vessel. Thus, the refinement step requires the identification of the lumen region automatically. We have modeled the lumen segmentation region as a classification process with two classes. Carotid characteristics can be thought of as a mixture model with varying intensity distributions. This is because (a) the pixels belonging to the vessel lumen are characterized by low mean intensity and low standard deviation; (b) pixels belonging to the adventitia layer of the carotid wall are characterized by high mean intensity and low standard deviation; and (c) all remaining pixels should have high mean intensity and high standard deviation. As a result of this distribution, the application derives a bi-dimensional histogram (2DH) of the carotid image. For each pixel, we considered a 10×10 neighborhood of which one can calculate the mean value and the standard deviation. The mean values and the standard deviations were normalized to 0 and 1 and were grouped into 50 classes each having an interval of 0.02. The 2DH was then a joint representation of the mean value and standard deviation of each pixel neighborhood. It is well established that pixels belonging to the lumen of the artery are usually classified into the first classes of this 2DH: expert sonographer manually traced the boundaries of the CCA lumen and observed the distribution of the lumen pixels on the 2DH. Overall results revealed that pixels of the lumen have a mean values classified in the first 4 classes and a standard deviation in the first 7 classes. We therefore consider a pixel as possibly belonging to the artery lumen if its neighborhood intensity is lower than 0.08 and if its neighborhood standard deviation is lower than 0.14. This method shows how the local statistic is effective in detecting image pixels that can be considered as belonging to the CCA lumen. The $AD_F$ points along the CA are considered one by one. For each $AD_F$ point:

1. We consider the sequence of the 30 pixels above it (i.e., the 30 pixels located above the $AD_F$ point, towards the top of the image, and, therefore, with lower row indexes). Those skilled in the art can choose a different than 30 pixels depending upon the pixel density and resolution of the image.
2. The $AD_F$ point failed the lumen test, if the $AD_F$ point crosses the lumen region and has penetrated the lumen region by at least 30 pixels inside the lumen or more. These failed points must not belong to the $AD_F$ boundary. These $AD_F$ points which fail the lumen test are tagged as 0, while rest of the points are tagged as 1. $AD_F$ All the $AD_F$ points that tagged as 0 are deleted from the $AD_F$ list.
3. The procedure is repeated for each $AD_F$ point along the CA artery.

Note that even though, the lumen anatomic information, which acts as a reference, provides a good test for catching a series of wrongly computed ADF boundary, it might slip from sudden bumps which may be due to the changes in grayscale intensity due presence of unusual high intensity in lumen region or a calcium deposit in the near wall causing a shadow in far wall region. This sudden spike can then be easily detected ahead using the spike detection method. This improves the accuracy of the system which in turn helps in determination of the correct region of interest and thus the classification accuracy.

Spike detection and removal. We implemented an intelligent strategy for spike detection and removal. Basically, we compute the first order derivative of the $AD_F$ profile and check for values higher than 15 pixels. This value was chosen empirically by considering the image resolution. When working with images having approximate resolution of about 0.06 min/pixel, an IMT value of 1 mm would be about 17 pixels. Therefore, a jump in the $AD_F$ profile of the same order of magnitude of the IMT value is clearly a spike and error condition. If the spike is at the very beginning of the image (first 10 columns) or at the end (last 10 columns), then the spiky point is simply deleted. Otherwise, all spikes are considered and either substituted by a neighborhood moving average or removed.

Far adventitia automated tracing. Heuristic search applied to the intensity profile of each column. Starting from the bottom of the image (i.e. from the pixel with the higher row index), we searched for the first white region of at least 6 pixels of width. The deepest point of this region (i.e. the pixel with the higher row index) marked the position of the far adventitia ($AD_F$) layer on that column.

The sequence of all the points of the columns constituted the overall $AD_F$ automatically generated tracing. Finally, the $AD_F$ profile was up-sampled to the original scale and overlaid to the original image. At this stage, the CA far wall is automatically located in the image frame and automated segmentation is made possible. The parameter table for stage I of the LIMA border estimation is shown in FIG. 32.

Figure 16:
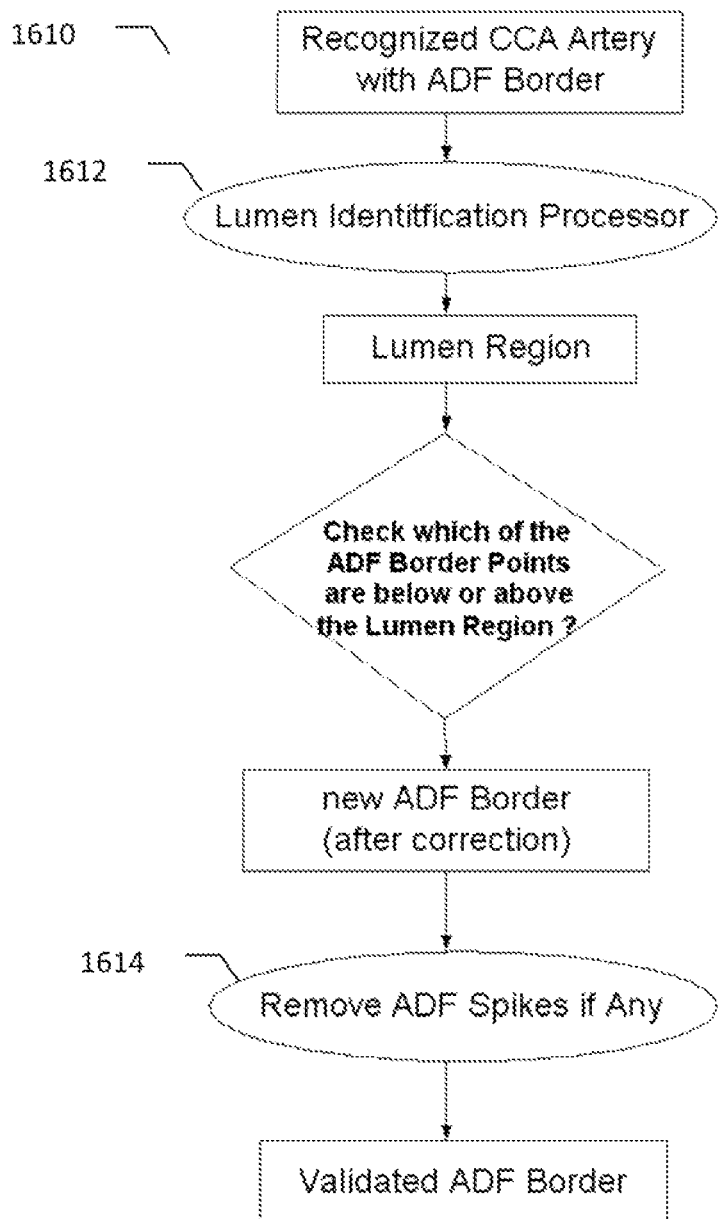
FIG. 16 shows the validation Processor.

FIG. 16 shows the validation processor.

Figure 17:
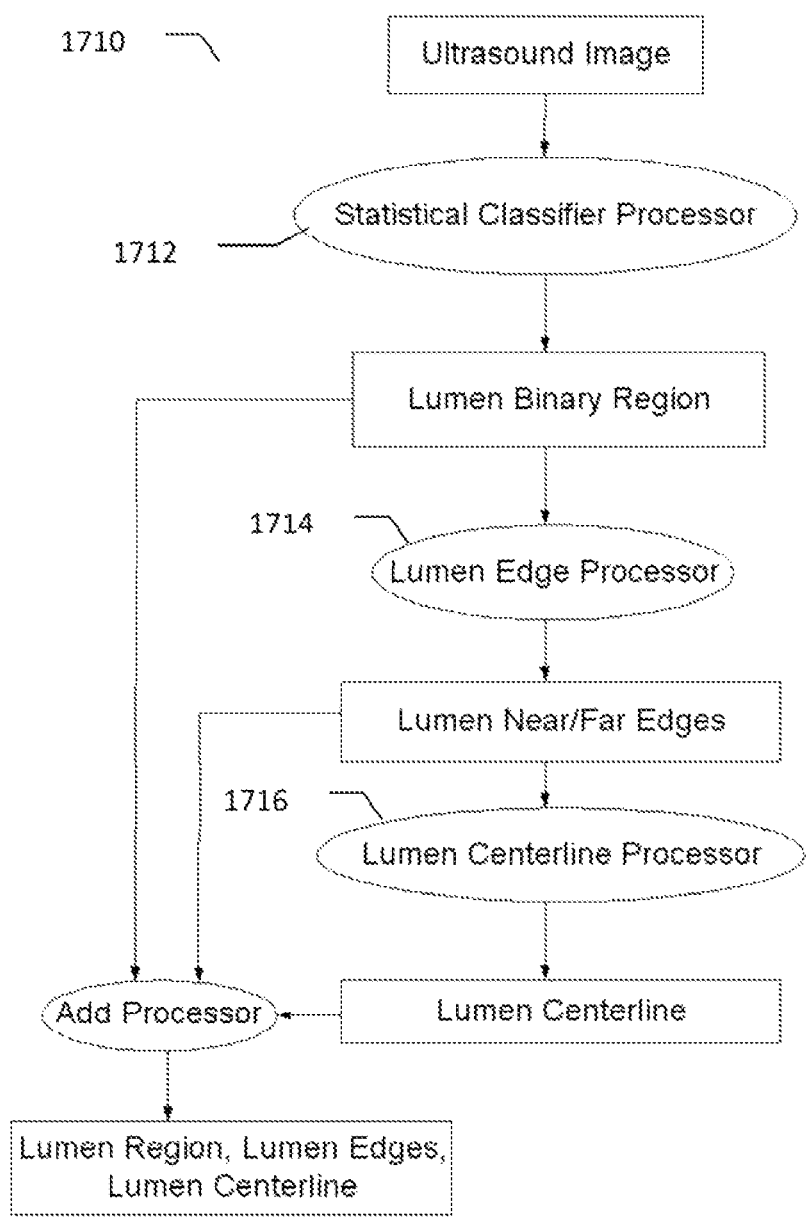
FIG. 17 shows the Lumen Identification Processor. It consists of three phases: (a) Lumen Classifier Processor; (b) Lumen Edge Processor; and (c) Lumen Middle line Processor.

FIG. 17 shows the Lumen Identification Processor. It consists of three phases: (a) Lumen Classifier Processor; (b) Lumen Edge Processor; and (c) Lumen Middle line Processor.

Figure 18:
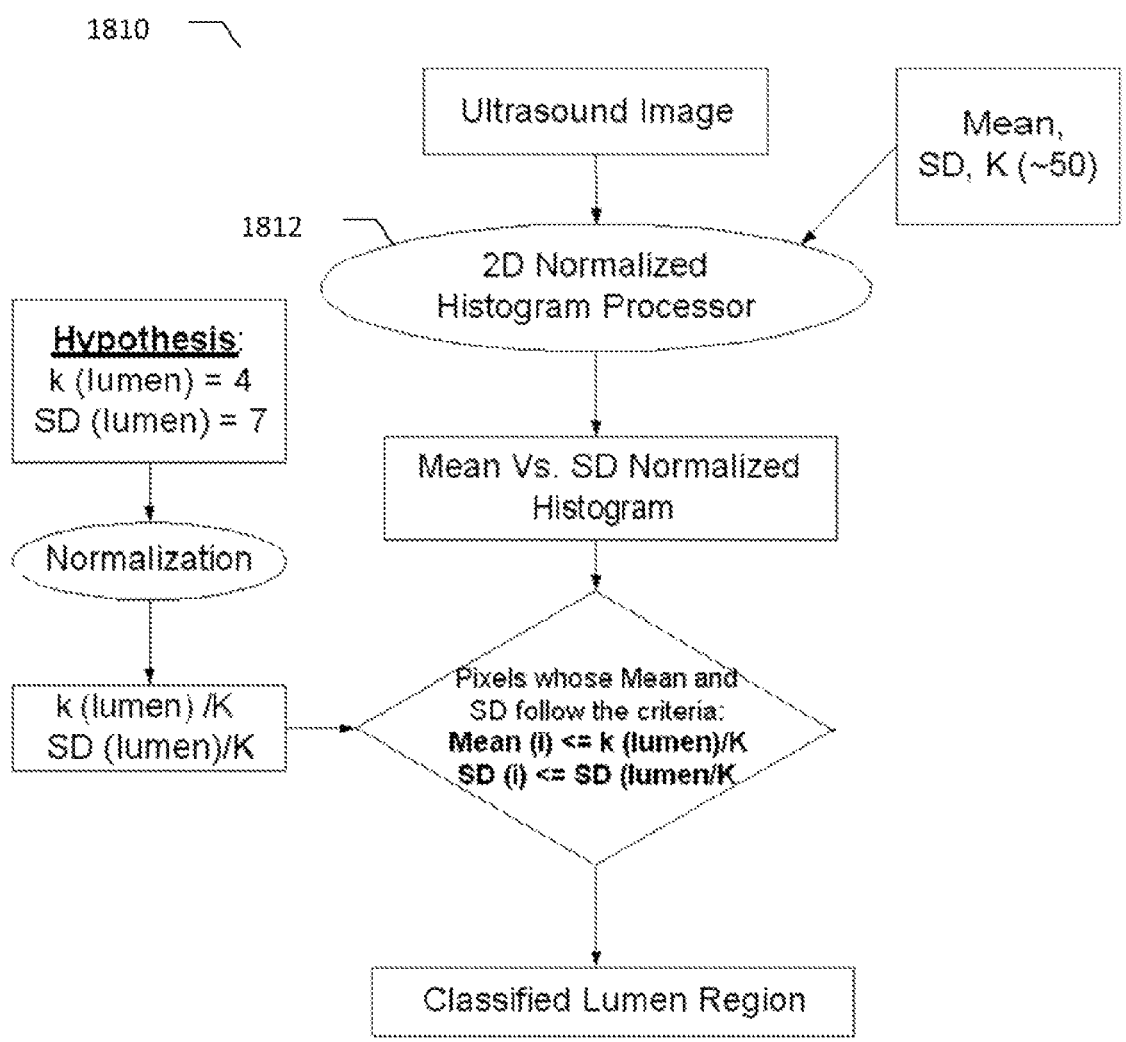
FIG. 18 Lumen Classifier Systems.

FIG. 18 Lumen Classifier Systems.

LIMA Border Estimation for AWR Computation/Segmentation Stage (Stage II):

Here we use any of the existing methods for computation of the LI and MA borders given the region of interest or Guidance Zone. The following citations can be used for computation of the LI/MA borders and its corresponding IMT measurement:

F. Molinari, G. Zeng, and J. S. Suri, An integrated approach to computer-based automated tracing and its validation for 200 common carotid arterial wall ultrasound images: A new technique, J Ultras Med, 29, (2010), 399-418.

F. Molinari, G. Zeng, and J. S. Suri, Intima-media thickness: setting a standard for completely automated method for ultrasound, IEEE Transaction on Ultrasonics Ferroelectrics and Frequency Control, 57(5), (2010), 1112-1124.

S. Delsanto, F. Molinari, P. Giustetto, W. Liboni, S. Badalamenti, and J. S. Suri, Characterization of a Completely User-Independent Algorithm for Carotid Artery Segmentation in 2-D Ultrasound Images, Instrumentation and Measurement, IEEE Transactions on, 56(4), (2007), 1265-1274.

S. Delsanto, F. Molinari, P. Giustetto, W. Liboni, and S. Badalamenti, CULEX-completely user-independent layers extraction: ultrasonic carotid artery images segmentation, Conf Proc IEEE Eng Med Biol Soc, 6, (2005), 6468-71.

S. Delsanto, F. Molinari, W. Liboni, P. Giustetto, S. Badalamenti, and J. S. Suri, User-independent plaque characterization and accurate IMT measurement of carotid artery wall using ultrasound, Conf Proc IEEE Eng Med Biol Soc, 1, (2006), 2404-7.

F. Molinari, S. Delsanto, P. Giustetto, W. Liboni, S. Badalamenti, and J. S. Suri, User-independent plaque segmentation and accurate intima-media thickness measurement of carotid artery wall using ultrasound, in, Number of 111-140 (2008, Artech House, Norwood, Mass., 20081).

F. Molinari, W. Liboni, P. Giustetto, E. Pavanelli, A. Marsico, and J. Suri, Carotid plaque characterization with contrast-enhanced ultrasound imaging and its histological validation, The Journal for Vascular Ultrasound, 34(4), (2010), 1-10.

F. Molinari, C. Loizou, G. Zeng, C. Pattichis, D. Chandrashekar, M. Pantziaris, W. Liboni, A. Nicolaides, and J. Suri, *Completely Automated Multi-Resolution Edge Snapper (CAMES)—A New Technique for an Accurate Carotid Ultrasound IMT Measurement and its Validation on a Multi-Institutional Database*, in *SPIE Medical Imaging Conference*. 2011: Lake Buena Vista (Orlando), Fla., USA.

Figure 19:
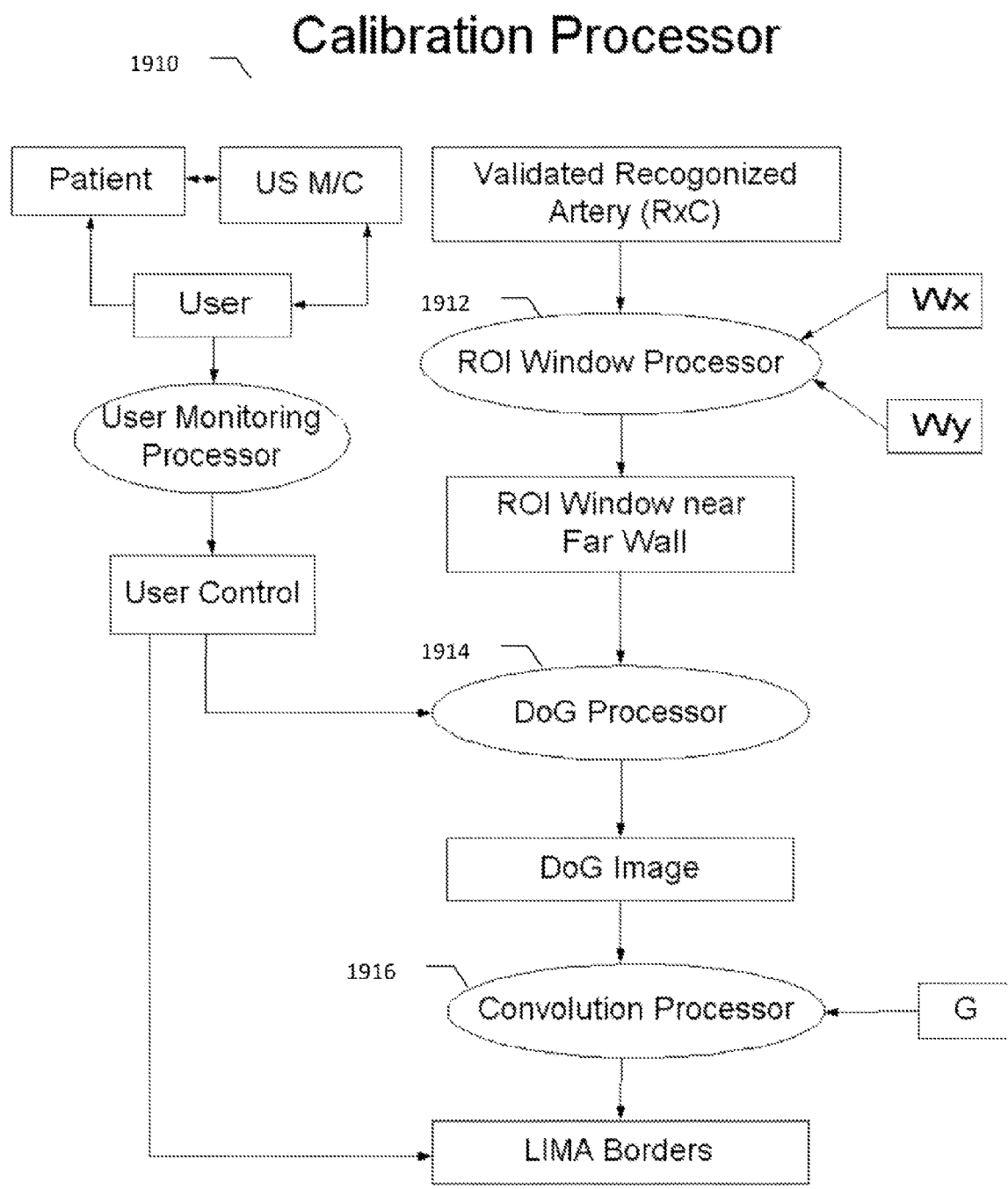
FIG. 19 Calibration Processor (stage II of the AWR Processor).

FIG. 19 Calibration Processor (stage II of the LIMA processor) a typical LIMA processor.

Figure 20:
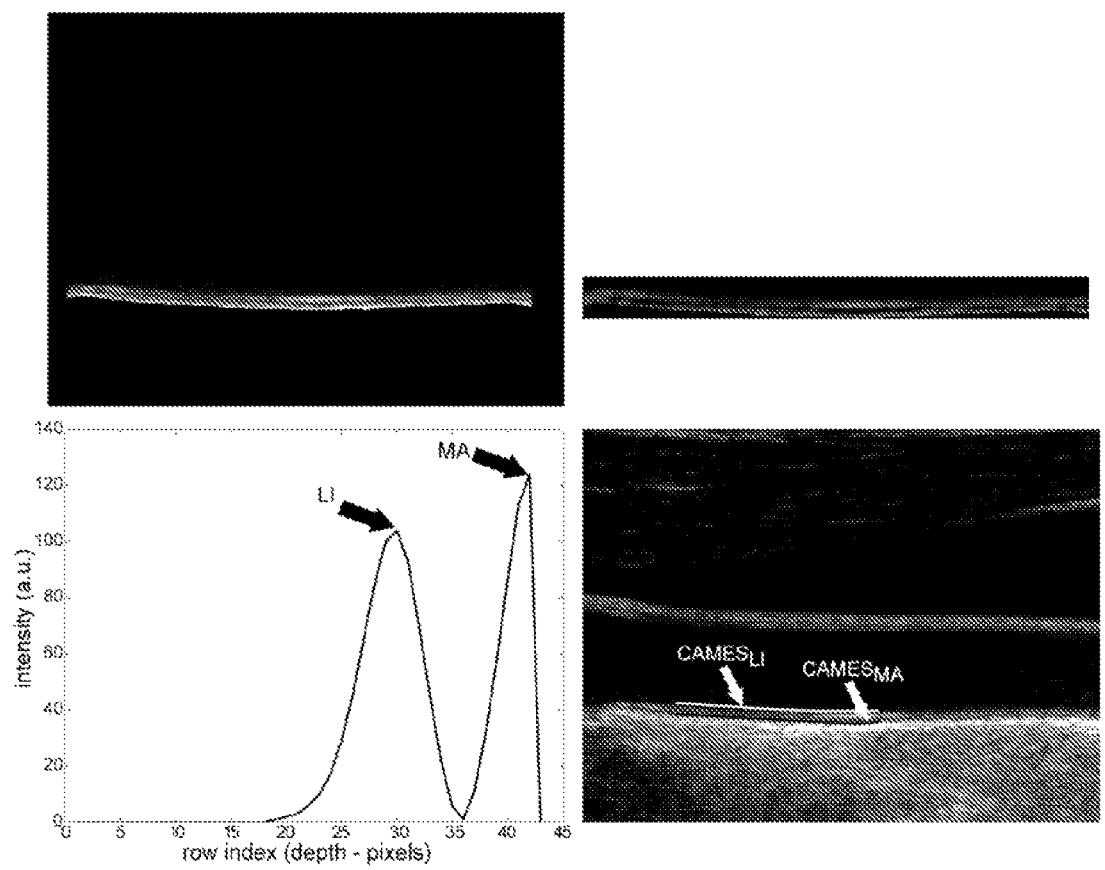
FIG. 20 shows the Peak detector for stage II using the multi-resolution framework.

FIG. 20 Stage II for peak identification of LI and MA borders in the region of interest.

The Calibration process of type II (using Edge Flow Calibration Processor). This shows the domain based calibration process or segmentation processor. The system is divided into three components: (a) Guidance Zone Processor; (b) DoG Filtering Processor; (c) Heuristic Processor. Since the Artery Recognition Processor has identified the adventitia tracing ADF, the calibration needs to be applied in the zone which was initially guided by the Artery Recognition Processor. Since the calibration stage is merely a combination of finding the edges of the LI and MA borders, the importance of guidance zone is very crucial. The Guidance Zone is the key to avoid the false peaks estimation in the calibration phase.

The Guidance Zone is built around the adventitia tracing ADF. The Guidance Zone is a region-of-interest (ROI) around the automatically traced ADF profile, so called the domain region in which segmentation will run. The ROI is designed such that it has the same width as of the ADF curve. This will allow the creation of the largest possible ROI, according to the detected length of the adventitia layer. The height has to be equal to 30 pixels (1.8 mm for images with 16.67 pixels/mm of density, and 1.875 mm for images with 16 pixels/mm of density). For each point of the ADF profile we considered as upper limit of the ROI the pixel with a row index of 30 pixels lower, towards the upper edge of the cropped image. Substantially, the bottom limit of the ROI was the ADF curve while the upper limit was ADF shifted by 30 pixels. Those skilled in the art can use the pixel density to compute the height of the ROI given the ADF border.

Edge Flow Magnitude and Edge Flow Direction (stage II):

We use the method developed by W. Y. Ma and B. S. Manjunath (citation: Ma, W. Y. and B. S. Manjunath. *Edge Flow: A Framework of Boundarik Detection and Image Segmentation. in Computer Society Conference on Computer Vision and Pattern Recognition.* 1997. San Juan). that facilitates the integration of different image attributes into a single framework for boundary detection and is based on the construction of an edge flow vector defined as:

$$F(s,\theta)=F[E(s,\theta), P(s,\theta), P(s,\theta+\pi)] \qquad (2)$$

where:
$E(s,\theta)$ is the edge energy at location s along the orientation $\theta$;
$P(s,\theta)$ represents the probability of finding the image boundary if the corresponding edge flow "flows" in the direction $\theta$;
$P(s,\theta+\pi)$ represents the probability of finding the image boundary if the edge flow "flows" backwards, i.e., in the direction $\theta+\pi$.

The final single edge flow vector can be thought of as the combination of edge flows obtained from different types of image attributes. The image attributes that we considered are intensity and texture. In order to calculate the edge energy and the probabilities of forward and backward edge flow direction, a few definitions must first be clarified, specifically the first derivative of Gaussian (GD) and the difference of offset Gaussian (DOOG).

Considering the Gaussian kernel $G_\sigma(x,y)$, where $\sigma$ represents the standard deviation, the first derivative of the Gaussian along the x-axis is given by $$GD_\sigma(x, y) = -\left(\frac{x}{\sigma^2}\right)G_\sigma(x, y) \qquad (3)$$

and the difference of offset Gaussian (DOOG) along the x-axis is defined as:

$$DOOG_\sigma(x,y)=G_\sigma(x,y)-G_\sigma(x+d,y) \qquad (4)$$

where d is the offset between centers of two Gaussian kernels and is chosen proportional to $\sigma$. This parameter is significant in the calculation of the probabilities of forward and backward edge flow, as it is used to estimate the probability of finding the nearest boundary in each of these directions. By rotating these two functions, we can generate a family of previous functions along different orientations $\theta$ and they can be denoted as $G_{\sigma,\theta}(x,y)$ and $DOOG_{\sigma,\theta}(x,y)$, respectively:

$$GD_{\sigma,\theta}(x,y)=GD_\sigma(x',y') \qquad (5)$$

$$DOOG_{\sigma,\theta}(x,y)=DOOG_\sigma(x',y') \qquad (6)$$

where: $x'=x \cos \theta + y \sin \theta$, and $y'=-x \sin \theta + y \cos \theta$ Intensity Edge Flow (of Stage II):

Considering the original image I(x,y) at a certain scale $\sigma$, $I_\sigma(x,y)$ is obtained by smoothing the original image with a Gaussian kernel $G_\sigma(x,y)$. The edge flow energy $E(s,\theta)$ at scale $\sigma$, defined to be the magnitude of the gradient of the smoothed image $I_\sigma(x,y)$ along the orientation $\theta$, can be computed as $$E(s,\theta)=|I(x,y)*GD_{\sigma,\theta}| \qquad (7)$$

where s is the location (x,y). This energy indicates the strength of the intensity changes. The scale parameter is very important in that it controls both the edge energy computation and the local flow direction estimation so that only edges larger than the specified scale are detected.

To compute $P(s,\theta)$, two possible flow directions ($\theta$ and $\theta+\pi$) are considered for each of the edge energies along the orientation $\theta$ at location s. The prediction error toward the surrounding neighbors in these two directions can be computed as:

$$Error(s,\theta)=|I_\sigma(x+d \cos \theta, y+d \sin \theta)-I_\sigma(x,y)|=|I(x,y)* DOOG_{\sigma,\theta}(x,y)| \qquad (8)$$

where d is the distance of the prediction and it should be proportional to the scale at which the image is being analyzed. The probabilities of edge flow direction are then assigned in proportion to their corresponding prediction errors, due to the fact that a large prediction error in a certain direction implies a higher probability of locating a boundary in that direction:

$$P(s, \theta) = \frac{Error(s, \theta)}{Error(s, \theta) + Error(s, \theta + \pi)} \qquad (9)$$

Texture Edge Flow: Texture features are extracted from the image based on Gabor decomposition. This is done basically by decomposing the image into multiple oriented spatial frequency channels, and then the channel envelopes (amplitude and phase) and used to form the feature maps.

Given the scale $\sigma$, two center frequencies of the Gabor filters (the lowest and the highest) are defined and based on the range of these center frequencies, an appropriate number of Gabor filters $g_i(x,y)$ is generated. The complex Gabor filtered images are defined as:

$$O_i(x,y)=I*g_i(x,y)=m_i(x,y)\exp[\Phi_i(x,y)] \qquad (10)$$

where $1 \le i \le N$, N is the total number of filters and i is the sub band, $m_i(x,y)$ is the magnitude, and $\Phi_i(x,y)$ is the phase. A texture feature vector $\Psi(x,y)$ can then be formed by taking the amplitude of the filtered output across different filters at the same location (x,y):

$$\Psi(x,y)=[m_1(x,y),m_2(x,y),\ldots,m_N(x,y)] \qquad (11)$$

The change in local texture information can be found using the texture features, thus defining the texture edge energy:

$$E(s, \theta) = \sum_{1 \leq i \leq N} |m_i(x, y) * GD_{\sigma,\theta}(x, y)| \cdot w_i \quad (12)$$

where $$w_i = \frac{1}{\|\alpha_i\|}$$

and $\|\alpha_i\|$ is the total energy of the sub band i.

The direction of the texture edge flow can be estimated similarly to the intensity edge flow, using the prediction error:

$$\text{Error}(s, \theta) = \sum_{1 \leq i \leq N} |m_i(x, y) * DOOG_{\sigma,\theta}(x, y)| \cdot w_i \quad (13)$$

and the probabilities $P(s,\theta)$ of the flow direction can be estimated using the same method as was used for the intensity edge flow.

Combining Edge Flow from Intensity and Texture (Stage II):

For general-purpose boundary detection, the edge flows obtained from the two different types of image attributes can be combined:

$$E(s, \theta) = \sum_{a \in A} E_a(s, \theta) \cdot w(a), \quad \sum_{a \in A} w(a) = 1 \quad (14)$$

$$P(s, \theta) = \sum_{a \in A} P_a(s, \theta) \cdot w(a) \quad (15)$$

where $E_a(s,\theta)$ and $P_a(s,\theta)$ represent the energy and probability of the edge flow computed from the image attributes a (in this case, it is intensity and texture). w(a) is the weighting coefficient among various types of image attributes. To identify the best direction for searching for the nearest boundary, we are supposed to have edge flows $\{F(s,\theta)|_{0 \leq \theta \leq \pi}\}$ and identify a continuous range of flow directions which maximizes the sum of probabilities in that half plane:

$$\Theta(s) = \arg\max_{\theta} \left\{ \sum_{\theta \leq \theta' \leq \theta + \pi} P(s, \theta') \right\} \quad (16)$$

The vector sum of the edge flows with their directions in the identified range is what defines the final resulting edge flow and is given by:

$$\vec{F}(s) = \sum_{\Theta(s) \leq \theta \leq \Theta(s) + \pi} E(s, \theta) \cdot \exp(j\theta) \quad (17)$$

where $\vec{F}(s)$ is a complex number whose magnitude represents the resulting edge energy and whose angle represents the flow direction.

Flow Propagation and Boundary Detection (Stage II):

Once the edge flow $\vec{F}(s)$ of an image is computed, boundary detection can be performed by iteratively propagating the edge flow and identifying the locations where two opposite direction of flows encounter each other. The local edge flow is then transmitted to its neighbor in the direction of flow if the neighbor also has a similar flow direction. The steps which describe this iterative process are as follows:

STEP 1: Set n=0 and $\vec{F}_0(s) = \vec{F}(s)$
STEP 2: Set the initial edge flow $\vec{F}_{n+1}(s)$ at time n+1 to zero
STEP 3: At each image location s=(x,y), identify the neighbour s'=(x',y') which is in the direction of edge flow $\vec{F}_n(s)$
STEP 4: Propagate the edge flow if $\vec{F}_n(s') \cdot \vec{F}(s) > 0$
$\vec{F}_{n+1}(s') = \vec{F}_{n+1}(s') + \vec{F}_n(s)$:
otherwise.
$\vec{F}_{n+1}(s) = \vec{F}_{n+1}(s) + \vec{F}_n(s)$
STEP 5: If nothing has been changed, stop the iteration. Otherwise, set n=n+1 and go to step 2.

The image boundaries can then be detected once the edge flow propagation reaches a stable set by identifying the locations which have non-zero edge flow coming from two opposing directions. For all of the images, we considered 8 different orientations, starting from 0° and going to 315° with equal degree intervals in between.

Once the image boundaries are detected, the final image is generated by performing region closing on it to limit the number of disjoint boundaries by searching for the nearest boundary element, which is within the specified search neighborhood at the unconnected ends of the contour. If a boundary element is found, a smooth boundary segment is generated to connect the open contour to another boundary element. The neighborhood search size is taken to be proportional to the length of the contour itself.

This approach of edge detection has some very salient features, including the fact that it uses a predictive coding model for identifying and integrating the different types of image boundaries, the boundary detection is based on flow field propagation and it has very few "free" parameters that control the segmentation. Because of this, very little parameter tuning or selection is needed and the sole parameter that controls the segmentation is the preferred image scale.

The edge flow algorithm can over-segments in many different points, due partly to the fact that the image can be cropped to contain the entire Guidance Zone Mask and therefore may contain sections of the image that can be found below the ADF profile. Also, while part of the MA and LI edge estimation may be done using the edge flow algorithm, the segmentation cannot yet be considered complete as there are still some missing MA and LI edges and the edges found must be classified as either belonging to the MA profile or the LI profile. This refinement and classification process is done using a strong dependency on the edges found by the edge flow algorithm and via labeling and connectivity, which will be explained in further detail in the next two sections.

Small Edge Objects (stage II):

Secondly, since there can still be small unwanted edge objects around the interested area, small edge objects are defined as those which have an area ratio below a certain limit φ and are subsequently removed from the image. The area ratio is defined by the following equation:

$$AreaRatio = \frac{Area_{EdgeObject}}{Area_{AllEdgeObjects}} \leq \phi \Rightarrow SmallEdgeObject \quad (18)$$

MA Estimation:

Our experimental data showed that, when φ=0.1 we are successfully able to discard the small edge objects. The MA segment is then first initialized as being the edge object with the highest pixel row index (i.e., the lowest edge object in the image) and its unconnected end points are found as the right top and left top pixels of the edge object (RTMA and LTMA, respectively). The remaining edge objects are then sorted by their mean pixel row index value so as to examine the edge objects starting from those which are lowest in the image and working upwards. The edge objects are then classified by following these steps:

1. Find the unconnected end points of the i-th edge object as the right top and left top pixels of the examined edge object ($RT_i$ and $LT_i$, respectively).
2. Determine the correct unconnected end point pair (either $LT_{MA}$ and $RT_i$ or $LT_i$ and $RT_{MA}$) as the pair which yields a lesser column difference in absolute value:

$$\left| LT_{x_{MA_i}} - RT_{x_{i_{MA}}} \right| \qquad (19)$$

3. Calculate the respective row distance in absolute value ($|LT_y-RT_y|$) and column distance ($LT_x-RT_x$) between the correct unconnected end point pair found and determine that the examined edge object can be classified as being part of the MA segment if the following two conditions are met:

$$|LT_y - RT_y| \leq \sigma \qquad (20)$$

$$LT_x - RT_x > 0 \qquad (21)$$

where $\phi$ is the maximum row distance acceptable, which we took to be equal to 15. The condition on the column distance is needed to ensure that the edge object considered does not overlap the already existing MA segment, while the condition on the row distance is necessary so as to avoid including edges that are too far above the existing MA segment.
4. Find new unconnected end points of the MA segment.
5. Repeat steps 1-4 until all edge objects have been examined.

Once all of the edge objects have been examined, those which are classified as being part of the MA segment are then connected together and regulated using a B-spline to produce the final MA profile.

LI Weak/Missing Edge Estimation using LI Strong Edge Dependency and Complete MA Edge Dependency (Stage II)

The LI missing edge estimation is completely dependent on the MA profile which is determined in previous stage. In fact, the MA profile is used to create a guidance zone starting from the profile and extending it upwards 50 pixels. This is used so as to find solely the edge objects from the image output of the edge flow algorithm that can be found above (lower row value) the MA profile and that have at least some common support with it Once this step is done, the following steps are necessary for each of these i edge objects:

1. Find the common support between the MA profile and the i-th edge object and cut the MA profile to the common support ($MAcut_i$).
2. Create a mask starting from $MAcut_i$ and extending it upwards 10 pixels and calculate the mean ($IM_{mask_{t,T}}$ and standard deviation ($IM_{std_{t,T}}$) of the pixel values found in the mask.
3. Create a second mask starting from $MAcut_i$ and extending it up to the i-th edge object. For each pixel found in this mask, determine if it can be defined as an acceptable pixel based on the following equation:

$$|PixelValue - IM_{mean_{t,T}}| < IM_{std_{t,T}} \Rightarrow AcceptablePixel \qquad (22)$$

and determine an $IM_{ratio}$ as the ratio between the number of acceptable pixels found and the total number of pixels considered.
4. Calculate the row distance between the left unconnected end point of the i-th edge object and the first point of $MAcut_i$ ($LT_{y_i} - LT_{y_{Mi}}$) and the row distance between the right unconnected end point of the i-th edge object and the last point of $MAcut_i$ ($RT_{y_i} - RT_{y_{MA}}$).
5. Determine that the edge object can be classified as being part of the LI segment if the following two conditions are met:

$$IM_{ratio} > 0.4 \qquad (23)$$

$$\text{mean}(LT_{y_i} - LT_{y_{MA}}, RT_{y_i} 31 RT_{y_{MA}}) > 5 \qquad (24)$$

The first condition is important in that it avoids classifying an edge object which is found in the lumen since the pixel values in the lumen are considerably lower than $IM_{mean_{Gi}}$ and those pixels would therefore not be classified as an acceptable pixel, lowering by a good deal the calculated $IM_{ratio}$. The second condition is necessary so as to not include over-segmented edge objects, which are located too close to the MA profile (i.e., in between the MA and LI profiles.)
6. Repeat steps 1-5 until all edge objects are examined.

Once all of the edge objects are examined, those found to be part of the LI segment (good edge objects) must be tested to see if the distance between two adjacent edges objects is too vast. This is to avoid connecting two edge objects which are too far from each other, which could have a negative effect on the outcome of the final LI profile.

To do this, the good edge objects are considered by adjacent pairs. The Euclidean distance between the two closest unconnected end points of the pair is calculated and if this distance exceeds a certain limit, the good edge objects are classified as belonging to two different LI segments. If the distance calculated is less than the defined limit, then the pair is classified as belonging to the same LI segment. Once all good edge objects have been examined, the final LI segment is determined by those that are part of the longest LI segment found.

The edge objects that are part of the final LI segment are then connected together and regulated using a B-spline to produce the final LI profile.

Figure 21A:
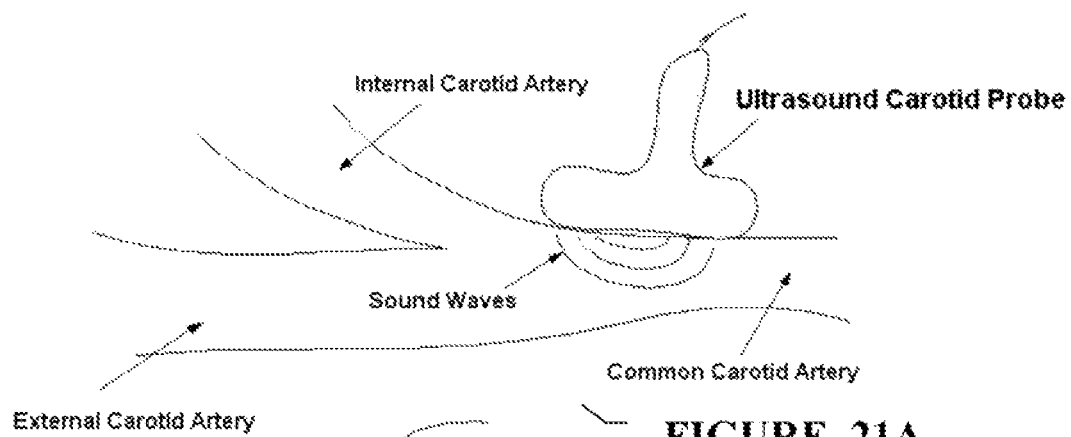
FIG. 21A shows the ultrasound scanning of the Carotid Artery. This can be a common carotid artery (CCA) or an internal carotid artery (ICA).
Figure 21B:
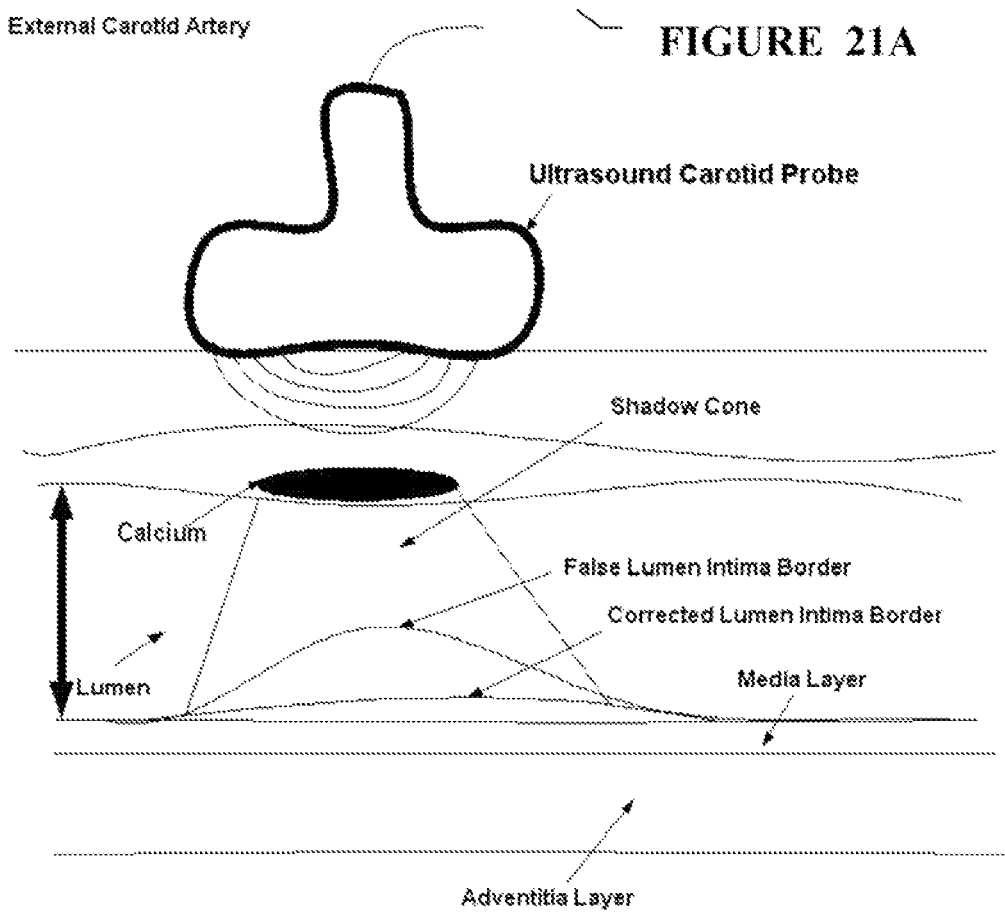
FIG. 21B shows the calcification seen in the proximal wall (near wall) of the ICA and its corresponding shadow.

AWR Compulsion when the Longitudinal Ultrasound Images have Shadows:

Normally, when then walls do not have the calcium shadows, then the above AWR system be applied. FIGS. 21-26 show the AtheroEdge™ system when there are shadows in the longitudinal carotid ultrasound wall region. FIG. 21 shows the OPD (object process diagram) for the whole system when the shadows are present in the ultrasound scans. The top box shows the interacting system between ultrasound machine, patient and user. This invention is applicable to vascular ultrasound for carotid, brachial, aortic and femoral but not limited to these alone. For carotid, one can use the left and the right scan. When the patient conies in, the system is made to get ready for the ultrasound scan and IMT measurement and AWR computation. Patient is positioned optimally for the best scan and then Gel is applied before vascular scanning. The probe is then skin surfaced for the carotid scan as seen in the FIG. 21A. The first sub-system in FIG. 23 shows the patient positioning and vascular scanning system. The input to this block is vascular scan type: carotid, brachial, femoral and aortic, which means these four kinds of arteries, can be used for IMT measurement and AWR computation. The output to the system is the real time ultrasound vascular scan, normally DICOM in format. In the FIG. 23 is also shown that the user completely monitors the system all the time and is in user's control all the time. This allows for perfect synchronization of the patient interface with ultrasound and for the diagnostic IMT measurement and AWR computation. Normally, the vascular screening is done by the vascular surgeon or a neuroradiologist or a sonographer or a cardiologist. They are trained to recognize any calcium present near the proximal wall zone. The diamond box shows if the calcium is present in arterial wall or not. The user such as neuroradiologist or sonographer or cardiologist or vascular surgeon uses his expertise to spot the calcium and its shadow in the proximal (near) end of the arterial wall. Those skilled in the art will note that even though the probe is used longitudinally in B-mode for scanning the arterial wall, one can change the orientation of the probe orthogonal to the blood flow and move the probe linearly along the carotids or brachial or femoral or aortic to get the transverse slices to see the extent (range) of the calcium.

Since the presence of the calcium in longitudinal B-mode scans causes the calcium cone in the ultrasound images, a different processing stage is required before AtheroEdge™ stand alone is applied for IMT measurement and AWR computation. AtheroEdge™ is made to activate if there is no calcium present while AtheroEdge™ system with calcium correction is made to activate when calcium is spotted in the longitudinal or transverse B-mode images. The output of the AtheroEdge™ (with or without calcium system) is the real time IMT measurement and AWR computation. Note that the user completely monitors the system all the time and is in user's control all the time during the AtheroEdge™ system with calcium and AtheroEdge™ system without calcium.

Figure 22:
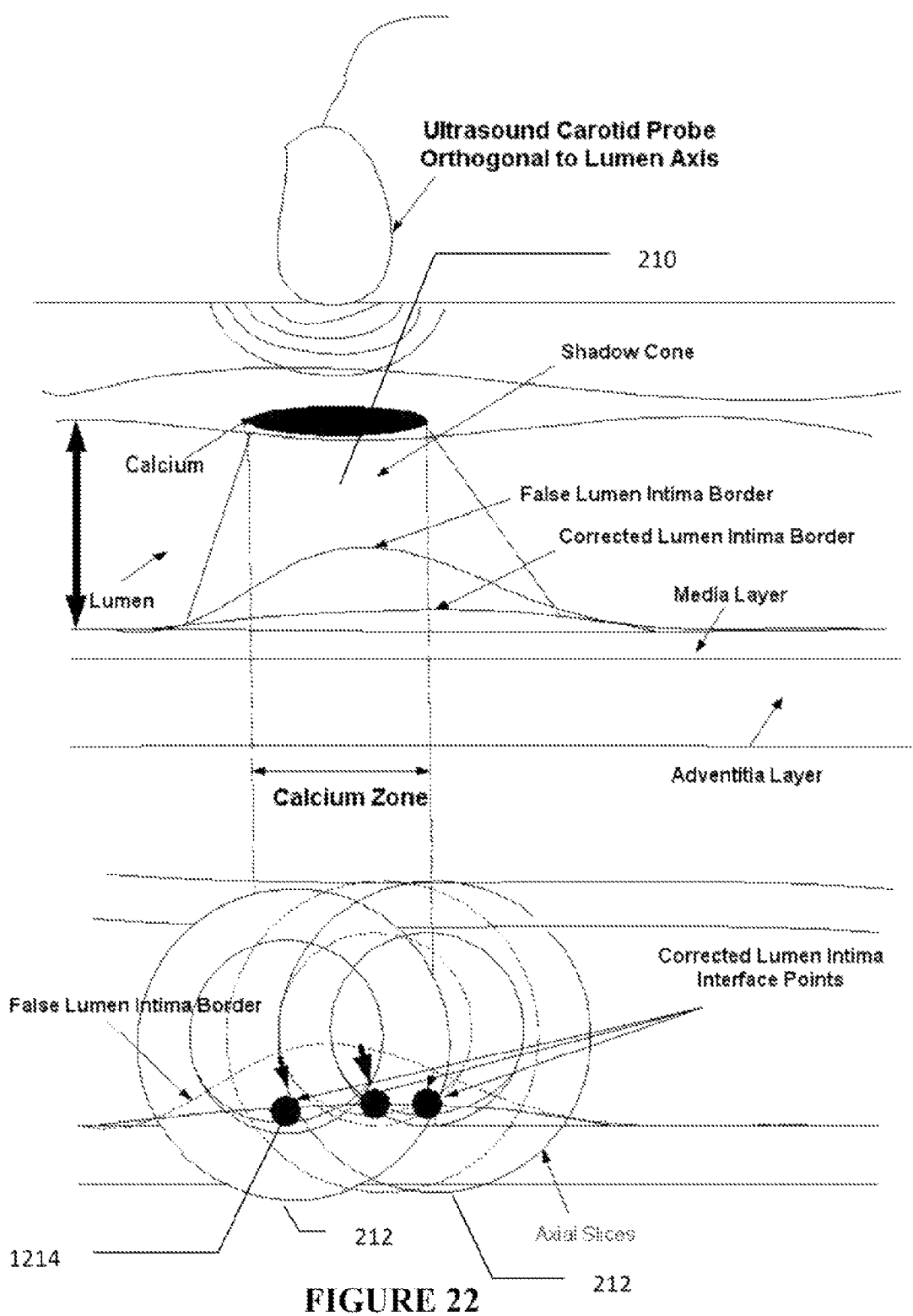
FIG. 22 shows the solution of the calcification issue, where the transverse slices are acquired instead of B-mode longitudinal images. These transverse slices are depicted as circular cross-sectional in the image. This can be used for Atherosclerotic Wall Region estimation.
Figure 23:
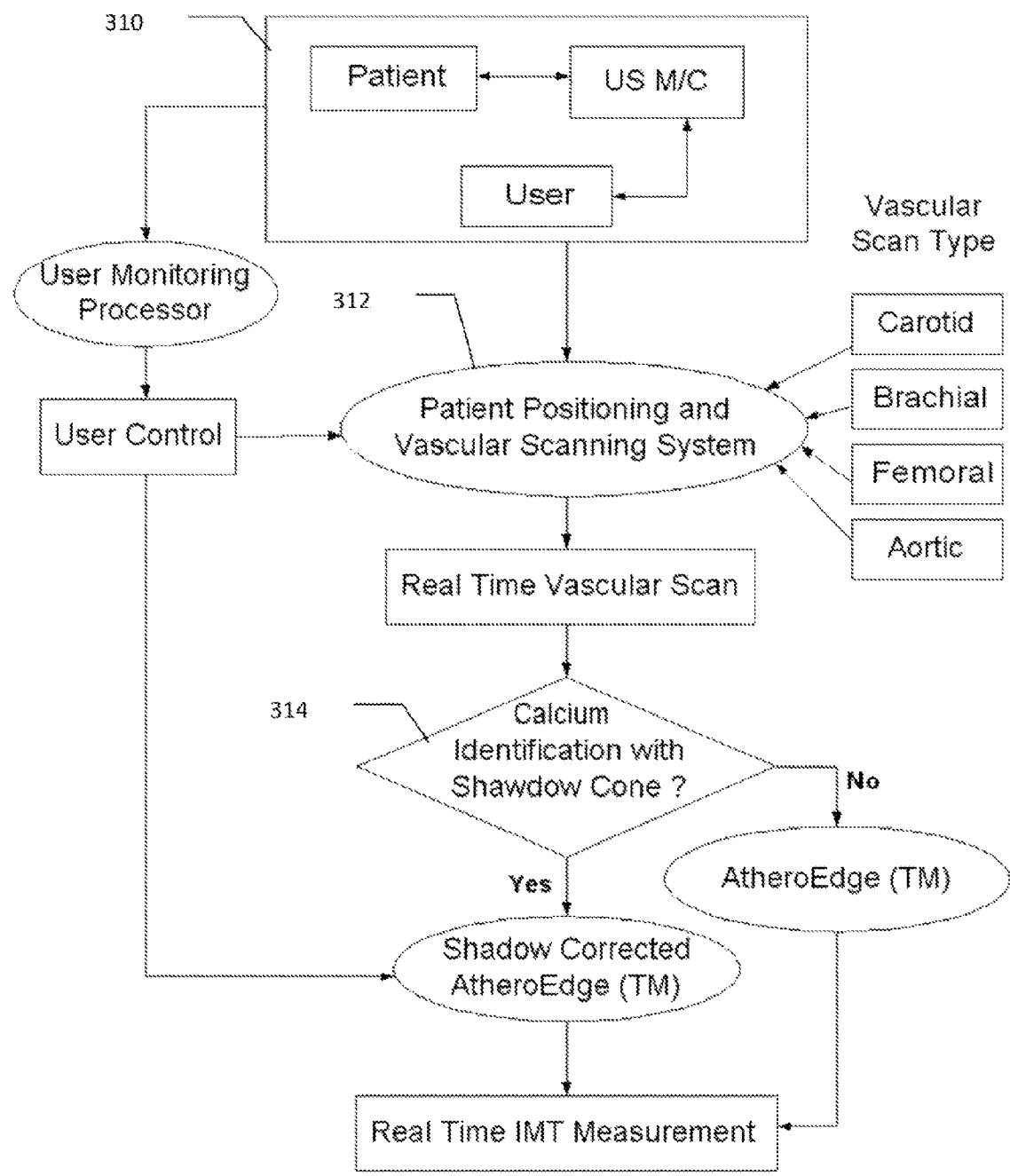
FIG. 23 shows the overall system of an example embodiment (utilizing AtheroEdge™), which can be applied for computation of the IMT for any kind of vascular ultrasound data such as coming from Carotid, Brachial, Femoral and Aortic.

FIG. 22 shows the diagrammatic view where calcium is present in the proximal wall. As can be seen in the Figure a black region in the image in intima layer or media layer or in the lumen region but hanging from the intima layer. There are many variability of how the calcium can stick or hang in the proximal wall, but in every case, there will be a shadow caused when ultrasound is blocked by this calcium present in the arterial wall (see the details by Robin Steel et al., Origins of the edge shadowing artifact I medical ultrasound imaging, Ultrasound in Med. & Biol., Vol. 30, No. 9, pp. 1153-1162, 2004). It has been shown that calcification causes echogenity in the ultrasound image to be hypoechoic (darker) and covers the true reflection coming out of the media layer of the distal (far) borders. Okuda et al. showed these kinds of hypo echoic zones in the ultrasound images due to the presence of calcium in the renal arteries (see, Okuda et al., Sonographic Features of Hepatic Artery Calcification in Chronic Renal Failure, Acta Radiologica 44, 2003. 151-153). IMT measurements and AWR computation in such cases can become difficult or challenging. This application just not finds the reliable and automated IMT measurements and AWR computation in ordinary arterial walls, but also in the presence of calcification. This makes the AWR estimation robust and hence the classification and risk score estimation. FIG. 22 shows the calcification of the proximal end of the wall and the shadow cone made by the calcification and projected onto the distal (far) end of the wall. Due to this as shown in the Figure the LI borders are over calculated or wrongly calculated. Shown in the Figure that using this patent application, we can correct the LI borders for the distal (far) end of the wall. This correction has to be applied in the region where calcification is present.

Thus we need a method, which can actually compute the IMT values and AWR computation if the user (cardiologist, neuroradiologist, vascular surgeon, sonographer) does not find the calcium shadows. We need a reliable, real time and accurate method for IMT measurement and AWR computation when there is no calcium present. Similarly, we need to find IMT and AWR computation when the calcium is present. When calcium is not present, the IMT computation and AWR computation uses AtheroEdge™ directly, but when calcium is present the system uses AtheroEdge™ in the non-calcium zones and correcting the LI border in the calcium zones and then interpolating with the LI border of the non-calcium zone thereby getting the complete and correct LI borders.

FIG. 23 shows the methodology used for correcting the LI borders when the calcium shadow cones are present. The method uses a combination of data acquisition and software method for correcting the LI borders. These two steps are done in real time while the probe is still sitting on the patient's artery. The combinational approach requires no change by the expert user (cardiologist, neuroradiologist, vascular surgeon, sonographer) who has been trained to use the probe on arterial anatomy. The holding method of using the probe still uses the same art by making the grip of four fingers and one thumb. The only change the user has to do is rotate his wrist 90 degree to the longitudinal axis. Once the calcium region is identified, the user (cardiologist, neuroradiologist, vascular surgeon, sonographer) rotates the orientation of the probe by rotating its wrist and taking the scans of the distal (far) wall. Since the probe is oriented orthogonal to the longitudinal axis of the arterial vessel, the images captures are axial or transverse in nature. The user then moves the probe with a reasonable speed linearly and while moving the probe, the transverse images are captured. The user can stop the linear movement of the probe as soon as the calcium region finishes.

These axial slices will show the vessel wall which is circular band in nature. The inner wall shows the lumen region and outer wall is the adventitia walls. Since the application interested in the distal (far) walls in longitudinal B-mode, we look for the vessel wall region in the distal area of the artery. Those skilled in the art of doing 3D ultrasound will notice that the lumen region is dark (black) and the vessel wall (relatively brighter than lumen region), hence the interface region is discernable between lumen and walls. This change in gradient information for the distal (far) wall for that particular slice will allow the user manually or semi-automatically or automatically to estimate the gradient change between the lumen and vessel wall for that orthogonal slice. FIG. 22 shows the circular wall boundaries of the lumen and media-adventitia layers in axial or transverse slices. The point of gradient change between the lumen and vessel wall corresponding to the longitudinal B-mode position of the probe, orthogonal to the arterial axis is the point, which corresponds to the 1.1 border where calcium region was hit. This point is shown as a black circle in the FIG. 22. Those skilled in the art of boundary estimation can use off the shelf snake method or deformable method or edge detection method to find the lumen boundary in the transverse slice of the ultrasound arterial image. The above process of finding the point of intersection of the longitudinal B-mode position to the circular vessel wall in the transverse image is repeated for all the transverse slices where calcium region is identified. The information extracted for the shadow region is stored to be reused because that is the partial information on the LI border. The rest of the information will be extracted from AtheroEdge™ using the longitudinal B-mode vascular ultrasound image.

Figure 24:
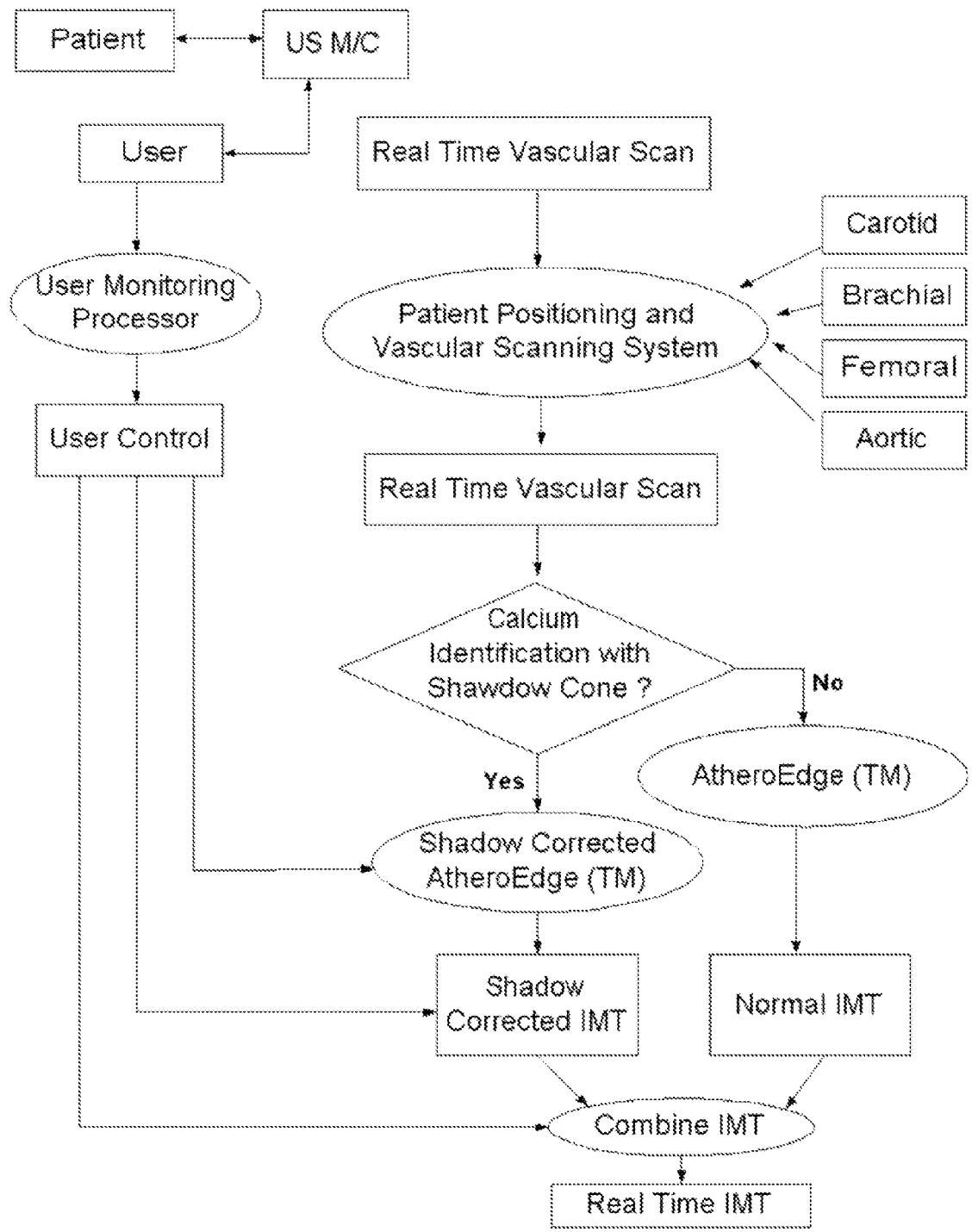
FIG. 24 shows the IMT values are combined with and without shadow cones. If there are no shadow cones (or calcium present), then the processes simply compute the real time IMT.

FIG. 24 actually shows the system which helps in combining the corrected LI boundary information from the calcium shadow zone (shadow corrected AtheroEdge™) and LI boundary information for the non-calcium shadow zone. This will lead to the formation of the full LI boundary and MA boundary leading to the distance measurement called IMT. This can be seen in the FIG. 24. During the complete process, we must ensure that user in full control as a fall back system should the automated system encounters a challenge, there by changing to the semi-automated system. If the user (cardiologist, neuroradiologist, vascular surgeon, sonographer) does not encounter the calcium shadow, then, the plain automated AtheroEdge™ will run for the IMT measurement.

Figure 25:
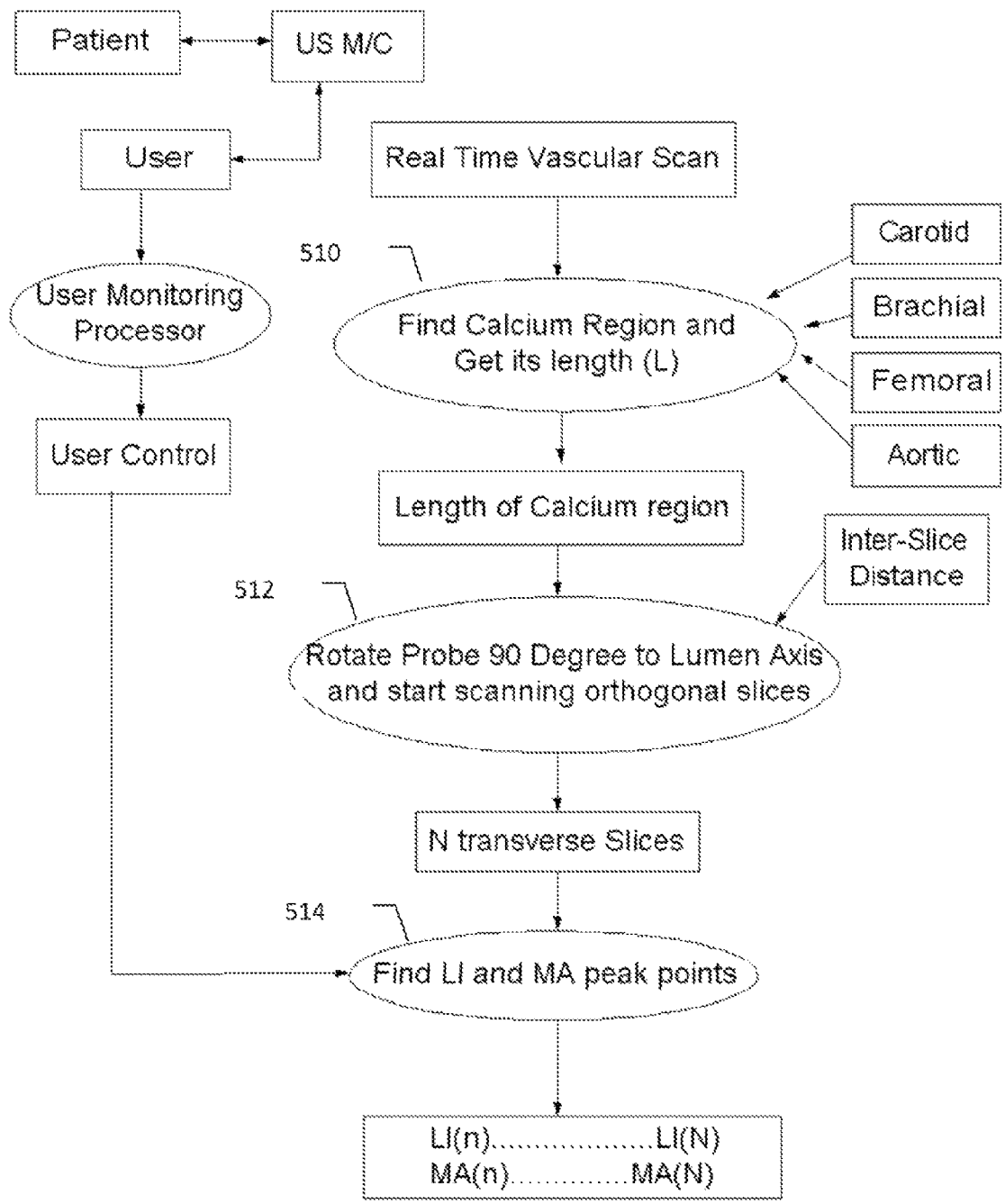
FIG. 25 shows data acquisition when the calcium is found in the proximal wall of the CCA/ICA during the ultrasound scans. The figure shows how the calcium zone is estimated in the proximal wall, then, how the probe orientation is changed to collect the transverse slices in the calcium zone. Finally, the figure shows how the LIMA points are determined in the transverse slices building the correct Atherosclerotic Wall Region, which can then be used for on-line and off-line grayscale feature estimation and wall variability computation.

FIG. 25 shows how the system for computing the LI and MA boundaries in the calcium shadow zone, which is connected to the FIG. 25. The main components are the length of calcium zone estimation, acquiring the N transverse slices and then estimating the LI boundary points corresponding to the shadow zone. Those skilled in the art of 3D ultrasound acquisition will notice that the inter-slice distance is important during the scanning process. In our methodology, it is not very critical information as we are only interested in limited number of points corresponding to the calcium zone.

Figure 26:
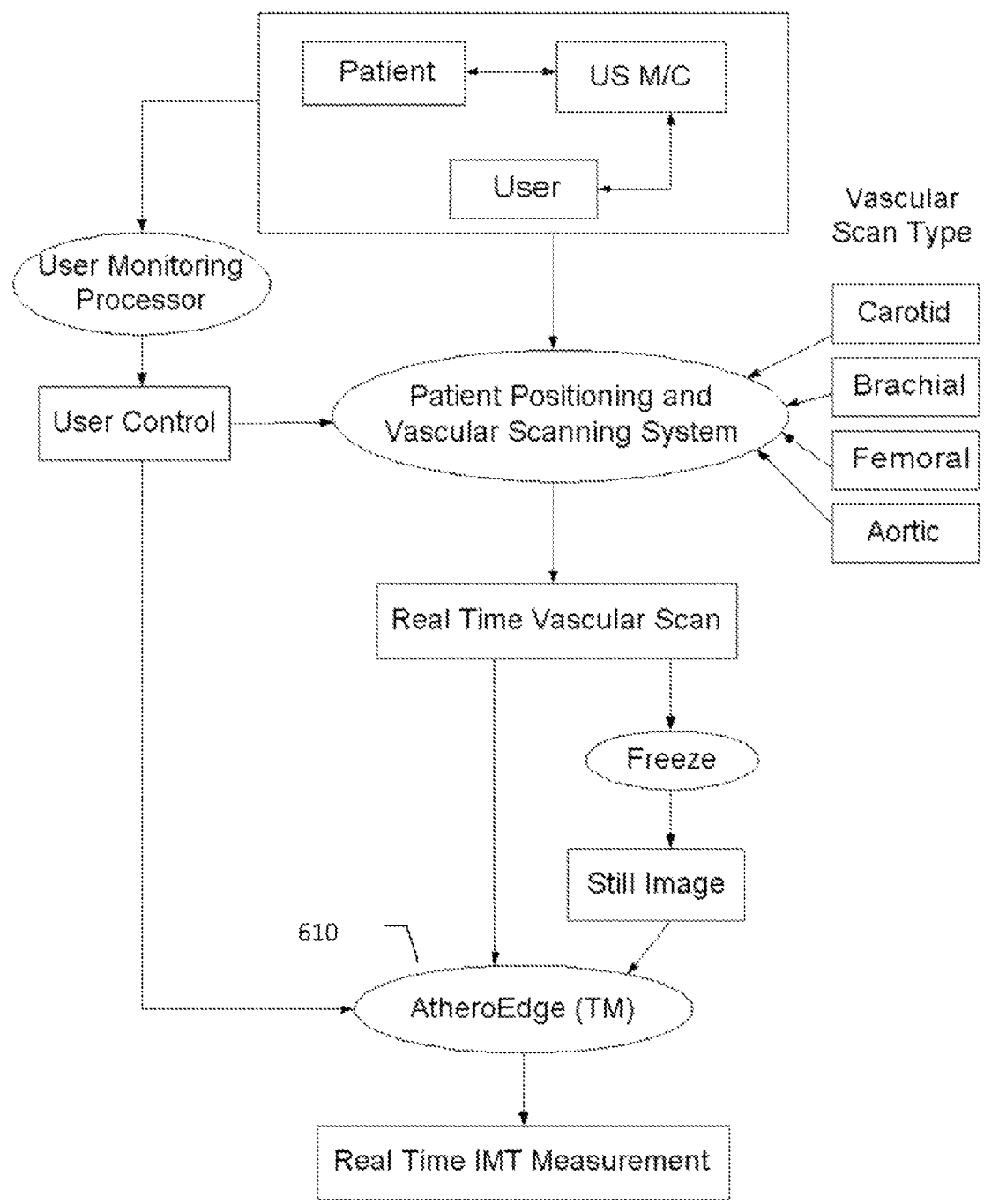
FIG. 26 shows how the system of various embodiments works given the still image of the B-mode longitudinal image of carotid or how the system of various embodiments works given the real time image of the B-mode longitudinal image of the carotid artery.

FIG. 26 shows the system where the AtheroEdge™ is being used in normal cases where there is no calcium shadow. The system shows how the ultrasound vascular image is acquired using the longitudinal B-mode process. The input to the system also shows that this process can take any of the four arteries: carotid, brachial, femoral and arotic. The system has ability to freeze the image as a still image, on which the IMT will be computed. User continuously monitors the process at all stages during the operation. User has control on the AtheroEdge™ software system, ultrasound machine, ultrasound probe, patient and the graphical user interface. The still image can be saved on the hard drive or CD drive. The still image can then also be transferred to an independent computer and AtheroEdge™ can be run on that system as well. At the same time AtheroEdge™ can run real time while the patient is in the vascular screening room.

Figure 27:
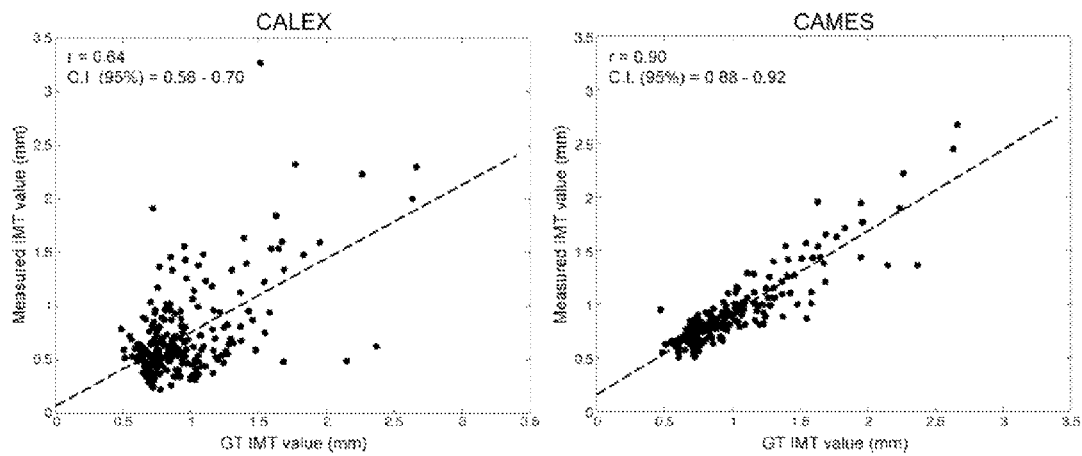
FIG. 27 and FIG. 28 results show the performance output of the LIMA processor (showing the art how the IMT computed from the AtheroEdge™ system and the ground truth IMT computed). The AtheroEdge™ system is called here as CAMES or CALEX (see publication J Ultras Med, 29, (2010), 399-418 and Completely Automated Multi-Resolution Edge Snapper (CAMES)—A New Technique for an Accurate Carotid Ultrasound IMT Measurement and its Validation on a Multi-Institutional Database, in SPIE Medical Imaging Conference. 2011: Lake Buena Vista (Orlando), Fla. USA).
Figure 28:
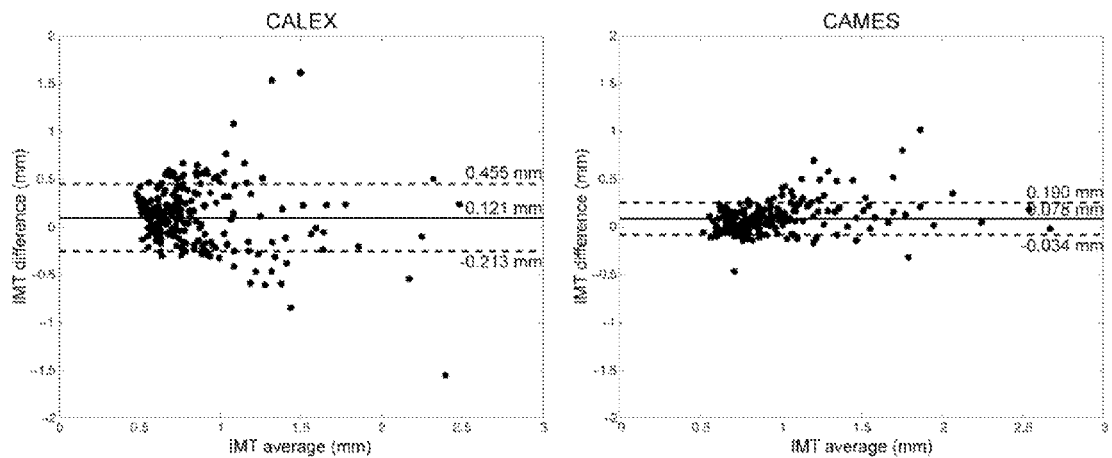

FIG. 27 and FIG. 28 results shows the performance output of the LIMA processor. The regression curve between the IMT measured using AtheroEdge™ system and IMT computed using the ground truth values. The method used can he seen in the published papers:

F. Molinari, G. Zeng, and J. S. Suri. An integrated approach to computer-based automated tracing and its validation for 200 common carotid arterial wall ultrasound images: A new technique, J Ultras Med, 29, (2010), 399-418.

F. Molinari, G. Zeng, and J. S. Suri, Intima-media thickness: setting a standard for completely automated method for ultrasound, IEEE Transaction on Ultrasonics Ferroelectrics and Frequency Control, 57(5), (2010), 1112-1124.

S. Delsanto, F. Molinari, P. Giustetto, W. Liboni, S. Badalamenti, and J. S. Suri, Characterization of a Completely User-Independent Algorithm for Carotid Artery Segmentation in 2-D Ultrasound Images, Instrumentation and Measurement, IEEE Transactions on, 56(4), (2007). 1265-1274.

S. Delsanto, F. Molinari, P. Giustetto, W. Liboni, and S. Badalamenti, CULEX-completely user-independent layers extraction: ultrasonic carotid artery images segmentation, Conf Proc IEEE Eng Med Biol Soc, 6, (2005), 6468-71.

S. Delsanto, F. Molinari, W. Liboni, P. Giustetto, S. Badalamenti, and J. S. Suri, User-independent plaque characterization and accurate IMT measurement of carotid artery wall using ultrasound, Conf Proc IEEE Eng Med Biol Soc, I, (2006), 2404-7.

F. Molinari, S. Delsanto, P. Giustetto, W. Liboni, S. Badalamenti, and J. S. Suri, User-independent plaque segmentation and accurate intima-media thickness measurement of carotid artery wall using ultrasound, in, Number of 111-140 (2008, Artech House, Norwood, Mass. 20081).

F. Molinari, W. Liboni, P. Giustetto, E. Pavanelli, A. Marsico, and J. Suri, Carotid plaque characterization with contrast-enhanced ultrasound imaging and its histological validation, The Journal for Vascular Ultrasound, 34(4), (2010), 1-10.

F. Molinari, C. Loizou, G. Zeng, C. Pattichis, D. Chandrashekar, M. Pantziaris, W. Liboni, A. Nicolaides, and J. Suri, *Completely Automated Multi-Resolution Edge Snapper (CAMES)—A New Technique for an Accurate Carotid Ultrasound IMT Measurement and its Validation on a Multi-Institutional Database*, in *SPIE Medical Imaging Conference*. 2011: Lake Buena Vista (Orlando), Fla. USA.

FIG. 29 (table) results show the significant features that had a p-value less than 0.05.

FIG. 30 (table) shows the symptomatic vs. asymptomatic classifier measures obtained using all the grayscale features (HOS, Texture and DWT), but without the wall variability feature.

FIG. 31A (table) shows the symptomatic vs. asymptomatic classifier measures obtained using all the grayscale features (HOS, Texture and DWT), and with the wall variability feature.

FIG. 31B (table) results show the significant features that had a p-value less than 0.05, when the features are FD, LBP and LME.

FIG. 31C shows the symptomatic vs. asymptomatic classifier measures obtained using all the grayscale features (FD, LBP, LME), and with the wall variability feature.

FIG. 32 (table) shows the AtheroEdge™ system parameters for stage I and stage II.

FIG. 42 shows the role of LBP computation method. Circularly symmetric neighbor sets for different P and R. The centre pixel denotes $g_c$ and the surrounding pixels depict $g_p$, $p=0, \ldots, P-1$; left: P=8, R=1, middle: P=16; R=2; right: P=24, R=3.

FIG. 43 shows the table for the Atheromatic™ system showing the separation between the symptomatic cases and asymptomatic cases.

Figure 44:
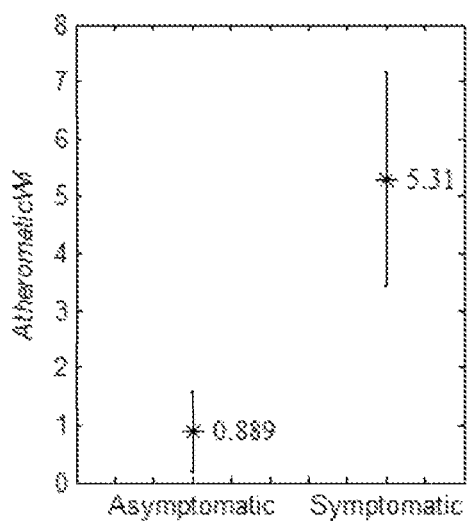
FIG. 44 shows the Atheromatic™ index showing the separation.

FIG. 44 shows the results of the Atheromatic™ system showing the separation between the symptomatic cases and asymptomatic cases.

Figure 45:
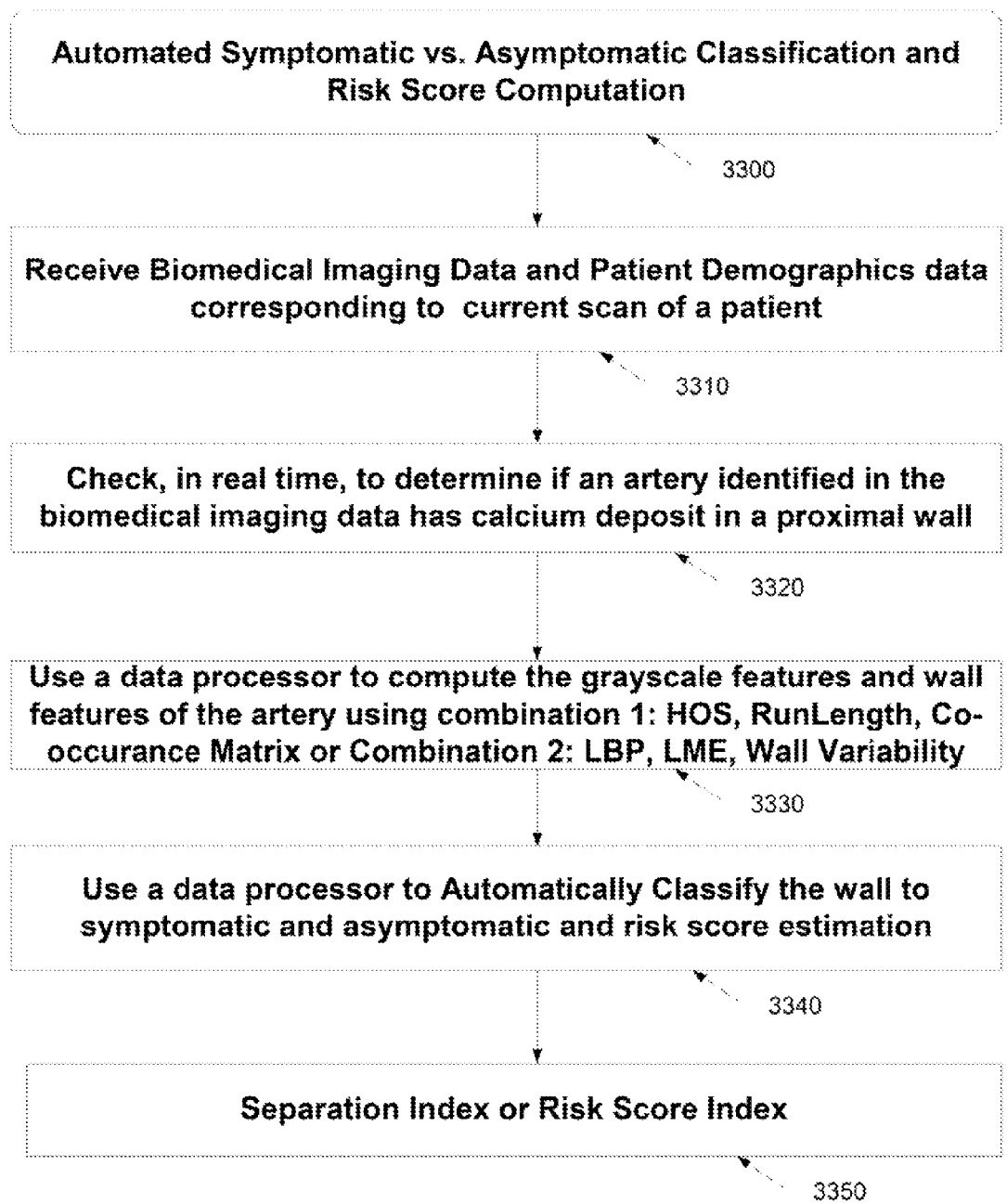
FIG. 45 is a processing flow diagram illustrating an example embodiment of the method as described herein.

FIG. 45 is a processing flow diagram illustrating an example embodiment of the method as described herein. The method 3300 of an example embodiment includes: receiving biomedical imaging data and patient demographic data corresponding to a current scan of a patient (processing block 3310); checking, in real time, to determine if an artery identified in the biomedical imaging data has calcium deposit in a proximal wall (processing block 3320); acquiring arterial data related to the artery as a combination of longitudinal B-mode and transverse B-mode; computing the grayscale features and wall features using combination 1 (HOS, Run-Length, Co-occurrence matrix) or combination 2 (LBP, LME, Wall Variability) developing the training model and generating the training parameters (processing block 3330); using a data processor to automatically recognize the artery as symptomatic or asymptomatic (processing block 3340); and using a data processor to determine a cardiovascular stroke risk score (processing block 3350).

Figure 46:
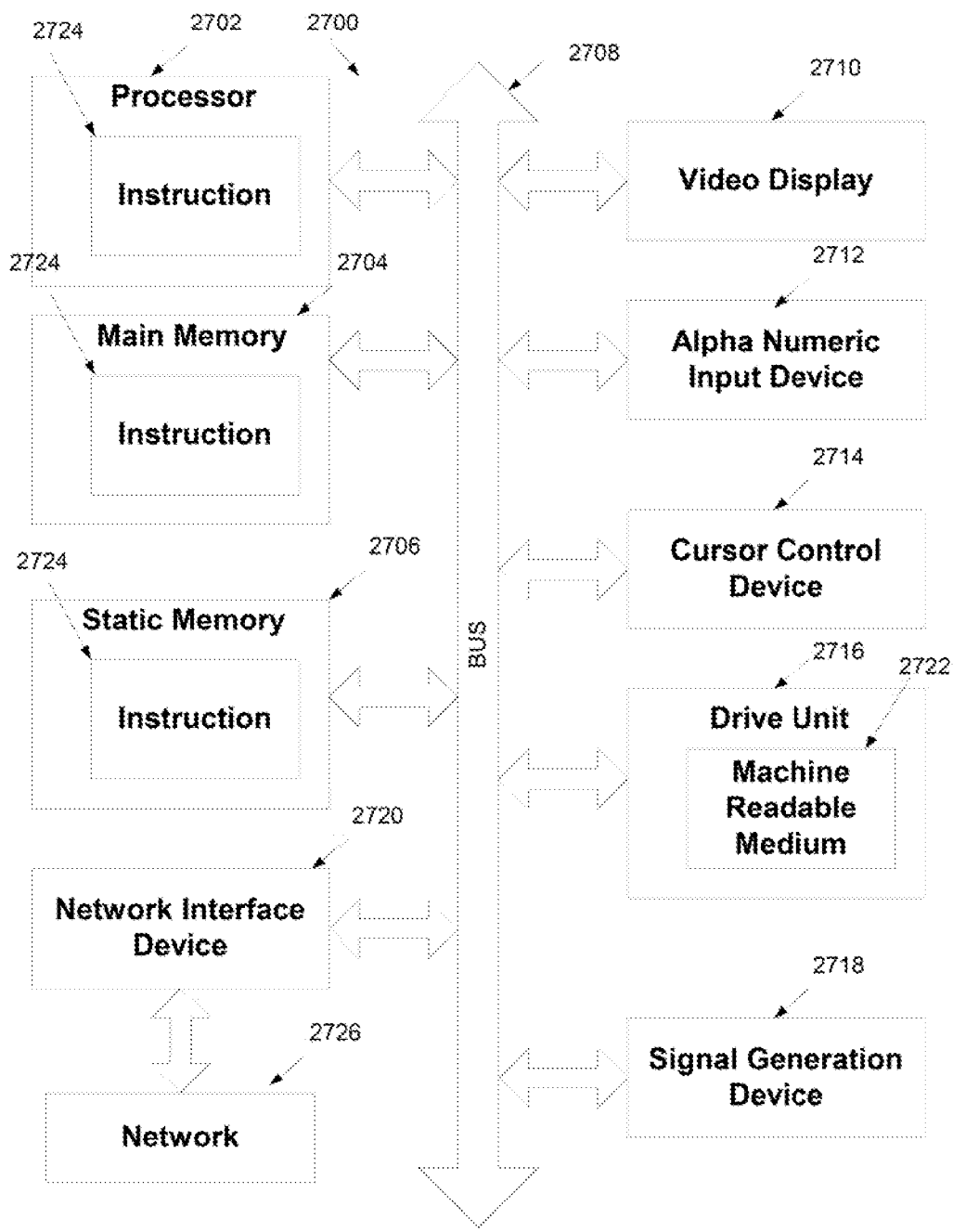
FIG. 46 shows a diagrammatic representation of machine in the example form of a computer system within which a set of instructions when executed may cause the machine to perform any one or more of the methodologies discussed herein.

FIG. 46 shows a diagrammatic representation of machine in the example form of a computer system 2700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 2700 includes a processor 2702 (e.g., a central processing unit (CPU), a graphics processing unit (GPU), or both), a main memory 2704 and a static memory 2706, which communicate with each other via a bus 2708. The computer system 2700 may further include a video display unit 2710 (e.g., a liquid crystal display (LCD) or a cathode ray tube (CRT)). The computer system 2700 also includes an input device 2712 (e.g., a keyboard), a cursor control device 2714 (e.g., a mouse), a disk drive unit 2716, a signal generation device 2718 (e.g., a speaker) and a network interface device 2720.

The disk drive unit 2716 includes a machine-readable medium 2722 on which is stored one or more sets of instructions (e.g., software 2724) embodying any one or more of the methodologies or functions described herein. The instructions 2724 may also reside, completely or at least partially, within the main memory 2704, the static memory 2706, and/or within the processor 2702 during execution thereof by the computer system 2700. The main memory 2704 and the processor 2702 also may constitute machine-readable media. The instructions 2724 may further be transmitted or received over a network 2726 via the network interface device 2720. While the machine-readable medium 2722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

Classification Results for Longitudinal Ultrasound:

The average accuracy, PPV, sensitivity, and specificity values obtained by feeding all the features except the Wall Feature into five different kernel configurations of SVM, KNN, PNN, DT, and Fuzzy classifiers are presented in FIG. 30 (Table). The results obtained using all the significant features including the Wall Feature in the classifiers are presented in FIG. 31A (Table). In both FIG. 30 (table) and FIG. 31A (table), the values indicated are averages obtained in the three folds of testing. TN indicates the number of True Negatives, FN the number of False Negatives, TP the number of True Positives, and FP the number of False Positives. It is evident that the classifiers show improved performance when the Wall Feature is included in the training process. The highest accuracy of 94.4% was registered by the KNN classifier FIG. 31A (table).

FIG. 31B (table) shows the Significant features of the wall data with FD, LBP, LME features, that had a p-value <0.0001 and their ranges for symptomatic and asymptomatic classes.

FIG. 31C (table) presents the classification results obtained using the features from the Wall-dataset. Also shown in these tables are the average number of True Positives (TP), True Negatives (TN), False Positives (FP), and False Negatives (FN). Depending on the number of FPs and FNs, classifiers with almost similar accuracies might register varying values for sensitivity and specificity. To ensure that the optimal classifier is chosen, one should select a classifier that has high accuracy as well as similarly high values for both sensitivity and specificity. If sensitivity is high and specificity is very low and vice versa, then that classifier is more biased towards detecting only one of the classes correctly.

For the Wall-dataset with features of FD, LBP, LME, IMTV, the optimal classifier would either be the KNN or the RBPNN as both registered high values for accuracy (89.5%), sensitivity (89.6%) and specificity (88.9%) (FIG. 31C).

Atheromatic Wall Index Using the Features (LBP+LME+IMTV)

The Atheromatic™ is calculated using Equation shown below. The range of this index for both the symptomatic and asymptomatic classes is presented in FIG. 43 (table) and the corresponding box plot is shown in FIG. 44. FIG. 43 shows the Mean±Standard Deviation of the Atheromatric™ for both asymptomatic and symptomatic classes. Again, this wall index (using combination 2) is also significantly different for the two classes. The symptomatic images have a higher value for this index because they have higher values for the $IMTV_{poly}$ feature and LME2 (component on the numerator N of the equation below), and lower values for $LBP_{324}Ene$ (component on the denominator D of the equation). The value of bias β was taken to be 10 and χ was taken to be 5. This Wall Index may be used by the clinicians for a more objective, real-time, and faster classification of symptomatic vs. asymptomatic plaque walls. This index is single valued index and do not require any subjective interpretation.

$$AtheromaticWi = \beta \times IMTV_{poly} \times \log_{10}\left(\frac{N}{D} + \chi\right)$$

$$N = LME2$$

and $$D = LBP_{324}Ene \times LME8$$

The values of for $LBP_{324}Ene$ can be seen in the FIG. 31B.

Application of Atheromatic™ in CT/MR/3D Carotid Ultrasound

Computed tomography images of the carotid artery provide unique 3D images of the artery and plaque that could be used for calculating percentage stenosis. On using the Atheromatic™ system on images obtained using non-invasive Multi-Detector row CT Angiography (MDCTA) and using the texture-based features and discrete wavelet transform based features, one can use the same paradigm for classification of carotid wall plaque images into symptomatic vs. asymptomatic and computation of the risk score index.

An example of MDCTA symptomatic and asymptomatic wall region is shown in FIGS. 34, 35, 36 and 37.

Example of Texture Features using Gray Level Co-occurrence Matrix (GLCM) and the run length matrix to extract texture features from the segmented images of the carotid artery. The features are briefly described below.

Co-occurrence Matrix: The GLCM of a m×n image is defined as:

$$C_d = \left| \left\{ \begin{array}{c} (p, q), (p + \Delta x, q + \Delta y): I(p, q) = i, \\ I(p + \Delta x, q + \Delta y) = j \end{array} \right\} \right|$$

where (p, q), (p+Δx, q+Δy) belong to m×n, d=(Δx,Δy) and |...| denotes the set cardinality. The probability of a pixel with a gray level intensity i having a pixel with a gray level intensity j at a distance (Δx,Δy) away in the image is given by $$P_d(i, j) = \frac{C_d(i, j)}{\sum_{(i)}\sum_{(j)} C_d(i, j)}$$

where the summation is over all possible i and j. We calculated the following features using equations (1) and (2).

Energy: $\sqrt{\sum_i \sum_j [P_d(i, j)]^2}$

Contrast: $\sum_i \sum_j (i - j)^2 P_d(i, j)$

Homogeneity: $\sum_i \sum_j \frac{P_d(i, j)}{1 + (i - j)^2}$

Entropy: $-\sum_i \sum_j P_d(i, j) \cdot \ln P_d(i, j)$

Moments: $m_g = \sum_i \sum_j (i - j)^g P_d(i, j)$

We calculated $m_1$, $m_2$, $m_3$, and $m_4$ in this work.

Angular Second Moment $\sum_{k=0}^{n-1} P_\delta(k)^2$ where $P_\delta(k) = \sum_i \sum_j C_d(i, j)$ in which |i−j|=k, k=0, 1, ... n−1, and n is the number of gray scale levels.

Run Length Matrix: The run length matrix $P_\theta[24]$ contains all the elements where the gray level intensity i has the run length j continuous in direction θ. The direction θ is set as 0°, 45°, 90°, or 135°. In this work, we calculated the following features based on $P_\theta$.

Short run emphasis: $\sum_i \sum_j \frac{P_\theta(i, j)}{j^2} / \sum_i \sum_j P_\theta(i, j)$ Long run emphasis: $\sum_i \sum_j j^2 P_\theta(i, j) / \sum_i \sum_j P_\theta(i, j)$ Gray level non-uniformity: $\sum_i \left\{ \sum_j P_\theta(i, j) \right\}^2 / \sum_i \sum_j P_\theta(i, j)$ Run length non-uniformity: $\sum_j \left\{ \sum_i P_\theta(i, j) \right\}^2 / \sum_i \sum_j P_\theta(i, j)$ Run percentage: $\sum_i \sum_j P_\theta(i, j) / A$ where A is the area of the image. The index i runs over the gray level values in the image and the index j runs over the run length.

DWT feature for MDCTA data set: As discussed in Ultrasound above, Discrete Wavelet Transform (DWT) is a transform that captures both the time and frequency information of the image. When two-dimensional DWT is applied to CT/MR images, it decomposes the image into coarse approximation coefficients using low-pass filters and finer detail coefficients using high-pass filters. This decomposition is done iteratively on the low-pass approximation coefficients obtained at each level, until the necessary iterations are reached. FIG. 41 shows the pass band structure for a 2D sub-band transform at three levels. We used Daubechies (Db) 8 as the mother wavelet in this work. Specifically, LL coefficients are obtained when Low Pass Filtering (LPF) is applied on both rows and columns in the image. HL coefficients (vertical details) are obtained when LPF is applied on rows, and High Pass Filtering (HPF) is applied on columns. LH coefficients (horizontal details) are the result of applying HPF on rows and LPF on columns. When both the rows and columns are filtered using HPF, we get the diagonal or detail coefficients HH. Further decompositions are done on the LL sub-band to obtain the next coarser scale of wavelet coefficients. All the elements within the individual rows of the matrix containing the coefficients are added, and the elements of the resulting vector are squared before adding to form a scalar value. Subsequently, this value is normalized by dividing it by the number of rows and columns of the original matrix. FIG. 41 also shows the resultant features $A_2, H_2, H_1, V_2, V_1, D_2, D_1$ i.e. $HH_1$, after the above described process, results in feature $D_1$, and so on.

Significant features from MDCTA were then used to train and test a Support Vector Machine (SVM) classifier shown in the table below:

| Feature | Symptomatic | Asymptomatic | p-value |
|---|---|---|---|
| Entropy | 1.78 ± 0.267 | 1.55 ± 0.134 | <0.0001 |
| Angular2ndMoment | 3.469E+06 ± 3.599E+05 | 3.926E+06 ± 1.749E+05 | <0.0001 |
| ShortRunEmphasis (0°) | 0.769 ± 2.506E−02 | 0.733 ± 3.491E−02 | <0.0001 |
| $D_1$ | 4.752E−03 ± 1.002E−03 | 3.717E−03 ± 5.210E−04 | <0.0001 |

Sample results shows the Accuracy results when Atheromatic™ system when applied to MDCTA:

| Kernel Types | TN | FN | TP | FP | Accuracy (%) | PPV (%) | Sensitivity (%) | Specificity (%) |
|---|---|---|---|---|---|---|---|---|
| Linear Kernel | 49 | 9 | 51 | 11 | 83.9 | 85.7 | 85.6 | 82.2 |

| Kernel Types | TN | FN | TP | FP | Accuracy (%) | PPV (%) | Sensitivity (%) | Specificity (%) |
|---|---|---|---|---|---|---|---|---|
| Poly Kernel, O = 1 | 49 | 9 | 51 | 11 | 83.6 | 85.7 | 85 | 82.2 |
| Poly Kernel, O = 2 | 49 | 2 | 58 | 11 | 88.9 | 85.4 | 96.7 | 81.1 |
| Poly Kernel, O = 3 | 51 | 3 | 57 | 9 | 90 | 87.2 | 95.6 | 84.4 |
| RBF Kernel | 48 | 3 | 57 | 12 | 87.2 | 84.3 | 95 | 79.4 |

The best classification results (in terms of accuracy, sensitivity, and specificity) were obtained using the SVM classifier with a polynomial kernel of order 3. TN represents the True Negatives, FN, the False Negatives, TP, the True Positives, and FP, the False Positives. The highest accuracy presented by the proposed technique for plaque categorization was 90% recorded by the SVM classifier with the polynomial kernel of order 3. Even though the highest sensitivity of 96.7% was recorded by the polynomial kernel of order 2, its specificity is very low (81.1%). Such an imbalance in sensitivity and specificity values indicates that the classifier has more capability of classifying only one class correctly than the other. Hence, an optimal classifier should give equally high values for accuracy, sensitivity, and specificity, and therefore, based on the results, the polynomial kernel of order 3 was chosen as the most optimal SVM configuration for this particular work.

Cardiovascular Risk Score (CVRS) or INDEX when using MDCTA can be shown using the features: Entropy, Angular2ndMoment, ShortRunEmphasis (0°), $D_1$:

$$CVRS(MDCTA) = 3 \times \left( Entropy - \frac{\log_{10}(Angular2ndMoment \times ShortRunEmphasis \times D_1)}{10} \right)$$

|  | Symptomatic | Asymptomatic | p-value |
|---|---|---|---|
| CVRS (MDCTA) | 4.10 ± 0.786 | 3.43 ± 0.406 | <0.0001 |

The MDCTA images of plaques provide the clinician information about the plaque size and plaque composition. However, classification of CT carotid plaques into asymptomatic and symptomatic will add value to the MDCTA modality as such a classification will aid the vascular surgeons in making clearer decisions about whether a patient needs risky treatment or not. Plaque classification is a difficult problem and has now been demonstrated for both ultrasound and MDCTA modalities, though more cost effective in ultrasound. Our preliminary results of classifying CT plaque images into symptomatic and asymptomatic are quite promising. The SVM classifier with a polynomial kernel of order 3 presented the highest accuracy of 90%, sensitivity of 95.6%, and specificity of 84.4%. CVRS (MDCTA) also give a unique risk scoe that uses significant features. This CVRS (MDCTA) can be effectively used for monitoring the change in features, and well demonstrated solid tool for plaque characterization.

FIG. 42 is a processing flow diagram illustrating an example embodiment of the method as described herein. The method 3300 of an example embodiment includes: receiving biomedical imaging data and patient demographic data corresponding to a current scan of a patient (processing block 3310); checking, in real time, to determine if an artery identified in the biomedical imaging data has calcium deposit in a proximal wall (processing block 3312); acquiring arterial data related to the artery as a combination of longitudinal B-mode and transverse B-mode (processing block 3314); using a data processor to automatically recognize the artery as symptomatic or asymptomatic (processing block 3316); and using a data processor to determine a cardiovascular risk score (processing block 3318).

FIG. 43 shows a diagrammatic representation of machine in the example form of a computer system 2700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 2700 includes a processor 2702 (e.g., a central processing unit (CPU), a graphics processing unit (GPU), or both), a main memory 2704 and a static memory 2706, which communicate with each other via a bus 2708. The computer system 2700 may further include a video display unit 2710 (e.g., a liquid crystal display (LCD) or a cathode ray tube (CRT)). The computer system 2700 also includes an input device 2712 (e.g., a keyboard), a cursor control device 2714 (e.g., a mouse), a disk drive unit 2716, a signal generation device 2718 (e.g., a speaker) and a network interface device 2720.

The disk drive unit 2716 includes a machine-readable medium 2722 on which is stored one or more sets of instructions (e.g., software 2724) embodying any one or more of the methodologies or functions described herein. The instructions 2724 may also reside, completely or at least partially, within the main memory 2704, the static memory 2706, and/or within the processor 2702 during execution thereof by the computer system 2700. The main memory 2704 and the processor 2702 also may constitute machine-readable media. The instructions 2724 may further be transmitted or received over a network 2726 via the network interface device 2720. While the machine-readable medium 2722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A computer-implemented method comprising:
   receiving biomedical imaging data and patient demographic data corresponding to a current scan of a patient;
   checking, in real time, to determine if an artery identified in the biomedical imaging data has atherosclerosis deposit in a proximal wall;
   acquiring arterial data related to the artery as a combination of longitudinal and transverse for B-mode Ultrasound, CT, MR, 3D IVUS, or 3D carotid Ultrasound for cross-section images;
   using a data processor to automatically estimate the wall borders in longitudinal ultrasound or transverse slices in B-mode ultrasound, CT, MR, 3D IVUS, or 3D carotid Ultrasound images;
   using the data processor to automatically recognize three sets of combinations of features using: a combination 1 consisting of: (a) higher order spectra (HOS) computing the Normalized Bi-spectral Entropy and Normalized Bi-spectral Squared Entropy; (b) Discrete Wavelet Transform (DWT)-based, computing features including Average Horizontal Discrete Wavelet Coefficient (Dh1), Average vertical Discrete Wavelet Coefficient (Dv1), and Energy; and (c) Gray Level Co-occurrence Matrix-based, computing features including Texture Symmetry and Texture Entropy; a type 2 combination consisting of local binary pattern, law's mask energy and Wall Variability features, and a type 3 combination consisting of Higher Order Spectra, Trace Transform, Fuzzy Grayscale Level Co-occurrence Matrix (FGLCM) and Wall Variability;
   using the data processor to apply classifiers using four types of classifiers including: (a) Support Vector Machine; (b) Radial Basis Probabilistic Neural Network (RBPNN), (c) Nearest Neighbor (KNN) classifier, and (d) Decision Trees (DT) Classifier; and
   using the data processor to automatically recognize the artery as symptomatic or asymptomatic; and
   using the data processor to determine a cardiovascular risk score.

2. The method as claimed in claim 1 wherein the biomedical imaging data comprising a combination of two-dimensional (2D) longitudinal B-mode and two-dimensional (2D) transverse B-mode ultrasound images, when atherosclerosis is present or not present in the arterial wall.

3. The method as claimed in claim 1 wherein the method is applicable to one of the group: Carotid MR, Carotid CT, IVUS Blood Vessels, Carotid B-mode longitudinal Ultrasound, Femoral B-mode longitudinal Ultrasound, Brachial B-mode longitudinal Ultrasound, and Aorta B-mode longitudinal Ultrasound.

4. The method as claimed in claim 1 wherein the method further includes computing the vessel grayscale features that are based on higher order spectra (HOS), and computing the Normalized Bi-spectral Entropy and Normalized Bi-spectral Squared Entropy.

5. The method as claimed in claim 1 wherein the method further includes computing the vessel grayscale features based on Discrete Wavelet Transform (DWT), and computing features including Average Horizontal Discrete Wavelet Coefficient (Dh1), Average vertical Discrete Wavelet Coefficient (Dv1) and Energy in combination with higher order spectra (HOS) features.

6. The method as claimed in claim 1 wherein the method further includes computing the vessel grayscale features are based on Gray Level Co-occurrence Matrix, and computing the Texture features including Texture Symmetry and Texture Entropy in combination to DWT and HOS features.

7. The method as claimed in claim 1 wherein the method further includes computing the grayscale features based on the Run Length Non-uniformity (RLnU) in combination with DWT and HOS.

8. The method as claimed in claim 1 wherein the method further includes computing the grayscale features based on the Trace Transform (TT) in combination with Fuzzy Grayscale Level Co-occurrence Matrix (FGLCM).

9. The method as claimed in claim 1 wherein the method further includes computing the grayscale features based on Wall Variability, computed using as the standard deviation of the distance between the LI and MA borders of the vessel wall when used in longitudinal B-model carotid ultrasound.

10. The method as claimed in claim 1 wherein the method further includes computing the vessel grayscale features based on a combination of features including: (a) Local Binary Pattern, (b) Law's Mask Energy, (c) Wall Variability or (d) higher order spectra (HOS), computing the Normalized Bi-spectral Entropy and Normalized Bi-spectral Squared Entropy; computing Discrete Wavelet Transform (DWT), computing features including Average Dh1, Average Dv1 and Energy; computing Gray Level Co-occurrence Matrix, computing the Texture features including Texture Symmetry and Texture Entropy.

11. The method as claimed in claim 1 wherein the method further includes computing the grayscale features based on Wall Variability, computed using as the standard deviation of the distance between the LI and MA borders of the vessel wall, where the variability is computed using a Middle line Method and Polyline methods.

12. The method as claimed in claim 1 wherein the method is applied on-line on a test patient image, the method including computing the grayscale features based on a combination 1 consisting of: (a) higher order spectra (HOS) computing the Normalized Bi-spectral Entropy and Normalized Bi-spectral Squared Entropy; (b) Discrete Wavelet Transform (DWT)-based, computing features including Average Dh1, Average Dv1 and Energy; (c) Gray Level Co-occurrence Matrix-based, computing the features including Texture Symmetry and Texture Entropy; and then transforming these features by the trained classifier including Support Vector Machine, Radial Basis Probabilistic Neural Network (RBPNN), Nearest Neighbor (KNN) classifier, or Decision Trees (DT) Classifier.

13. The method as claimed in claim 1 including providing a Support Vector Machine classifier, where the grayscale features used on the training images are: based on a combination 1 consisting of: (a) higher order spectra (HOS) computing the Normalized Bi-spectral Entropy and Normalized Bi-spectral Squared Entropy; (b) Discrete Wavelet Transform (DWT)-based, computing features including Average Dh1, Average Dv1 and Energy; (c) Gray Level Co-occurrence Matrix-based computing the features including Texture Symmetry and Texture Entropy; and (d) Wall Variability-based on standard deviation of the distance between LI and MA borders.

14. The method as claimed in claim 1 further including training using ground truth information from the same modality or any cross-modality including MR, CT, Ultrasound, or IVUS.

15. The method as claimed in claim 1 wherein the method is used to compute the cardiovascular risk score using the grayscale features using a combination 1 from the group: (DWT, Texture and HOS), a combination 2 from the group: (local binary pattern, law's mask energy and vessel wall variability), or a combination 3 from the group: (HOS, Trace Transform, Fuzzy Grayscale Level Co-occurrence Matrix (FGLCM) and Wall Variability).

16. The method as claimed in claim 1 where the grayscale features are computed in the segmentation wall which is computed automatically or manually.

17. The method as claimed in claim 1 wherein the method is used for automated recognition using a multi-resolution approach, where the edges of the MA border are determined in coarse resolution and up-sampled back onto the original high resolution image.

18. The method as claimed in claim 1 wherein the method is for automated recognition of longitudinal carotid using a multi-resolution approach, and the artery location is validated using anatomic information including lumen in real time.

19. The method as claimed in claim 1 where the system is run on a tablet computer or hand-held mobile devices by porting the on-line system to the tablet computer or hand-held mobile device having a display unit.

* * * * *